(12) United States Patent
Wilmott et al.

(10) Patent No.: US 12,357,546 B2
(45) Date of Patent: Jul. 15, 2025

(54) SPRAYABLE COMPOSITIONS CONTAINING OIL-IN-WATER EMULSIONS CONTAINING SUBMICRON HYDROPHOBIC AGENTS AND METHODS OF USE THEREOF

(71) Applicant: LEADING EDGE INNOVATIONS, LLC, Branchburg, NJ (US)

(72) Inventors: James Michael Wilmott, Banger, PA (US); Michael Ross, Easton, PA (US); Purvesh Patel, Piscataway, NJ (US)

(73) Assignee: LEADING EDGE INNOVATIONS, LLC, Branchburg, NJ (US)

( * ) Notice: Subject to any disclaimer, the term of this patent is extended or adjusted under 35 U.S.C. 154(b) by 0 days.

(21) Appl. No.: 18/544,975

(22) Filed: Dec. 19, 2023

(65) Prior Publication Data

US 2024/0207148 A1    Jun. 27, 2024

Related U.S. Application Data

(60) Provisional application No. 63/433,660, filed on Dec. 19, 2022.

(51) Int. Cl.

| | |
|---|---|
| A61K 8/06 | (2006.01) |
| A61K 8/37 | (2006.01) |
| A61K 9/107 | (2006.01) |
| A61K 31/00 | (2006.01) |
| A61K 45/06 | (2006.01) |
| A61K 47/14 | (2017.01) |
| A61Q 17/04 | (2006.01) |
| A61Q 19/00 | (2006.01) |

(52) U.S. Cl.
CPC .............. *A61K 8/068* (2013.01); *A61K 8/062* (2013.01); *A61K 8/37* (2013.01); *A61K 8/375* (2013.01); *A61K 9/1075* (2013.01); *A61K 31/658* (2023.05); *A61K 45/06* (2013.01); *A61K 47/14* (2013.01); *A61Q 17/04* (2013.01); *A61Q 19/00* (2013.01); *A61K 2800/10* (2013.01); *A61K 2800/41* (2013.01); *A61K 2800/805* (2013.01)

(58) Field of Classification Search
None
See application file for complete search history.

(56) References Cited

U.S. PATENT DOCUMENTS

| | | |
|---|---|---|
| 2007/0213234 A1 | 9/2007 | Yaghmur et al. |
| 2014/0193502 A1 | 7/2014 | Tamarkin et al. |
| 2015/0232260 A1 | 8/2015 | Dann et al. |
| 2019/0054440 A1 | 2/2019 | Mistry et al. |
| 2019/0224085 A1 | 7/2019 | Ionidis |

OTHER PUBLICATIONS

International Search Report dated May 16, 2024 for PCT Appl. No. PCT/US2023/084779.
Written Opinion dated May 16, 2024 for PCT Appl. No. PCT/US2023/084779.

*Primary Examiner* — Nannette Holloman
(74) *Attorney, Agent, or Firm* — Ohlandt, Greeley and Perle, L.L.P.

(57) ABSTRACT

Described are sprayable compositions containing oil-in-water emulsions. The emulsions contain (i) submicron particles of one or more hydrophobic agent(s), (ii) an emulsifier system comprising one or more nonionic surfactant(s) or emulsifier(s), and (iii) an aqueous-solute fluid. The submicron particles of one or more hydrophobic agent(s) are present in an amount from about 0.01% wt. to about 70% wt., the one or more nonionic surfactant(s) or emulsifier(s) are present in an amount from about 0.01% wt. to about 10% wt., and the aqueous-solute fluid is present in an amount from about 1.0% wt. to about 98.5% wt., all based on the total weight of the sprayable composition. The submicron particles of one or more hydrophobic agent(s) (i) have an average particle size from about 100 nm to less than about 1000 nm, (ii) have a solubility of less than about 0.1% by weight in water under standard conditions, and (iii) are 85% or more of a size within ±2.0 standard deviations, of the average particle size. The one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion. Also described are processes of making the emulsions, and methods of use of the emulsions. The emulsions are useful, for example, in nutritional, pharmaceutical, biomedical, over-the-counter (OTC) drug, cosmetic, food, personal care, animal care, veterinary health, household, pet care, and other applications.

34 Claims, 2 Drawing Sheets

Fig. 2

Spray Product Forms - Emulsions

| Emulsion Technology | Liquid | Fluid | Spray | Rx Anesthetic | Furniture Polish |
|---|---|---|---|---|---|
| 10cts Dimethicone | E1 E3 | E2 | E3 | | E18 |
| CCTG | E4 | E5 | E6 | | |
| Olive Oil | E7 | E8 | E9 | | |
| C12-15 Alkyl Benzoate | E10 | E11 | E12 | | |
| Chemical / UV filters | E13 E14 | E15 | E16 E17 | | |

Hydrophobic Agents

SPRAYABLE COMPOSITIONS CONTAINING OIL-IN-WATER EMULSIONS CONTAINING SUBMICRON HYDROPHOBIC AGENTS AND METHODS OF USE THEREOF

CORRESPONDING APPLICATION

This application claims priority to U.S. Provisional Patent Application No. 63/433,660, filed on Dec. 19, 2022, which is incorporated herein in its entirety by reference thereto.

BACKGROUND OF THE DISCLOSURE

1. Field of the Disclosure

This disclosure generally relates to sprayable compositions containing oil-in-water emulsions. The oil-in-water emulsions comprise i) submicron particles of one or more hydrophobic agent(s), (ii) an emulsifier system comprising one or more nonionic surfactant(s) or emulsifier(s), and (iii) an aqueous-solute fluid. The sprayable compositions have a viscosity sufficient to form a spray of preset or desired droplet size upon dispensing from a spray dispenser. The sprayable compositions are useful in pharmaceutical, cosmetic, over-the-counter (OTC) drug, personal care, animal care, veterinary health, and other applications.

2. Discussion of the Background Art

The current practices for combining a hydrophobic material (such as liquid, semi-solid, or solid) with a hydrophilic liquid in a sprayable composition, that is capable of being evacuated in a sprayable form, requires the addition of agents that change the native properties of both the hydrophobic material and the hydrophilic liquids so that they more closely resemble one another. As the properties of the two phases converge because of the additives, they have a greater propensity to be stable for a commercially viable period of time. An important class of additives that can be used in these hydrophobic phase/hydrophilic phase combinations is the surface-active agent, which is typically referred to as a "surfactant". These surfactants have both hydrophobic and hydrophilic properties.

When one or more of these agents are incorporated into the hydrophobic phase, the hydrophilic phase, or both, the agents will align themselves at the hydrophobic phase-hydrophilic phase interface or at the interface between the sprayable composition and the surrounding air. The force/unit length that exists at the hydrophobic phase-hydrophilic phase ("interfacial tension") is reduced, allowing the two phases to more favorably coexist. Similarly, the force/unit length that exists at the air-sprayable composition interface ("surface tension") is also reduced.

A special sub-category of "surfactants" is called an emulsifier. When carefully selected, such emulsifiers have a wide range of surface-active properties. These materials not only lower the interfacial tension at the hydrophobic phase-hydrophilic phase interface but, with the input of shearing energy, they enable the formation of stable micelles of one phase within the other. The resulting product is called an emulsion. In many cases such emulsions are prepared by heating the hydrophobic and hydrophilic phases to a temperature of 70° C. or greater before combining the two phases. The purpose of heating the phases is to ensure that all semi-solid and solid hydrophobic materials used are melted, and that the two phases have a low enough viscosity so the two phases can mix freely. The hydrophobic and hydrophilic phases are typically mixed until they achieve a homogeneous appearance. Thereafter, they are cooled to ensure the formation of appropriately sized micelles, which is usually on average in the 3 to 10 micron range. Such emulsions typically have a homogeneous, opaque, white appearance due to their particle size.

These emulsions present difficulties in that the stability of these emulsions is particularly problematic when the hydrophilic phase contains high levels of the one or more water-miscible solvents. Further, the emulsification of various hydrophobes or combinations requires adjustments to the type and concentration of emulsifiers with each change that upsets the hydrophobic/hydrophilic balance. Additionally, increasing the internal phase of the emulsion will cause the viscosity to increase reducing its ability to be sprayed acceptably. Also, the processing that creates stable emulsions is difficult to scale from the laboratory to production, and they are not amenable to maintaining emulsion stability upon dilution.

SUMMARY OF THE DISCLOSURE

It has been found that sprayable compositions comprising emulsions of (i) submicron particles of one or more hydrophobic agent(s), (ii) a selective emulsifier system comprising one or more nonionic surfactant(s) or emulsifier(s) having a defined hydrophilic-lipophilic balance (HLB), and (iii) an aqueous-solute fluid, when processed with ultra-high energy mixing, are stable for a commercially viable period of time. The emulsions of submicron hydrophobic agents can greatly enhance the aesthetic and therapeutic properties of the sprayable composition. Additionally, the selective emulsifiers can be used regardless of the hydrophobe being emulsified. Further, the emulsions of submicron hydrophobic agents can be easily diluted post-production to deliver the preset or desired level of active or therapeutic agents and the preset or desired aesthetic properties. The sprayable compositions can easily be scaled from the laboratory to production.

This disclosure relates in part to a sprayable composition comprising: an emulsion comprising (i) submicron particles of one or more hydrophobic agent(s), (ii) an emulsifier system comprising one or more nonionic surfactant(s) or emulsifier(s), and (iii) an aqueous-solute fluid. The one or more nonionic surfactant(s) or emulsifier(s) comprise ester(s) of one or more fatty acid moieties with one or more hydroxyl groups of glycerol or polyglycerol (e.g., glyceryl acyloates and polyglyceryl acyloates) having a hydrophilic-lipophilic balance (HLB) from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion. The sprayable composition has a viscosity sufficient to form a spray of preset or desired droplet size upon dispensing from a spray dispenser.

This disclosure also relates in part to a sprayable composition comprising an emulsion. The emulsion comprises (i) submicron particles of one or more hydrophobic agent(s), (ii) an emulsifier system comprising one or more nonionic surfactant(s) or emulsifier(s), and (iii) an aqueous-solute fluid. The submicron particles of one or more hydrophobic agent(s) are present in an amount from about 0.01% wt. to about 70% wt., the aqueous-solute fluid is present in an amount from about 1.0% wt. to about 98.5% wt., and the one or more nonionic surfactant(s) or emulsifier(s) are present in an amount from about 0.01% wt. to about 10% wt., all based on the total weight of the sprayable composition. The submicron particles of one or more hydrophobic agent(s) (i) have an average particle size from about 100 nm to less than about 1000 nm, (ii) have a solubility of less than about 0.1% by weight in water under standard conditions, and (iii) are 85% or more of a size within ±2.0 standard deviations, of the average particle size. The one or more nonionic surfactant(s) or emulsifier(s) comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion. The sprayable composition has a viscosity sufficient to form a spray of preset or desired droplet size upon dispensing from a spray dispenser.

This disclosure further relates in part to a process comprising: preparing a premix comprising (i) one or more hydrophobic agent(s), (ii) an emulsifier system comprising one or more nonionic surfactant(s) or emulsifier(s), (iii) an aqueous-solute fluid, and optionally (iv) one or more additive(s); subjecting the premix to low energy mixing to form a first emulsion; and subjecting the first emulsion to ultra-high energy mixing to form a second emulsion. The second emulsion comprises (i) submicron particles of one or more hydrophobic agent(s), (ii) an emulsifier system comprising one or more nonionic surfactant(s) or emulsifier(s), (iii) an aqueous-solute fluid, and optionally (iv) one or more additives. The one or more nonionic surfactant(s) or emulsifier(s) comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion. The sprayable composition has a viscosity sufficient to form a spray of preset or desired droplet size upon dispensing from a spray dispenser.

This disclosure yet further relates in part to a sprayable composition comprising: an emulsion comprising (i) submicron particles of one or more hydrophobic agent(s), (ii) an emulsifier system comprising one or more nonionic surfactant(s) or emulsifier(s), and (iii) an aqueous-solute fluid. The one or more nonionic surfactant(s) or emulsifier(s) comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion. The sprayable composition is produced by a process comprising: preparing a premix comprising (i) one or more hydrophobic agent(s), (ii) an emulsifier system comprising one or more nonionic surfactant(s) or emulsifier(s), (iii) an aqueous-solute fluid, and optionally (iv) one or more additive(s); subjecting the premix to low energy mixing to form a first emulsion; and subjecting the first emulsion to ultra-high energy mixing to form a second emulsion. The sprayable composition comprises the second emulsion. The sprayable composition has a viscosity sufficient to form a spray of preset or desired droplet size upon dispensing from a spray dispenser.

This disclosure further relates in part to a method of treating disorders of human or animal skin, hair or mucosal tissue. The method comprises applying to the skin, hair or external mucosa of a human or animal a sprayable composition. The sprayable composition comprises: an emulsion comprising (i) submicron particles of one or more hydrophobic agent(s), (ii) an emulsifier system comprising one or more nonionic surfactant(s) or emulsifier(s), and (iii) an aqueous-solute fluid. The one or more hydrophobic agent(s) comprise one or more active or therapeutic agent(s). The one or more nonionic surfactant(s) or emulsifier(s) comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion. The sprayable composition has a viscosity sufficient to form a spray of preset or desired droplet size upon dispensing from a spray dispenser.

This disclosure yet further relates in part to a method of imparting a desirable tactile, olfactory, oral, or visual property to a skin, hair, or mucosal surface of a human or animal, or to a surface or substrate. The method comprises applying to the skin, hair or external mucosa of a human or animal, or to a surface or substrate, the sprayable composition. The sprayable composition comprises: an emulsion comprising (i) submicron particles of one or more hydrophobic agent(s), (ii) an emulsifier system comprising one or more nonionic surfactant(s) or emulsifier(s), and (iii) an aqueous-solute fluid. The one or more hydrophobic agent(s) comprise one or more aesthetic modifying agent(s). The one or more nonionic surfactant(s) or emulsifier(s) comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion.

This disclosure also relates in part to a method of delivering one or more active or therapeutic ingredients to a human or animal. The method comprises providing an emulsion comprising (i) submicron particles of one or more hydrophobic agent(s), (ii) an emulsifier system comprising one or more nonionic surfactant(s) or emulsifier(s), and (iii) an aqueous-solute fluid. The one or more nonionic surfactant(s) or emulsifier(s) comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion. The emulsion acts as a multifunctional delivery vehicle for active or therapeutic ingredients. The method further comprises using the multifunctional delivery vehicle to deliver the one or more active or therapeutic ingredients to a human or animal.

The one or more active or therapeutic ingredients include, for example, anti-acne agents, antimicrobial agents, anti-inflammatory agents, analgesics, anti-erythemal agents, antipruritic agents, antiedemal agents, anti-psoriatic agents, antifungal agents, skin protectants, sunscreen agents, vitamins, antioxidants, anti-irritants, anti-bacterial agents, antiviral agents, antiaging agents, photoprotection agents, exfoliating agents, wound healing agents, sebum modulators, immunomodulators, hormones, botanicals, moisturizing agents, hand sanitizing agents, astringents, sensates, antibiotics, anesthetics, steroids, tissue healing substances, tissue regenerating substances, amino acids, peptides, minerals, ceramides, hyaluronic acids, skin bleaching ingredients, pre-biotics, probiotics, hemp oils, cannabinoids, and any derivatives or combinations thereof.

This disclosure yet further relates in part to a method of using a sprayable composition to enhance a physical, chemical, nutritional and/or sensory property of a food. The method comprises applying an edible sprayable composition into or onto the food. The edible sprayable composition comprises an emulsion comprising (i) submicron particles of one or more edible hydrophobic agent(s), (ii) an emulsifier system comprising one or more edible nonionic surfactants, and (iii) an aqueous-solute fluid. The one or more edible hydrophobic agent(s) comprise one or more edible active or therapeutic agent(s) and/or one or more edible aesthetic modifying agent(s). The one or more edible nonionic surfactants comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion. The submicron particles of the one or more edible hydrophobic agent(s) in the emulsion increase an extent of penetration of the emulsion throughout a water phase of a substrate of the food, thereby producing a bloom effect distributing the submicron particles of the one or more edible hydrophobic agent(s) uniformly throughout the water phase of the substrate that enhances a physical, chemical, nutritional and/or sensory property of the food.

This disclosure also relates in part to a method of using a sprayable composition to enhance a physical, chemical, nutritional and/or sensory property of a beverage. The method comprises applying an edible sprayable composition into the beverage. The edible sprayable composition comprises an emulsion comprising (i) submicron particles of one or more edible hydrophobic agent(s), (ii) an emulsifier system comprising one or more edible nonionic surfactants, and (iii) an aqueous-solute fluid. The one or more edible hydrophobic agent(s) comprise one or more edible active or therapeutic agent(s) and/or one or more edible aesthetic modifying agent(s). The one or more edible nonionic surfactants comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion. The submicron particles of the one or more edible hydrophobic agent(s) in the emulsion increase an extent of penetration of the emulsion throughout a water phase of the beverage, thereby producing a bloom effect distributing the submicron particles of the one or more edible hydrophobic agent(s) uniformly throughout the water phase of the beverage that enhances a physical, chemical, nutritional and/or sensory property of the beverage.

The small average particle size, homogeneity, and force of repulsion of the submicron particles of the hydrophobic agent in the emulsion increases the extent of penetration and accelerates diffusion throughout the water phase of a substrate of the food or beverage, producing a bloom effect that enhances the physical, chemical, nutritional and/or sensory property of a food or beverage.

The emulsions of this disclosure can be applied into or onto a food and/or a beverage to enhance the physical, chemical, nutritional, and/or sensory properties of the food or beverage, and also to prevent freezer burn.

This disclosure further relates in part to a method of enhancing food. The method comprises contacting the food with a sprayable composition. The sprayable composition comprises an emulsion comprising (i) submicron particles of one or more edible hydrophobic agent(s), (ii) an emulsifier system comprising one or more edible nonionic surfactants, and (iii) an aqueous-solute fluid. The one or more edible nonionic surfactants comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion.

The emulsions of this disclosure can be in the form of, or formulated as, a light liquid, a light lotion, a light fluid, a rich fluid, or the like; or, in particular, can be in the form of, or formulated as, a light liquid, an emollient or rich liquid, a light fluid, a rich fluid, a light lotion, a spray, or other comparable forms that have the required rheology to be dispensed as a consumer acceptable spray.

The emulsions of this disclosure can be formulated, for example, as a spray sunscreen, a spray toner, a spray body lotion, a spray body moisturizer, an exfoliating mask, a spray lubricating fluid, and the like.

In an embodiment, the sprayable compositions herein may be a cosmetic sprayable composition, a pharmaceutical sprayable composition, or a cosmeceutical sprayable composition suitable for use on keratinous tissue (e.g., skin, hair, and nails). In some instances, the sprayable composition form may follow from the particular dermatologically acceptable carrier chosen (i.e., an oil-in-water (O/W) emulsion). It may be particularly desirable to provide the present sprayable composition as a sunscreen spray, a skin or hair spray, a spray toner, or essence. Also, the sprayable compositions herein are suitable for use on a variety of surfaces and substrates, including but not limited to, furniture, ingestibles, plants, trees, and the like.

It has been surprisingly found, in accordance with this disclosure, that the preparation of emulsions utilizing a combination of low energy mixing followed by ultra-high energy mixing provides emulsions having enhanced stability. In the process of this disclosure, after undergoing ultra-high energy mixing, the second emulsion exhibits enhanced stability, that is stability for a greater period of time, as compared to stability exhibited by the first emulsion, after undergoing only low energy mixing.

The surprisingly enhanced stability exhibited by the emulsions of this disclosure is attributable to several unique features including, but not limited to, the non-mechanical processing of ultra-high energy mixing, the submicron size of the emulsion hydrophobic particles, the HLB of the nonionic surfactants, the nature of the hydrophobe, the nature of the aqueous-solute fluid, and viscosity/rheology of the rheological modifying agent (if present).

BRIEF DESCRIPTION OF THE DRAWINGS

FIG. 2 shows the product type and hydrophobe for emulsion sprayable compositions of this disclosure, in accordance with the Examples.

DETAILED DESCRIPTION OF THE EMBODIMENTS

Figure 1:
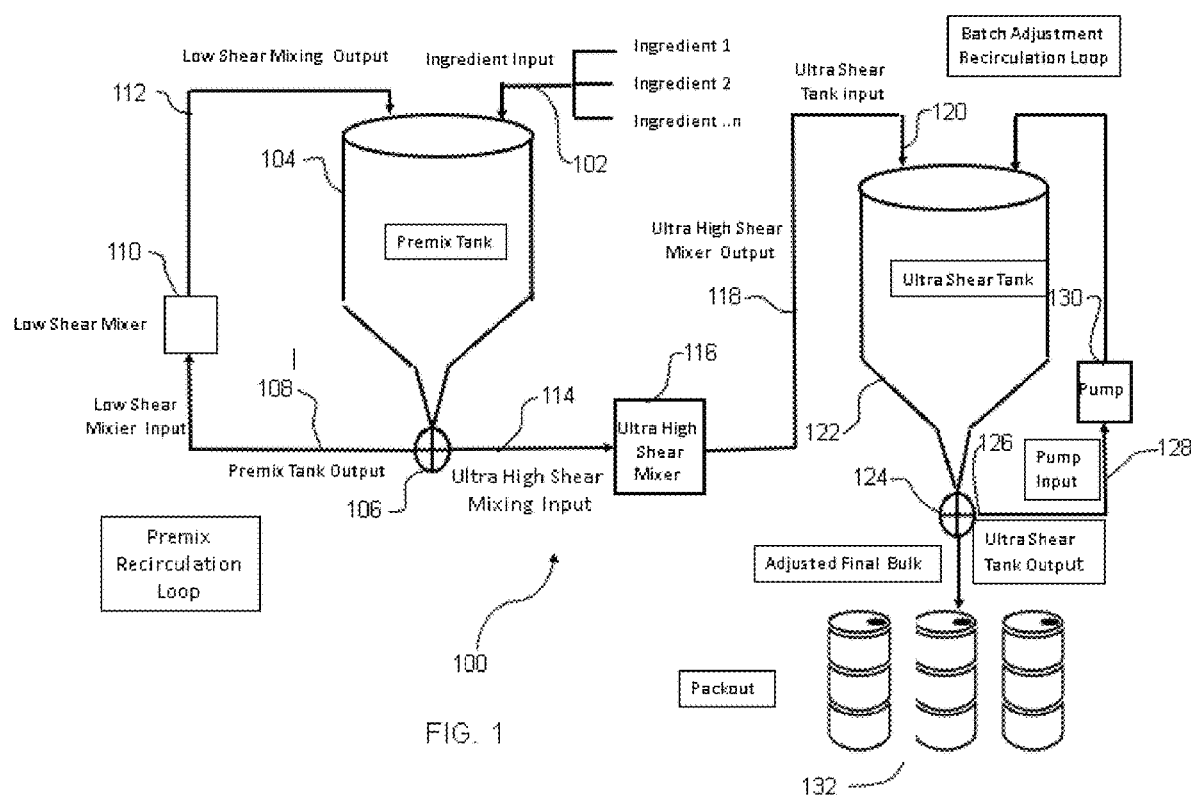
FIG. 1 is an illustrative process flow diagram according to the present disclosure.

The emulsions of submicron particles of one or more hydrophobic agent(s) of this disclosure usefully employ one or more hydrophobic agent(s), an emulsifier system comprising one or more nonionic surfactant(s) or emulsifier(s), and as a solvent, water or a mixture of water and a water miscible solvent, such as ethanol or glycerin. These sprayable compositions can contain, as hydrophobic agents, aesthetic modifying agents that impart a desirable tactile, olfactory, or visual property to an animal (such as a human) skin, hair or mucosal surface to which the sprayable compositions are applied. Further, these sprayable compositions can contain, as hydrophobic agents, active or therapeutic agents that treat disorders of human (or animal) skin, hair or mucosal tissue to which they are applied.

It has been unexpectedly found that sprayable compositions containing emulsions of submicron particles of one or more hydrophobic agent(s), an emulsifier system comprising one or more nonionic surfactant(s) or emulsifier(s), and an aqueous-solute fluid, are stable for a commercially viable period of time. These emulsions of submicron hydrophobic agents can greatly enhance the aesthetic and therapeutic properties of the sprayable composition. Further, these emulsions of submicron hydrophobic agents can be easily diluted in the sprayable composition post-production to deliver the preset or desired level of active or therapeutic agents and the preset or desired aesthetic properties. When the aqueous-solute fluid is described herein, it will be recognized that the aqueous fluid or water miscible solvent can be sourced from a concentrated starting emulsion, or from materials used to dilute such a starting emulsion of submicron particles. The sprayable compositions can easily be scaled from the laboratory to production.

The sprayable compositions can contain hydrophilic aesthetic modifying agents and active or therapeutic agents which are believed to reside in the sprayable composition outside of the emulsion particles of hydrophobic agents.

The sprayable compositions of the present disclosure contain one or more emulsions of submicron particles of one or more hydrophobic agents, and an emulsifier system comprising one or more nonionic surfactant(s) or emulsifier(s), in an aqueous continuous phase. Such emulsions are referred to herein as hydrophobe-in-water emulsions. Oil-in-water emulsions are examples of hydrophobe-in-water emulsions. Hydrophobe-in-water emulsions can also have, for example, silicone or Omega-3-6-9 Fatty Acids as the hydrophobes dispersed in an aqueous continuous phase.

A "hydrophobic agent" according to the disclosure has a solubility of less than about 0.1% by weight in water under standard conditions. Generally, the dielectric constant of the solvent provides a rough measure of a solvent's polarity. The strong polarity of water is indicated, at 20° C., by a dielectric constant of 80.10. Materials with a dielectric constant of less than 15 are generally considered to be nonpolar. In embodiments, the "hydrophobic agent" component(s) are substantially non-polar or insoluble in water, in that 90% wt. or more are non-polar or insoluble in water by this dielectric constant measure. In embodiments, 95% or 99% wt. or more of the hydrophobic agent component(s) are non-polar or insoluble in water.

An "active or therapeutic agent(s)" according to this disclosure is used to treat disorders of human (or animal) skin, hair or mucosal tissue, or to impart a functionality (e.g., cleaning, coloring, fragrancing, styling, and the like), to which the sprayable compositions are applied. As used herein, the term "active or therapeutic agent(s)" includes pharmaceutical therapeutic agent(s).

A "functional agent(s)" according to this disclosure are additives, imparts a functionality (e.g., cleaning, coloring, fragrancing, styling, and the like), to human (or animal) skin, hair or mucosal tissue, or other surfaces and substrates, to which the sprayable compositions are applied. Functional agent(s) include, for example, neutralizing agents, chelating agents, foaming agents, rheological modifying agents, sensates, and the like.

An "aesthetic modifying agent(s)" according to this disclosure imparts a desirable tactile, olfactory, or visual property to an animal (such as a human) skin, hair or mucosal surface, or other surfaces and substrates, to which the sprayable compositions are applied An "emulsifier system" of the current disclosure is one that includes one or more nonionic surfactant(s) or emulsifier(s), namely, one or more ester(s) of one or more fatty acid moieties with one or more hydroxyl groups of glycerol or polyglycerol (e.g., glyceryl acyloates and polyglyceryl acyloates) having a HLB from about 3 to about 20, or from about 7 to about 19, or from about 9 to about 18, or from about 11 to about 17.5, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, or from about 10 to about 17.5, or from about 12 to about 17, or from about 12.5 to about 16, or from about 13 to about 16, based on the degree of glyceryl units or ethoxyl units, or combinations thereof. The emulsifier system comprising nonionic surfactants or emulsifiers is sufficient to stabilize the submicron particles of one or more hydrophobic agent(s) in the emulsions of this disclosure, at a level from about 0.05% w/w to about 70% w/w of said one or more hydrophobic agent(s), in the emulsions.

"Acyloate(s)" according to this disclosure include alkyloates, alkanoates, alkenoates, alkynoates, and aryloates (e.g., benzoates).

"Nonionic surfactant(s) or emulsifier(s)" according to this disclosure include ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. Surfactants adsorb at the interface between oil and water, thereby decreasing the surface tension. An emulsifier is a surfactant that stabilizes emulsions. Emulsifiers coat hydrophobic droplets within an emulsion and prevent them from coming together, or coalescing.

"Miscibility" or "miscible" according to this disclosure refers to the ability of a substance or solute (e.g., ethanol) to mix in all proportions with another substance, fluid or solvent (e.g., water), forming a homogeneous mixture or solution. "Miscibility" or "miscible" is associated with two liquids and indicates that the solvent (e.g., water) and the solute (e.g., ethanol) are soluble with each other at any ratio. As used herein, "miscibility" or "miscible" is included within "solubility" or "soluble".

"Solubility" or "soluble" according to this disclosure refers to the ability of a substance or solute to form a solution with another fluid or solvent (e.g., water), in which the solute has a solubility in the solvent (e.g., water) of 0.1% by weight or greater. "Solubility" or "soluble" is associated with both liquids and solids. As used herein, "solubility" or "soluble" includes "miscibility" or "miscible".

Parameters involved with solubility or the dissolution process include polarity (dielectric constant), temperature, and pressure. Assuming temperature and pressure are constant at standard temperature and pressure, then polarity is a critical parameter. This is typically measured by taking the dielectric constant of the solvent or solution.

The dielectric constant of a solvent is a measure of its polarity. The higher the dielectric constant of a solvent, the more polar it is. Polar solvents dissolve polar solutes and nonpolar solvents dissolve nonpolar solutes. The dielectric constant of a solvent can help predict how well a solute molecule will dissolve in it.

The polarity of a solute is determined by the presence of polar functional groups such as hydroxyl (—OH), carbonyl (>C=O), and amino (—NH2) groups. The polarity of a solvent is determined by its dielectric constant. A substance with a high dielectric constant is easily polarized, allowing countercharges to be placed around an ion, resulting in Coulombic interactions between solvent and ion, promoting solubilization of the ion by competing with interionic interactions.

The polarity and dielectric constant of both the solvent and solute play an important role in determining solubility. Polar solvents dissolve polar solutes and nonpolar solvents dissolve nonpolar solutes. The higher the dielectric constant of a solvent, the more polar it is, which promotes Coulombic interactions between solvent and ion, promoting solubilization of the ion by competing with interionic interactions.

An "aqueous-solute fluid" according to the disclosure can be water or a combination of water and one or more materials or solutes that have a solubility in water of 0.1% by weight or greater. As used herein, "aqueous-solute fluid" includes "polar solute", "water miscible liquid or solute", "water soluble liquid or solute", and "water soluble solid or solute".

A "polar solute" of the current disclosure is one that has a solubility in water of 0.1% by weight or greater. As used herein "polar solute" includes "water miscible solute", and "water soluble solute".

A "water miscible liquid or solute" of the current disclosure is one that can mix in all proportions with water, forming a homogeneous solution.

A "water soluble solid or solute" according to the disclosure is one or more materials or solutes that are solid at a temperature of 23° C. and a pressure of 100 kPa (1 bar), and have a solubility in water of 0.1% by weight or greater. For the solid solutes, the solubility product constant (Ksp) is used to represent the level at which a solute dissolves in solution. Ksp is the equilibrium constant for a solid substance dissolving in an aqueous solution. The more soluble a substance is, the higher the Ksp value it has. As used herein, Ksp is determined at a temperature of 23° C. and a pressure of 100 kPa (1 bar).

A "water soluble liquid or solute" according to the disclosure is one or more materials or solutes that are liquid at a temperature of 23° C. and a pressure of 100 kPa (1 bar), and have a solubility in water of 0.1% by weight or greater. The water soluble liquids or solutes are flowable, non-viscous, semi-viscous, or viscous liquids, at a temperature of 23° C. and a pressure of 100 kPa (1 bar).

An "aqueous fluid" according to the disclosure can be water or a combination of 50% or more water and from 0 to 50% solutes other than water miscible solutes.

"Hydrophobic agent particles" are colloidal droplets of hydrophobic agent(s), wherein at some temperature in the range of 20 to 90° C. the droplets would be liquid. A colloid is a substance microscopically dispersed throughout another substance. A colloidal system consists of two separate phases: a dispersed phase (or internal phase) and a continuous phase (or dispersion medium) in which the colloid is dispersed.

A "submicron hydrophobic emulsion" is defined as a submicron suspension of hydrophobic agent particles in an aqueous fluid or an aqueous-solute fluid with an average particle size of from 100 nm to 999 nm. In embodiments of the disclosure, 85% or more, or 90% or more, of the hydrophobic agent particles by weight have a size within ±2.0 standard deviations, or within ±1.9 standard deviations, or within ±1.8 standard deviations, or within ±1.7 standard deviations, or within ±1.6 standard deviations, of the average particle size. The hydrophobic agent particles are not included in the water-solvent-solute weight percentages. The emulsion of submicron hydrophobic agent particles can be reduced by the processes described herein, or as concentrated therefrom, or diluted therefrom.

To treat indications with an active or therapeutic agent or functional agent, an "effective amount" of an active or therapeutic agent or functional agent will be recognized by clinicians but includes an amount effective to treat, reduce, alleviate, ameliorate, eliminate or prevent one or more symptoms of the condition sought to be treated, or alternately, the condition sought to be avoided, or to otherwise produce a clinically recognizable favorable change in the condition or its effects.

An "emulsion" as used herein means, a suspension of submicron hydrophobic agent particles, in an aqueous fluid or an aqueous-solute fluid, with nonionic surfactant(s).

"HLB" as used herein means, a hydrophilic-lipophilic balance. HLB is the balance of the size and strength of the hydrophilic and lipophilic moieties of a surfactant molecule.

"Emulsion stability", and variations thereof, refer to the ability of an emulsion to resist change in its properties over time. The changes may be physical or chemical and may be visible or invisible. For example, a lack of emulsion stability may manifest as a visible phase separation (i.e., creaming or sedimentation). In another example, emulsion instability may manifest as an invisible (to the human eye) coalescence of the droplets in the dispersed phase that results in a change in viscosity or flow properties. Microfluidization or ultra-high energy processing, or the submicron size of the emulsion hydrophobic particles, together with the HLB of the nonionic surfactants, the nature of the hydrophobe, the nature of the aqueous-solute fluid, and viscosity/rheology of the rheological modifying agent (if present), are important for imparting commercially viable emulsion stability.

An "agent" as used in this application, is a substance that brings about a chemical or physical effect or causes a chemical reaction.

A "hydrophobe" or "hydrophobic agent," as used in this application, is a molecule or compound that is repelled by or has no attraction to water and hydrophobe has little or no solubility in water, for example less than 0.1%, less than 0.05%, or less than 0.03%. Examples include oils, alkanes, and esters of fatty acids.

An "edible" material according to this disclosure is one that is generally recognized as safe for human or animal consumption.

The emulsions of submicron hydrophobic agent particles of this disclosure can be "contacted" with food products. The meaning of "contacted" will be understood by those of skill in the art, and includes being applied onto or into the food substrate using any commercially viable process.

"Food(s)" according to this disclosure is any food generally recognized for human or animal consumption including, but not limited to, meats such as chicken, turkey, beef, buffalo, pork, lamb, goat, fish, scallops, other seafood, or the like; beverages; processed foods; hydratable foods such as pastas, rice, other grains, dried fruits or vegetables (such as dried beans), drink concentrates, or the like; milk or milk substitutes; soups, sauces; grain flour; and the like.

"Sensate(s)" according to this disclosure are substances that impart a sensation to the mucous membranes, oral cavity, throat, or skin. These substances may be used as flavors or fragrances in a wide range of products such as personal care products (perfumes, deodorants, cosmetics, shampoos, skin creams, toothpastes, and the like), pharmaceuticals (such as cough syrups, cough drops and the like), and foods (such as chewing gum, soda, and the like). The sensation can be, for example, a cooling effect, a warming effect, a tingling effect, an emollient effect, and any derivatives or combinations thereof.

"Pre-biotics" according to this disclosure are materials that can be ingested into the stomach to selectively support the growth of beneficial bacteria while reducing the ability of pathogenic bacteria to grow. These pre-biotic materials that favor the proliferation of beneficial bacteria at the expense of pathogenic microorganisms are beneficial for the maintenance of a protective barrier, proper metabolism, and maintenance of good health of the body including the skin.

"Standard condition(s)" according to this disclosure are ambient conditions, or a temperature of 23° C. and a pressure of 100 kPa (1 bar).

Process

In accordance with the process of this disclosure, a premix is prepared comprising (i) one or more hydrophobic agent(s), (ii) an aqueous-solute fluid, (iii) one or more nonionic surfactant(s) or emulsifier(s), and optionally (iv) one or more additive(s). The premix is subjected to low energy mixing to form a first emulsion. The first emulsion is then subjected to ultra-high energy mixing to form a second emulsion. The second emulsion comprises submicron particles of one or more hydrophobic agent(s), emulsified or dispersed in an aqueous-solute fluid, and one or more nonionic surfactant(s) or emulsifier(s). The one or more nonionic surfactant(s) or emulsifier(s) comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof. The one or more nonionic surfactant(s) or emulsifier(s) are sufficient to stabilize the submicron particles of one or more hydrophobic agent(s) in the second emulsion, at a level from about 0.05% w/w to about 70% w/w of said one or more hydrophobic agent(s), in the second emulsion.

As discussed herein, the emulsions of the present disclosure can be produced by a combination of low energy mixing and ultra-high energy mixing (e.g., high-pressure high-shear homogenization). It has been unexpectedly found by the present disclosure that the initial particle size obtained by low energy mixing, prior to ultra-high energy mixing is, in part, critical to achieving the stability of the combined continuous phase with the emulsions, together with the nonionic surfactants, in the fewest number of passes.

Each material has a terminal particle size achievable by ultra-high energy mixing. The terminal particle size varies based on the material. In an exemplary embodiment, prior to ultra-high energy mixing to create the emulsions of the present disclosure, an initial average particle size of the raw material components for the emulsion is on the order of several microns.

After ultra-high energy mixing, an average particle size of the components of the emulsion can be, about 200 nm, about 205 nm, about 210 nm, about 215 nm, about 220 nm, about 225 nm, about 250 nm, about 275 nm, about 300 nm, about 325 nm, about 350 nm, about 375 nm, about 400 nm, about 425 nm, about 450 nm, about 475 nm, about 480 nm, about 500 nm, about 525 nm, about 550 nm, about 575 nm, 600 nm, about 625 nm, about 650 nm, about 675 nm, about 700 nm, about 725 nm, about 750 nm, about 800 nm, about 900 nm, and any ranges or subranges between any of the foregoing and including endpoints.

In an embodiment, after ultra-high energy mixing, the average particle size of the hydrophobic agent components in the emulsion can range from about 100 nm to about 999 nm, or from about 125 nm to about 900 nm, or from about 150 nm to about 800 nm, or from about 175 nm to about 750 nm, or from about 200 nm to about 700 nm, or from about 250 nm to about 600 nm.

As used herein, "low energy mixing" refers to low shear mixing in which the mixing is mechanical. Size of particles produced limited to the mechanical equipment tolerances unless significant amounts of emulsifier/surfactant are used. Illustrative mechanical equipment useful for low energy mixing includes, but not limited to, side-sweep mixing, counter-rotational mixing oars, propeller/fixed shaft+ attached mixing head (prop/paddle/saw-tooth/etc.), media mills (sand, beads, etc.), roller mills (physical rollers that can be moved closer/further from one another), homogenizer (rotor-stator set-up with variable/interchangeable stators-large holes, medium holes, small holes, slotted, square holes of variable size, diamond shaped), and the like.

As used herein, "ultra-high energy mixing" refers to ultra-high shear mixing in which the mixing is non-mechanical. Illustrative non-mechanical equipment useful for ultra-high energy mixing includes, but not limited to, microfluidizer, sonicator, and the like. A microfluidizer relies on pressure/volume (up to 30,000 psi), impingement of two fluid streams colliding with each other, forced through fixed geometry chambers with entry orifice of a larger size than the exit orifice to allow for particle expansion and diffuse distribution upon exit of chamber, discrete processing capability allows for uniform particles sizes and tight particle distributions. A microfluidizer is highly reproducible. Sonication relies on a probe/horn that translates electrical current into vibrational energy (ultrasonic waves), difficult to achieve overall homogeneity of particles produced and generally produces multiple particle size peaks, difficulties with reproducibility of particle size and distributions curves.

Referring to FIG. 1, in an example, the emulsions can be created by an emulsification process 100 that uses multi-step mixing, namely low energy mixing followed by ultra-high energy mixing.

The ingredients for the emulsion are fed into a premix tank 104 via ingredient input 102. The ingredients include water, or water and one or more miscible solvents, one or more nonionic surfactant(s) or emulsifier(s), one or more hydrophobes, and optionally other additives. The premix tank 104 has a valve 106 for directing the premix tank output 108 to a low shear mixer 110, or for directing an ultra-high shear mixing input 114 to an ultra-high shear mixer 116. The premix tank output 108 is mixed with the low shear mixer 110 to a preset or desired particle size, to produce a low shear mixing output 112, which is returned to the premix tank 104 for holding or until ready for ultra-high shear mixing. This constitutes a premix recirculation loop. Non-limiting examples of the low shear mixer 110 include, for example, propeller mixing, pump recirculation, rotor stator homogenization, media mills, and colloid mills.

In examples, a mixture of water, or water and one or more miscible solvents, one or more nonionic surfactant(s) or emulsifier(s), one or more hydrophobes, and optionally one or more additives, are low energy mixed until an average particle size of the hydrophobes in the mixture is optimally less than 150 microns to yield a premix tank output 108 or a first emulsion. Mixing by low shear mixer 110 is mechanical and is performed at ambient pressure and temperature. Mixing is performed until an average particle size of the hydrophobes in the mixture is less than 150 microns, less than 100 microns, less than 80 microns, less than 50 microns, less than 40 microns, less than 30 microns, less than 25 microns, preferably less than 20 microns, more preferably less than 12 microns, still more preferably less than 10 microns, and most preferably less than 8 microns. Surprisingly, such low energy mechanical mixing prior to ultra-high energy mixing achieves optimal hydrophobe-in-water emulsions.

As described above, the premix tank 104 has a valve 106 for directing the ultra-high shear mixing input 114 to a fluidizer or ultra-high shear mixer 116. The ultra-high shear mixing input 114 is mixed with the ultra-high shear mixer 116 to a preset or desired particle size, to produce an ultra-high shear mixer output 118, which is fed, as ultra-shear tank input 120, to an ultra-shear tank 122 for holding, reworking, or until ready for packaging. The ultra-high shear mixer 116 can have a heat exchanger (not shown) to maintain temperature of the ultra-high shear mixer output 118. Non-limiting examples of ultra-high shear mixer 116 include, for example, high-pressure and high-shear devices, sonication, and the like.

The ultra-shear tank 122 has a valve 124 for directing the ultra-shear tank output 126 to packout as final bulk 132 or to a pump 130 through pump input 128. The pump output is returned to the ultra-shear tank 122 for holding, further reworking, or until ready for packaging. This constitutes a batch adjustment recirculation loop.

The heat exchanger maintains temperatures in ultra-high shear mixer 116 below 35 C°, preferably below 32 C°, more preferably below 29 C°, and most preferably below 27 C°.

The pressure in ultra-high shear mixer 116 can be from about 6,000 to about 31,000 psi, preferably from about 11,000 to about 24,000 psi, and more preferably from about 13,000 to about 19,000 psi. The throughput decreases as pressure increases.

In one example, the emulsions are produced by a combination of shear forces, impact forces, and energy dissipation forces.

Shear forces are unaligned forces that pushing a portion of the particle body in one specific direction, and another portion the particle body in the opposite direction. Thereby, the particles are caused to fracture and be broken up into smaller particles.

Impact forces occur when two particles collide with each other or with another object/body. Non-homogeneous particles result in inelastic collisions. Conversely, homogeneous particles result in elastic collisions and a more uniform final particle size. High velocity collisions between the particles cause the particles to exhibit a brittle behavior causing them to fracture and be broken up into smaller particles.

Dissipation forces increase the entropy of the system. Viscous forces, for example are the force that act on the particles in the direction in which the particles are moving relative to other particles and hence opposite to the direction in which the particles are moving relative to each other.

In an exemplary embodiment, emulsification process 100 will produce an emulsion of submicron particles of the one or more hydrophobic agent(s), in which at least 79 wt % of the total hydrophobic particles in the emulsion are ±500 nm of the value for the average particle size, more preferably are ±400 nm, and still more preferably are ±300 nm, ±200 nm, and ±100 nm, respectively, of the value for the average particle size.

In exemplary embodiments, at least 79 wt % of the total hydrophobic particles in the emulsion are ±2.0 standard deviations, or ±1.9 standard deviations, or ±1.8 standard deviations, or ±1.7 standard deviations, or ±1.6 standard deviations, or ±1.5 standard deviations, of the value for the average particle size.

In exemplary embodiments, emulsification process 100 of the present disclosure will produce a suspension of submicron particles of the one or more hydrophobic agent(s) in which at least 85 wt % of the total hydrophobic particles in the emulsion are ±500 nm of the value for the average particle size, more preferably are ±400 nm, and still more preferably are ±300 nm, ±200 nm, and ±100 nm, respectively, of the value for the average particle size.

In exemplary embodiments, at least 85 wt % of the total hydrophobic particles in the emulsion are ±2.0 standard deviations, or ±1.9 standard deviations, or ±1.8 standard deviations, or ±1.7 standard deviations, or ±1.6 standard deviations, or ±1.5 standard deviations, of the value for the average particle size.

In exemplary embodiments, emulsification process 100 of the present disclosure will produce a suspension of submicron particles of the one or more hydrophobic agent(s) in which at least 87 wt % of the total hydrophobic particles in the emulsion are ±500 nm of the value for the average particle size, more preferably are ±400 nm, and still more preferably are ±300 nm, ±200 nm, and ±100 nm, respectively, of the value for the average particle size.

In exemplary embodiments, at least 87 wt % of the total hydrophobic particles in the emulsion are ±2.0 standard deviations, or ±1.9 standard deviations, or ±1.8 standard deviations, or ±1.7 standard deviations, or ±1.6 standard deviations, or ±1.5 standard deviations, of the value for the average particle size.

In exemplary embodiments, emulsification process 100 of the present disclosure will produce a suspension of submicron particles of the one or more hydrophobic agent(s) in which at least 90 wt % of the total hydrophobic particles in the emulsion are ±500 nm of the value for the average particle size, more preferably are ±400 nm, and still more preferably are ±300 nm, ±200 nm, and ±100 nm, respectively, of the value for the average particle size.

In exemplary embodiments, at least 90 wt % of the total hydrophobic particles in the emulsion are ±2.0 standard deviations, or ±1.9 standard deviations, or ±1.8 standard deviations, or ±1.7 standard deviations, or ±1.6 standard deviations, or ±1.5 standard deviations, of the value for the average particle size.

In exemplary embodiments, emulsification process 100 of the present disclosure will produce a suspension of submicron particles of the one or more hydrophobic agent(s) in which at least 93 wt % of the total hydrophobic particles in the emulsion are ±500 nm of the value for the average particle size, more preferably are ±400 nm, and still more preferably are ±300 nm, ±200 nm, and ±100 nm, respectively, of the value for the average particle size.

In exemplary embodiments, at least 93 wt % of the total hydrophobic particles in the emulsion are ±2.0 standard deviations, or ±1.9 standard deviations, or ±1.8 standard deviations, or ±1.7 standard deviations, or ±1.6 standard deviations, or ±1.5 standard deviations, of the value for the average particle size.

In exemplary embodiments, emulsification process 100 of the present disclosure will produce a suspension of submicron particles of the one or more hydrophobic agent(s) in which at least 95 wt % of the total hydrophobic particles in the emulsion are ±500 nm of the value for the average particle size, more preferably are ±400 nm, and still more preferably are ±300 nm, ±200 nm, and ±100 nm, respectively, of the value for the average particle size.

In exemplary embodiments, at least 95 wt % of the total hydrophobic particles in the emulsion are ±2.0 standard deviations, or ±1.9 standard deviations, or ±1.8 standard deviations, or ±1.7 standard deviations, or ±1.6 standard deviations, or ±1.5 standard deviations, of the value for the average particle size.

In exemplary embodiments, emulsification process 100 of the present disclosure will produce a suspension of submicron particles of the one or more hydrophobic agent(s) in which at least 98 wt % of the total hydrophobic particles in the emulsion are ±500 nm of the value for the average particle size, more preferably are ±400 nm, and still more preferably are ±300 nm, ±200 nm, and ±100 nm, respectively, of the value for the average particle size.

Emulsification process 100 according to the present disclosure can impart a net negative charge on the particles of the emulsion. The absolute value of the negative charge can be at least −15 mV, or −32 mV, or −35 mV or greater.

The emulsions of the disclosure may be produced by mixing an aqueous fluid, nonionic surfactants, and hydrophobic agents using low energy mixing followed by processing conditions known in the art including, but not limited to, sonication (Sonic Man, Matrical Bioscience, Spokane, WA), high pressure/high shear (e.g., utilizing Microfluidizer, Microfluidics Company, Newton, Massachusetts), freeze drying (Biochima Biophys Acta 1061:297-303 (1991)), reverse phase evaporation (Microencapsulation 16:251-256 (1999)), and bubble method (J Pharm Sci 83(3): 276-280).

In sonication, for example, high intensity sound waves bombard the product for predetermined period of time. In direct sonication, the sonication probe is directly applied into the composition for processing. In indirect sonication, the composition is immersed into an ultrasonic bath, where it is exposed to the processing conditions for a predetermined period of time.

Precipitation utilizes compounds that are poorly soluble in water, but soluble in organic solvents and surfactants that are water-soluble, to create emulsions. Two separate solutions are formed, one of an organic solvent and compounds, the other a mixture of surfactant dissolved in water.

The two solutions are combined and an emulsion is created. The organic solvent is then evaporated out of the emulsion, causing the small spherical particles to precipitate, creating a suspension of submicron particles.

High pressure/high shear utilizes an aqueous phase and a hydrophobic phase. The aqueous phase is prepared into a solution with any other water-soluble agents. Further, water miscible solvents are optionally added to create an aqueous-solute phase. The hydrophobic phase is prepared into a mixture with any other non-water miscible or non-water soluble components. The two phases are subjected to pressure ranging from 10,000-50,000 psi. The resulting emulsion contains suspended submicron particles of hydrophobic agents, together with nonionic surfactants.

In freeze drying, two available methods are thin film freezing and spray freeze drying. In spray freeze drying, for example, an aqueous solution containing active or therapeutic ingredients is atomized into the cold gas above a cryogenic liquid. The atomized particles adsorb onto the gas-liquid interface and aggregate there as submicron particles.

The production process is adapted to obtain hydrophobic particles of the appropriate size. The particles of the emulsion of the disclosure are believed to be stable primarily due to small size, together with surfactant effects. This stability enhancement is defined by Stokes' Law which is illustrated in an equation relating the terminal settling or rising velocity of a smooth sphere in a viscous fluid of known density and viscosity to the diameter of the sphere when subjected to a known force field. This equation is $V=(2\ gr^2)(d1-d2)/9\mu$, where V=velocity of fall (cm/sec), g=acceleration of gravity (cm/sec$^2$), r=radius of particle (cm), d1=density of particle (g/cm$^3$), d2=density of medium (g/cm$^3$), and $\mu$=viscosity of the medium (dyne sec/cm$^2$). Using this equation, with all other factors being constant, a 200 nm hydrophobic agent particle has a velocity of fall that is 680 times slower than one of identical ingredient composition having a 5 micron particle size of a standard emulsion.

The emulsion of submicron particles of hydrophobic agents can be created by mixing the hydrophobic agents with nonionic surfactants, an aqueous fluid or an aqueous-solute fluid. The precursor form is generally of higher concentration of hydrophobic agent, and can be, without limitation, diluted with a mixture of solvent, water, and optionally a rheological modifying agent.

The emulsion may be produced with a shear that creates in combination with pressure an average particle size of between about 100 nm to about 999 nm, such as between about 100-500 nm, or 150-500 nm. The process can, for example, without limitation, include a rapid return to atmospheric pressure. Embodiments include wherein 85% or more, or 90% or more, of the particles by weight or, in other embodiments, by volume, are within one of the above-cited ranges.

Size distribution for an emulsion can be measured by a Nanotrac particle size analyzer (Microtrac, Montgomeryville, PA), or a Malvern ZetaSizer particle size analyzer (Malvern Instruments Ltd. Malvern, UK). Sizes recited herein are those determined by dynamic light scattering for spectrum analysis of Doppler shifts under Brownian Motion. Measurements are made using Mie scattering calculations for spherical particles. This reproducible methodology can be conducted with other available instruments for measuring average particle size and particle size distribution, including instruments from Horiba Scientific (Edison, NJ).

The temperature of operation used to produce the emulsion of submicron particles of hydrophobic agents is generally between about 15° C. and about 30° C. In certain embodiments, the process avoids temperatures in excess of about 50° C., or in excess of about 60° C. However certain embodiments may require a temperature exceeding 60° C. to melt the hydrophobic agent.

Without wishing to be bound by a single theory, it is believed that the non-mechanical processing, together with the submicron size of the emulsion hydrophobic particles, the HLB of the nonionic surfactants, the nature of the hydrophobe, the nature of the aqueous-solute fluid, and viscosity/rheology of the rheological modifying agent (if present), are important for imparting emulsion stability. The emulsions offer manufacturing flexibility because the processing makes them compatible with a wide variety of sprayable compositions.

The emulsions of the present disclosure are produced by both a mechanical and non-mechanical process that imparts a small and substantially homogeneous submicron particle size to each particle of a hydrophobic agent.

An emulsion of one or more hydrophobic agent(s) used in the present disclosure can possess a net negative charge after non-mechanical processing, such as by high-pressure high-shear processing. In one example, the absolute value of the negative charge can be at least −30 mV. In another example, my, the absolute value of the negative charge can be at least 32 mV. In yet another example, my, the absolute value of the negative charge can be at least 35 mV or greater.

Preferred methods of non-mechanical processing impart a slight repulsive force that causes the particles of the one or more hydrophobic agent(s) to repel or move away from each other in the emulsion, thus enhancing the stability and dispersibility of the emulsion.

The sprayable compositions and emulsions are prepared under ambient temperatures. Processing can be below 50° C., below 45° C., below 40° C. and below 30° C.

The emulsion used in the present disclosure can be non-mechanically processed until most or all particles of the hydrophobic agent(s) are sufficiently small and essentially monodispersed to be on the side of a dispersity barrier, where a sufficient quantity of the particles are at their smallest size (critical or terminal particle size) to minimize the risk of sedimentation or creaming, and to make the emulsion stable for commercial applications.

The dispersity barrier is a different value for each hydrophobic agent and depends on the physical and chemical properties of the hydrophobic agent. The particles can also possess a net negative charge which repulse one another. The stability of the emulsion and the diffusion of the hydrophobic agent(s) throughout the aqueous continuous phase can be further enhanced when a sufficient number of particles exceed the electrostatic barrier where the magnitude of the charge creates a force of repulsion that is greater than the force on the particles to coalesce. The more particles of hydrophobic agent that exceed both the dispersity barrier and the electrostatic barrier, the greater the stability of the emulsion.

Emulsions

The particles of the emulsions of the present disclosure can have a net negative charge so that the particles exhibit an anti-coalescent tendency. Each particle can be acted upon by a repulsive force from each surrounding particle in a 3-dimensional space or volume such as the base or initial sprayable composition.

The portion (or alternatively, the ratio) of particles that are "over" the electrostatic barrier (i.e. the point at which repulsion forces exceed the coalescing forces in the emulsion), in relation to the total number of particles, can be a measure of the stability and quality of the emulsion. The electrostatic barrier can have a different value for each hydrophobic agent and depends on the physical and chemical properties of the hydrophobic agent. However, the value of the electrostatic barrier for hydrophobic agents can fall within the same range. In addition, in some instances the value of the electrostatic barrier for a hydrophobic agent can be moved somewhat by the selection of processing conditions.

In an exemplary embodiment, at least 20 wt % of the total hydrophobic particles in the emulsion can be over the electrostatic barrier (meaning that repulsion forces exceed coalescing forces for 20 wt % of the particles), indicating that the emulsion is stable. In another preferred embodiment, 50 wt % or more of the particles can be over the electrostatic barrier, indicating that the emulsion is more stable relative to the earlier embodiment. In a preferred embodiment, 75 wt % or more of the particles can be over the electrostatic barrier, indicating that the emulsion is even more stable. In increasingly preferred embodiments, 87 wt % or more, 90 wt % or more, 95 wt % or more, and 97 wt % or more of the particles of the hydrophobic agent can be over the electrostatic barrier, respectively, indicating emulsions that are increasingly stable.

The emulsions of one or more hydrophobic agent(s) of the present disclosure can possess a net negative charge after non-mechanical processing, such as by high-pressure high-shear processing. In one example, the absolute value of the negative charge can be at least −30 mV. In another example, my, the absolute value of the negative charge can be at least −32 mV. In yet another example, my, the absolute value of the negative charge can be at least −35 mV or greater.

The particle sizes in the emulsions according to the present disclosure are maintained above 100 nm by emulsification process 100 so that the average particle size is greater than 100 nm, preferably 120 nm.

Emulsions having an average particle size that is greater than 100 nm have the additional benefit of being regulatory compliant with guidelines that define nanotechnology as particles with an average particle size of less than 100 nm, i.e. that are smaller than the low end of the particle size range of the present disclosure.

The emulsions of the present disclosure containing submicron particles of one or more hydrophobic agent, can be stored in a concentrated form prior to use, such as about 30 wt % to about 70 wt %. Advantageously, the concentrated emulsion can be diluted nearer to the time when it is added to the base or initial sprayable composition. For example, the concentrate can be diluted 1.5-fold, 2-fold, 5-fold, 10-fold, 50-fold, 100-fold, 200-fold, and even 1000-fold.

Dilution of the concentrate to the preset or desired concentration can be used to optimize the benefits of the emulsion for various applications (e.g., nutritional, pharmaceutical, biomedical, over-the-counter (OTC) drug, cosmetic, food, personal care, animal care, household, pet care, veterinary health, and the like). The emulsions of this disclosure can be edible emulsions.

Advantageously, the first (or second, third, etc.) emulsion can be diluted to a preset or desired concentration without upsetting stability, namely without causing flocculation, Ostwald ripening, sedimentation, coalescence, creaming, and phase inversion.

The method can also include preparing a second emulsion. The second emulsion of submicron hydrophobic agents, can be mixed into the first emulsion of submicron hydrophobic agents, prior adding to the base or initial sprayable composition. Alternatively, the first and second emulsions can be added directly to the base or initial sprayable composition.

Advantageously, the first (or second, third, etc.) emulsion can be mixed in various ratios without upsetting stability, namely without causing flocculation, Ostwald ripening, sedimentation, coalescence, creaming, and phase inversion.

Subjecting the mixture of components to be emulsified to one or more preparatory steps, such as low energy mixing in low shear mixer 110, can facilitate increasing the number of elastic collisions in ultra-high energy mixing in ultra-high shear mixer 116 so that the particles of the hydrophobic agent are approximately the same size and mass before high-pressure high-shearing, and their elastic collision produces particles that are smaller but remain approximately equal to each other in size and mass. The resulting particles are then analyzed for particle size, degree of monodispersity, and magnitude of the electrostatic charge. The preset or desired properties of the particles in the emulsion are thus attained more quickly, and with less fuel, less energy, and less cost than conventional techniques, and so manufacturing is more commercially viable.

In accordance with this disclosure, a period of time for stability can be at least one month, or at least two months, or at least three months, or at least six months, or at least one year, and longer, and ranges therebetween, under standard conditions.

A commercially viable period of time for stability according to the present disclosure can be 28 days, one month, two months, three months, six months, one year, and longer, and ranges therebetween, under standard conditions.

It is the submicron size of the emulsion hydrophobic particles, together with the HLB of the nonionic surfactants, the nature of the hydrophobe, the nature of the aqueous-solute fluid, and viscosity/rheology of the rheological modifying agent (if present), that are important for imparting emulsion stability. The small size minimizes the tendency of hydrophobic particles to coalesce. The commercially viable stability described above, allows a useful amount of time in which to store the emulsion or sprayable compositions to maintain product integrity.

The stability is further manifested in that two or more distinct emulsions of this disclosure can be mixed without decreasing the stability of the various component hydrophobic agent particles, or an emulsion can be diluted into aqueous fluid or aqueous-solute fluid without decreasing the stability of the component hydrophobic agent particles.

In the emulsions of the present disclosure, the hydrophobic agent(s) are sufficiently small and monodispersed to be on the side of a dispersity barrier, where a sufficient quantity of the particles are at their smallest size (critical or terminal particle size) to minimize the risk of sedimentation or creaming, and to make the emulsion stable for commercial applications. The dispersity barrier is a different value for each hydrophobic agent and depends on the physical and chemical properties of the hydrophobic agent. The particles can also possess a net negative charge which repulse one another. As described above, the stability of the emulsion and the diffusion of the hydrophobic agent(s) throughout the aqueous continuous phase can be further enhanced when a sufficient number of particles exceed the electrostatic barrier where the magnitude of the charge creates a force of repulsion that is greater than the force on the particles to coalesce. The more particles of hydrophobic agent that exceed both the dispersity barrier and the electrostatic barrier, the greater can be the stability of the emulsion.

Hydrophobic Agents

Examples of hydrophobic agents include but are not limited to, mono, di, tri, or poly alkyl (or alkenyl) esters or ethers of a di-, tri-, or polyhydroxy compound, such as glycerin, sorbitol or other polyol compound. Examples of such esters or ethers include but are not limited to, saturated and unsaturated, linear and branched vegetable oils, such a soybean oil, almond oil, castor oil, canola oil, cottonseed oil, grapeseed oil, rice bran oil, palm oil, coconut oil, palm kernel oil, olive oil, linseed oil, sunflower oil, safflower oil, peanut oil and corn oil. Useful saturated and unsaturated oils include those having 90% or more (molar) fatty acyl components with 6 to 30 carbon atoms, such as 6 to 24 carbons, or 12 to 24 carbons.

Examples of fatty acids providing fatty acyl components, or which provide hydrophobic agents include, without limitation, for example (from www.scientificpsychic.com/fitness/fattyacids.html):

TABLE A

| Common Name | Carbon Atoms | Double | Scientific Name | Sources |
|---|---|---|---|---|
| Common Fatty Acids | | | | |
| Butyric acid | 4 | 0 | butanoic acid | butterfat |
| Caproic Acid | 6 | 0 | hexanoic acid | butterfat |
| Caprylic Acid | 8 | 0 | octanoic acid | coconut oil |
| Capric Acid | 10 | 0 | decanoic acid | coconut oil |
| Lauric Acid | 12 | 0 | dodecanoic acid | coconut oil |
| Myristic Acid | 14 | 0 | tetradecanoic acid | palm kernel oil |
| Palmitic Acid | 16 | 0 | hexadecanoic acid | palm oil |
| Palmitoleic Acid | 16 | 1 | 9-hexadecenoic acid | animal fats |

TABLE A-continued

| Common Name | Carbon Atoms | Double | Scientific Name | Sources |
|---|---|---|---|---|
| Common Fatty Acids | | | | |
| Stearic Acid | 18 | 0 | octadecanoic acid | animal fats |
| Oleic Acid | 18 | 1 | 9-octadecenoic acid | olive oil |
| Ricinoleic acid | 18 | 1 | 12-hydroxy-9-octadecenoic acid | castor oil |
| Vaccenic Acid | 18 | 1 | 11-octadecenoic acid | butterfat |
| Linoleic Acid | 18 | 2 | 9,12-octadecadienoic acid | grape seed oil |
| Alpha-Linolenic Acid (ALA) | 18 | 3 | 9,12,15-octadecatrienoic acid | flaxseed (linseed) oil |
| Gamma-Linolenic Acid (GLA) | 18 | 3 | 6,9,12-octadecatrienoic acid | borage oil |
| Arachidic Acid | 20 | 0 | eicosanoic acid | peanut oil, fish oil |
| Gadoleic Acid | 20 | 1 | 9-eicosenoic acid | fish oil |
| Arachidonic Acid (AA) | 20 | 4 | 5,8,11,14-eicosatetraenoic acid | liver fats |
| EPA | 20 | 5 | 5,8,11,14,17-eicosapentaenoic acid | fish oil |
| Behenic acid | 22 | 0 | docosanoic acid | rapeseed oil |
| Erucic acid | 22 | 1 | 13-docosenoic acid | rapeseed oil |
| DHA | 22 | 6 | 4,7,10,13,16,19-docosahexaenoic acid | fish oil |
| Lignoceric acid | 24 | 0 | tetracosanoic acid | small amounts in most fats |

Fatty acyl compositions of some oils useful in the disclosure, reciting the rounded wt. percentage of some leading natural fatty acids, include without limitation the following (from www.scientificpsychic.com/fitness/fattyacids1.html):

TABLE B

Fatty Acid sprayable compositions of Hydrophobic Agents0

| Oil or Fat | Unsat/Sat. ratio | Saturated | |

TABLE B-continued

| Fatty Acid sprayable compositions of Hydrophobic Agents0 | | | | | | | | | |
|---|---|---|---|---|---|---|---|---|---|
| | | | | | | | | Poly unsaturated | |
| | | Saturated | | | | | Mono unsatur. | Linoleic | Alpha Linolenic |
| Oil or Fat | Unsat/ Sat. ratio | Capr. Acid C10:0 | Laur. Acid C12:0 | Myris. Acid C14:0 | Palm. Acid C16:0 | Stear. Acid C18:0 | Oleic Acid C18:1 | Acid (ω6) C18:2 | Acid (ω3) C18:3 |
| Sunflower Oil* | 7.3 | — | — | — | 7 | 5 | 19 | 68 | 1 |
| Walnut Oil | 5.3 | — | — | — | 11 | 5 | 28 | 51 | 5 |

*Not high-oleic variety

The hydrophobic agents can be colorants, such as for example annatto oil, paprika oil, chlorophyll, lycopene, carotenoids, xanthophylls or the like. The hydrophobic agents can be essential nutrients, such as for example, vitamins such as Vitamin D and its derivatives, Vitamin A and its derivatives, Vitamin E and its derivatives, Vitamin K, Vitamin F, Vitamin P, and the like. Other such nutrients include for example lipoic acid, lycopene, phospholipids, ceramides, ubiqinone, sterols, flavonoids, cholesterol, sphingolipids, prostaglandins, docosahexaenoic acid, and the like.

The hydrophobic agents can be fragrances or flavors, such as for example terpenes, isoterpenenes, alkyl lactones, essential oils, natural oils such as vanilla, and the like. The hydrophobic agents can be aroma providers that impart aroma to or modify aroma of a topical sprayable composition.

The hydrophobic agents (including aesthetic modifying agents if present) can be present in the emulsion composition in an amount of 0.01% wt. to 70%, or 0.1% wt. to 70%, or 5% to 65%, or 0.2% wt. to 60%, or 10% to 60%, by wt., or 0.3% wt. to 55%, or 0.4% wt. to 50%, based on the total weight of the emulsion composition.

The hydrophobic agents can include aesthetic modifying agents or active or therapeutic agents. Active or therapeutic agents and aesthetic modifying agents can include hydrophobic agents and hydrophilic agents.

For example, 0.01% wt. to 70%, or 0.1% wt. to 70%, or 0.5% to 65%, or 0.2% wt. to 60%, or 1% to 60%, or 0.3% wt. to 55%, by wt., based on the total weight of the emulsion can be hydrophobic agents.

In embodiments, the skin, hair or mucosal sprayable composition can be for example 0.01% wt. to 70% wt, or 0.1% wt. to 65%, or 0.5% to 60%, or 0.25% wt. to 55%, or 1% to 50%, based on the total weight of the emulsion, of hydrophobic agents.

As used herein, active or therapeutic agents can be hydrophobic, in which case they will associate with the hydrophobic agent particles, or hydrophilic, in which case they will associate with the aqueous-solute fluid.

Suitable active or therapeutic agents, both hydrophobic and hydrophilic, include, but are not limited to, anti-acne agents, antimicrobial agents, anti-inflammatory agents, analgesics, anti-erythemal agents, anti-pruritic agents, anti-edemal agents, anti-psoriatic agents, anti-fungal agents, skin protectants, sunscreen agents, vitamins, antioxidants, scavengers, anti-irritants, anti-bacterial agents, antiviral agents, antiaging agents, photoprotection agents, hair growth enhancers, hair growth inhibitors, hair removal agents, anti-dandruff agents, anti-seborrheic agents, exfoliating agents, wound healing agents, anti-ectoparasitic agents, sebum modulators, immunomodulators, hormones, botanicals, moisturizing agents, hand sanitizing agents, astringents, sensates, antibiotics, anesthetics, steroids, tissue healing substances, tissue regenerating substances, amino acids, peptides, minerals, ceramides, biohyaluronic acids, skin bleaching ingredients, and any derivatives or combinations of the foregoing.

Suitable active or therapeutic agents that are anti-acne agents include, but are not limited to, salicylic acid, retinoic acid, alpha hydroxy acid, benzoyl peroxide, sodium sulfacetamide, clindamycin, hydrocortisone, tetrahydrozoline, and any derivatives or mixtures thereof.

Suitable active or therapeutic agents that are antimicrobial agents include, but are not limited to, benzalkonium chloride, benzethonium chloride, chlorhexidine gluconate, chloroxylenol, clindamycin, cloflucarban, erythromycin, fluorosalan, hexachlorophene, hexylresorcinol, iodine complex, iodine tincture, para-chloromercuriphenol, phenylmercuric nitrate, thimerosal, vitromersol, zyloxin, triclocarban, triclosan, methyl-benzethonium chloride, nonyl phenoxypoly (ethyleneoxy) ethanol-iodine, para-chloro-meta-xylenol, providone-iodine complex, poloxamer-iodine complex, undecoylium chloride-iodine complex, and any derivatives or combinations of the foregoing.

Suitable active or therapeutic agents that are anti-inflammatory agents include, but are not limited to, alidoxa, allantoin, aloe vera, aluminum acetate, aluminum hydroxide, bismuth subnitrate, boric acid, calamine, casein, microporous cellulose, cholecalciferol, cocoa butter, cod liver oil, colloidal oatmeal, cysteine hydrochloride, dexpanthenol, dimethicone, glycerin, alpha-bisabolol, sea whip extract, glycyrrhetinic acid and its salts and derivatives, kaolin, lanolin, live yeast cell derivative, mineral oil, Peruvian balsam, petrolatum, protein hydrolysate, racemethionine, shark liver oil, sodium bicarbonate, sulfur, talc, tannic acid, topical starch, vitamin A, vitamin E, white petrolatum, zinc acetate, zinc carbonate, zinc oxide, hydrocortisone, betamethasone, ibuprofen, indomethacin, acetylsalicylic acid, tacrolimus, fluocinolone acetonide, sodium sulfacetamide, and any derivatives or combinations of the foregoing.

Suitable active or therapeutic agents that are analgesics include, but are not limited to, diphenhydramine, tripelennamine, benzocaine, dibucaine, lidocaine, tetracaine, camphor, menthol, phenol, resorcinol, matacresol, juniper tar, methylsalicylate, turpentine oil, *capsicum*, methyl nicotinate, beta-glucan, and any derivatives or combinations of the foregoing.

Suitable active or therapeutic agents that are anti-erythemal agents include, but are not limited to, tetrahydrozoline and hydrocortisone, and any derivatives or combinations of the foregoing.

Suitable active or therapeutic agents that are antipruritic agents include, but are not limited to, diphenhydramine, pramoxine, antihistamines, and any derivatives or combinations of the foregoing.

Suitable active or therapeutic agents that are anti-edema agents, include, but are not limited to, pregnenolone acetate, tannin glycosides, and any derivatives or combinations of the foregoing.

Suitable active or therapeutic agents that are antipsoriatic agents include, but are not limited to, calcipotriene, coal tar, anthralin, vitamin A, hydrocortisone, retinoic acid, alpha hydroxy acid, dovonex, salicylic acid, sunscreen agents, indomethacin, urea; anthralin, and any derivatives or combinations of the foregoing.

Suitable active or therapeutic agents that are antifungal agents include, but are not limited to, clioquinol, haloprogin, miconazole nitrate, clotrimazole, metronidazole, tolnaftate, undecylenic acid, iodoquinol, and any derivatives or combinations of the foregoing.

Suitable active or therapeutic agents that are skin protectants include, but are not limited to, cocoa butter, dimethicone, petrolatum, white petrolatum, glycerin, shark liver oil, allantoin, and any derivatives or combinations of the foregoing.

Suitable active or therapeutic agents that are sunscreen agents or active pharmaceutical ingredients (APIs) include, but are not limited to, ethylhexyl methoxycinnamate, avobenzone, benzophenones, octocrylene, ethylhexyl salicylate, homomenthyl salicylate, triethanolamine salicylate, menthyl anthranilate, PABA, octyl dimethyl para amino acid PABA, 2-ethoxyethyl p-methoxycinnamate, phenylbenzimidazole sulfonic acid, titanium dioxide, zinc oxide, and any derivatives or combinations of the foregoing.

The one or more sunscreen active agents provide adsorption or blocking of UV radiation, before it reaches the skin. Illustrative sunscreen active agents include, for example, avobenzone, cinoxate, dioxybenzone, homosalate, menthyl anthranilate, octocrylene, octisalate, octyl methoxycinnamate, octyl salicylate, oxybenzone, padimate O, phenylbenzimidazole sulfonic acid, sulisobenzone, titanium dioxide, trolamine salicylate, zinc oxide, benzophenone-3, ethylhexyl methoxycinnamate, octocrylene, butyl methoxydibenzoylmethane (BMBM), diethylamino hydroxybenzoyl hexyl benzoate, diethylhexyl butamido triazone, PABA, camphor benzalkonium methosulfate, phenylbenzimidazole sulfonic acid, terephthalidene dicamphor sulfonic acid, benzylidene camphor sulfonic acid, polyacrylamidomethyl benzylidene camphor, PEG-25 PABA, isoamyl p-methoxycinnamate, ethylhexyl triazone, drometrizole trielloxane, 4-methylbenzylidene camphor, 3-benzylidene camphor, ethylhexyl salicylate, ethylhexyl dimethyl PABA, benzophenone-4, methylene bis-benztriazolyl tetramethylbutylphenol, disodium phenyl dibenzimidazole tetrasulfonate, bis-ethylhexyloxyphenol methoxyphenol triazine, methylene bisbenzotriazolyl tetramethylbutylphenol, bisethylhexyloxyphenol methoxyphenyl triazine, and any combination thereof.

In an embodiment, the sunscreen active agent is selected from homosalate, octocrylene, avobenzone, octisalate, ethylhexyl methoxycinnamate, butyl methoxydibenzoylmethane (BMBM), diethylamino hydroxybenzoyl hexyl benzoate, diethylhexyl butamido triazone, or any combination thereof.

In another embodiment, the sunscreen active agent comprises homosalate, octocrylene, ethylhexyl methoxycinnamate, butyl methoxydibenzoylmethane (BMBM), diethylamino hydroxybenzoyl hexyl benzoate, and diethylhexyl butamido triazone.

Approved sunscreen active agents in the United States and elsewhere include, for example, paraaminobenzoic acid, avobenzone, cinoxate, dioxybenzone, homosalate, menthyl anthranilate, octocrylene, octyl methoxycinnamate, octyl salicylate, oxybenzone, 2-ethylhexyl 4-(dimethylamino) benzoate (e.g., Padimate O), phenylbenzimidazole sulfonic acid, octisalate, sulisobenzone, trolamine salicylate, titanium dioxide, and zinc oxide. Several other sunscreen active or therapeutic ingredients are accepted for use in other countries. Examples from outside the United States include Tinosorb M, Tinosorb S, Uvinul T-150, UVA sorb HEB, Uvinul A Plus, Neo Heliopan AP, and Neo Heliopan MBC.

Suitable active or therapeutic agents that are antioxidants include, but are not limited to, scavengers for lipid free radicals and peroxyl radicals, quenching agents, astaxanthin, tocopherol, butylated hydroxytoluene (BHT), beta carotene, vitamin A, ascorbic acid and aliphatic derivatives, ubiquinol, ferulic acid, azelaic acid, thymol, catechin, sinapic acid, ethylenediaminetetraacetic acid (EDTA), lactoferrin, rosmariquinone, hydroxytyrosol, sesamol, 2-thioxanthine, nausin, malvin, carvacone, chalcones, glutathione isopropyl ester and other aliphatic derivatives, xanthine, melanin, guanisone, loporphyrins, 8-hydroxyxanthine, 2-thioxanthione, vitamin B12, plant alkaloids, catalase, quercetin, superoxide dismutase (SOD), cysteine, methionine, genistein, nordihydroguaiaretic acid (NDGA), procyanidin, hamamelitannin, ubiquinone, trolox, licorice extract, propyl gallate, and any derivatives or combinations of the foregoing.

Suitable active or therapeutic agents that are vitamins include, but are not limited to, vitamin E, vitamin A palmitate, vitamin D, vitamin F, vitamin B6, vitamin B3, vitamin B12, vitamin C (ascorbic acid or water soluble derivatives of ascorbic acid), ascorbyl palmitate, vitamin E acetate, biotin, niacin, dl-panthenol, and any derivatives or combinations of the foregoing.

As described herein, the active or therapeutic agents can be hydrophobic, in which case they will associate with the hydrophobic agent particles, or hydrophilic, in which case they will associate with the aqueous-solute fluid.

In embodiments, hydrophobic active or therapeutic agents comprise 60% wt. or less of the submicron hydrophobic agent emulsion composition.

Examples of aesthetic modifying agents include without limitation C2-C26 alkyls substituted with 2-24 hydroxyls, where all of the hydroxyls of the foregoing compounds are independently acylated with a saturated, unsaturated, linear, branched or cyclic C1-C24 alkane. In embodiments, the substituted C2-C26 alkyls are reduced sugars (i.e., of the general formula $C_iH_{2i+2}O_n$).

An example of a hydrophobic agent is a compound having the formula A $$C_pH_{(2p+2-q)} \qquad (A)$$

where p is an integer greater than or equal to 6 and q is 0 or an even integer no greater than p. Such compounds include, but are not limited to, saturated and unsaturated, linear, branched, cyclic hydrocarbon chains. Examples of such compounds include without limitation mineral oil, petrolatum, permethyl fluids, polybutenes, polyisobutenes, and any derivatives or mixtures thereof.

Another example of a hydrophobic aesthetic modifying agent has formula B:

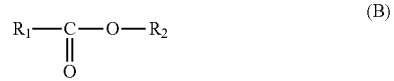

or formula C:

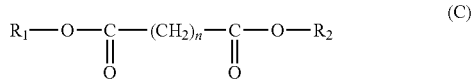

where $R_1$ is a saturated or unsaturated, linear, branched or cyclic C1-C23 acyl moiety having 0, 1, or more substituent groups; $R_2$ is hydrogen or a saturated or unsaturated, liner, branched or cyclic C1-C24acyl moiety having 0, 1, or more substituent groups; and n is an integer from 0 to 20. Examples of such aesthetic modifying agents include, but are not limited to, isopropyl palmitate and diisopropyl adipate.

Another example of a hydrophobic aesthetic modifying agent has formula D:

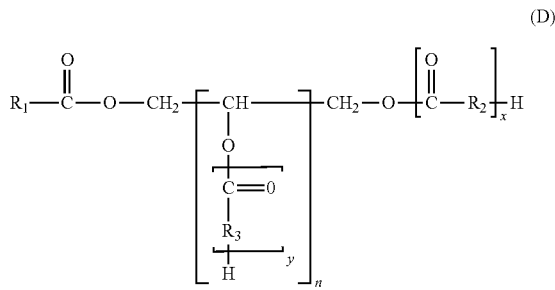

wherein R1 is a $C_6$ to $C_{24}$ acyloate group comprising saturated, unsaturated, cyclic, branched, substituted, oxidized, reduced, polymeric, or copolymeric hydrocarbon(s); R2 and R3 are independently a $C_3$ to $C_{24}$ acyloate group comprising saturated, unsaturated, cyclic, branched, substituted, oxidized, reduced, polymeric, or copolymeric hydrocarbon(s), less 1 hydrogen at the omega carbon; x is a value of 0 or 1; y is a value of 0 to n; and n is a value of 1 to 6.

Still another aesthetic modifying agent is silicone. Silicone may provide lubrication and/or shine to the formulation. Preferably, the silicone is insoluble in water. Suitable water-insoluble silicone materials include, but are not limited to, polysiloxanes, cyclic siloxanes, polyalkylsiloxanes, polyarylsiloxanes, polyalkylarylsiloxanes, polysiloxane gums, polyethersiloxane copolymers, and silicone crosspolymers. Examples of suitable silicone materials are disclosed in U.S. Pat. Nos. 4,788,006; 4,341,799; 4,152,416; 3,964,500; 3,208,911; 4,364,837 and 4,465,619, all of which are incorporated herein by reference for their teachings on silicone materials.

Another suitable hydrophobic material which can be suspended in the formulation has formula E:

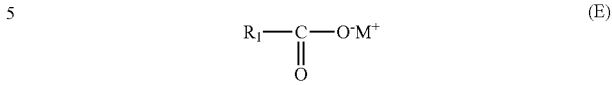

wherein $M^+$ is $N^+R_3R_4R_5R_6$; wherein $R_3$, $R_4$, and $R_5$, are each independently hydrogen or a saturated or unsaturated, linear or branched alkane or hydroxyalkane group having from 1 to 10 carbon atoms; and $R_6$ is a saturated or unsaturated, linear, branched or cyclic alkyl or substituted alkane group having 2 to 24 carbon atoms. An example of such a material is dimethyl lauramine oleate.

Nonionic Surfactant(s) or Emulsifier(s)

The one or more nonionic surfactant(s) or emulsifier(s) useful in this disclosure comprise ester(s) of one or more fatty acid moieties with one or more hydroxyl groups of glycerol or polyglycerol (e.g., glyceryl acyloates and polyglyceryl acyloates) having a HLB from about 3 to about 20, based on the degree of glyceryl units or ethoxyl units, or combinations thereof; and optionally ester(s) of one or more fatty acid moieties with one or more hydroxyl groups of sucrose (e.g., sucrose acyloates) having a HLB from about 2 to about 18, based on the degree of glyceryl units or ethoxyl units, or combinations thereof.

Illustrative glyceryl acyloate and polyglyceryl acyloate surfactants or emulsifiers useful in this disclosure include, for example, polyglyceryl oleate, polyglyceryl-3 oleate, polyglyceryl-4 oleate, polyglyceryl-6 oleate, polyglyceryl caprate, polyglyceryl-2 caprate, polyglyceryl-3 caprate, polyglyceryl-4 caprate, polyglyceryl-6 caprate, polyglyceryl diisostearate, polyglyceryl-2 diisostearate, polyglyceryl-3 diisostearate, polyglyceryl-10 diisostearate, polyglyceryl polyricinoleate, polyglyceryl-3 polyricinoleate, polyglyceryl-6 polyricinoleate, polyglyceryl laurate, polyglyceryl-4 laurate, polyglyceryl-6 laurate, polyglyceryl-10 laurate, polyglyceryl caprylate, polyglyceryl-3 caprylate, polyglyceryl-6 caprylate, polyglyceryl cocoate, polyglyceryl-3 cocoate, polyglyceryl dicaprate, polyglyceryl-6 dicaprate, polyglyceryl polyhydroxystearate, polyglyceryl-6 polyhydroxystearate, polyglyceryl rice branate, polyglyceryl-3 rice branate, polyglyceryl stearate, polyglyceryl-2 stearate, polyglyceryl-3 stearate, polyglyceryl-4 stearate, polyglyceryl-6 stearate, polyglyceryl behenate, polyglyceryl-3 behenate, polyglyceryl-6 behenate, polyglyceryl dioleate, polyglyceryl-10 dioleate, polyglyceryl-10 mono/dioleate, polyglyceryl beeswax, polyglyceryl-3 beeswax, polyglyceryl myristate, polyglyceryl-10 myristate, polyglyceryl octastearate, polyglyceryl-6 octastearate, polyglyceryl decaoleate, polyglyceryl-10 decaoleate, polyglyceryl triisostearate, polyglyceryl-2 triisostearate, polyglyceryl pentaoleate, polyglyceryl-6 pentaoleate, polyglyceryl-10 pentaoleate, polyglyceryl distearate, polyglyceryl-2 distearate, polyglyceryl-3 distearate, polyglyceryl-6 distearate, polyglyceryl diisostearate, polyglyceryl-3 diisostearate, polyglyceryl sesqiisostearate, polyglyceryl-2 sesqiisostearate, polyglyceryl isostearate, polyglyceryl-4 isostearate, polyglyceryl dipolyhydroxystearate, polyglyceryl-2 dipolyhydroxystearate, polyglyceryl sesqioleate, polyglyceryl-2 sesqiolate, polyglyceryl triolivate, polyglyceryl-3 triolivate, polyglyceryl pentaisostearate, polyglyceryl-10 pentaisostearate, polyglyceryl sorbityl linseedate, polyglyceryl-3 sorbityl linseedate, polyglyceryl octadecabehenate/hydroxystearate, polyglyceryl-20 octadecabehenate/ hydroxystearate, polyglyceryl methylglucose distearate, polyglyceryl-3 methylglucose distearate, polyglyceryl olivate/polyricinoleate, polyglyceryl-4 olivate/polyricinoleate, polyglyceryl laurate/succinate, polyglyceryl-4 laurate/succinate, polyglyceryl caprate/caprylate/succinate, polyglyceryl-3 caprate/caprylate/succinate, polyglyceryl cetearyl ether olivate, polyglyceryl-3 cetearyl ether olivate, polyglyceryl dimer dilinoleate, polyglyceryl-3 dimer dilinoleate, polyglyceryl diisostearate/polyhydroxystearate/sebacate, polyglyceryl-4 diisostearate/polyhydroxystearate/sebacate, polyglyceryl oleyl ether olivate, polyglyceryl-4 oleyl ether olivate, polyglyceryl cetyl ether olivate/succinate, polyglyceryl-3 cetyl ether olivate/succinate, and any derivatives or combinations thereof.

Illustrative sucrose ester, or sucrose alkylate, surfactants or emulsifiers useful in this disclosure include, for example, sucrose palmitate, sucrose cocoate, sucrose stearate, sucrose polystearate, sucrose distearate, sucrose laurate, sucrose dilaurate, sucrose trilaurate, and any derivatives or combinations thereof.

The glyceryl acyloate and polyglyceryl acyloate surfactants or emulsifiers useful in this disclosure have an HLB from about 3 to about 20, or from about 7 to about 19, or from about 9 to about 18, or from about 11 to about 17.5, based on the degree of glyceryl units or ethoxyl units, or combinations thereof.

The sucrose acyloate surfactants or emulsifiers useful in this disclosure have an HLB from about 2 to about 18, from about 10 to about 17.5, or from about 12 to about 17, or from about 12.5 to about 16, or from about 13 to about 16, based on the degree of glyceryl units or ethoxyl units, or combinations thereof.

The one or more glyceryl acyloate or polyglyceryl acyloate surfactants or emulsifiers are present in an amount from about 0.01% wt. to about 10% wt., or from about 0.01% wt. to about 5% wt., or from about 0.05% wt. to about 4.5% wt., or from about 0.01% wt. to about 4% wt., or from about 0.15% wt. to about 3.5% wt., based on the total weight of the emulsion.

The one or more sucrose acyloate surfactants or emulsifiers are present in an amount from about 0% wt. to about 10% wt., or from about 0.1% wt. to about 8% wt., or from about 0.2% wt. to about 7.5% wt., or from about 0.3% wt. to about 6% wt., based on the total weight of the sprayable composition.

The one or more nonionic surfactant(s) or emulsifier(s) are sufficient to stabilize the submicron particles of one or more hydrophobic agent(s), in the emulsions, at a level from about 0.05% w/w to about 70% w/w of said one or more hydrophobic agent(s), in the emulsions. The one or more nonionic surfactant(s) or emulsifier(s) are present in an amount from about 0.01% wt. to about 10% wt., or amount from about 0.01% wt. to about 5% wt., or amount from about 0.05% wt. to about 4.5% wt., or amount from about 0.1% wt. to about 4% wt., or amount from about 0.15% wt. to about 3.5% wt., based on the total weight of the emulsion.

Aqueous-Solute Fluids

The aqueous-solute fluid according to the disclosure can be water or a combination of water and one or more materials or solutes that have a solubility in water of 0.1% by weight or greater. Aqueous-solute fluids include, for example, water miscible liquids or solutes, water soluble liquids or solutes, and water soluble solids or solutes.

Illustrative water soluble liquids or solutes useful in this disclosure include, for example, glyceraldehyde, erythrose, erythrulose, sedoheptulose, and the like.

Illustrative water soluble solids or solutes useful in this disclosure include, for example, carbohydrates selected from monosaccharides, reduced sugar alcohols, sugar acids, substituted monosaccharides, disaccharides, triglycerides, and polysaccharides (glycans); amino acids, peptides, and proteins; vitamins; minerals; and any derivatives or combinations thereof.

Illustrative monosaccharides include, for example. 1,3-dihydroxy-2-propanone, arabinose, ribose, xylose, lyxose, ribulose, xylulose, psicose, sorbose, tagatose, threose, glucose, fructose, mannose, galactose, allose, altrose, gulose, indose, talose, and dihydroxacetone.

Illustrative reduced sugar alcohols include, for example, threitol, arabitol, xylitol, ribitol, mannitol, sorbitol, galactitol, fucitol, iditol, inositol, volemitol, isomalt, maltitol, and lactitol.

A sugar acid or acidic sugar is a monosaccharide with a carboxyl group at one end or both ends of its chain. Illustrative sugar acids include, for example, aldonic acids, ulosonic acids, uronic acids, and aldaric acids. With aldonic acids, the aldehyde group (—CHO) located at the initial end (position 1) of an aldose is oxidized. With ulosonic acids, the —CH$_2$(OH) group at the initial end of a 2-ketose is oxidized creating an α-ketoacid. With uronic acids, the —CH$_2$(OH) group at the terminal end of an aldose or ketose is oxidized. With aldaric acids, both ends (—CHO and —CH$_2$(OH)) of an aldose are oxidized.

Other examples of sugar acids include aldonic acids such as glyceric acid, xylonic acid, gluconic acid, threonic acid, and ascorbic acid; ulosonic acids such as neuraminic acid (5-amino-3,5-dideoxy-D-glycero-D-galacto-non-2-ulosonic acid), and ketodeoxyoctulosonic acid (KDO or 3-deoxy-D-manno-oct-2-ulosonic acid); uronic acids such as glucuronic acid, galacturonic acid, lactobionic acid, and iduronic acid; and aldaric acids such as tartaric acid, meso-galactaric acid (mucic acid), and D-glucaric acid (saccharic acid).

Still other examples of sugar acids include N-acetylneuraminic acid, N-acetyltalosaminuronic acid, aldonic acid, 3-deoxy-D-manno-oct-2-ulosonic acid, N-glycolylneuraminic acid, hexenuronic acid, isosaccharinic acid, lactobionic acid, muramic acid, pangamic acid, sialic acid, threonic acid, ulosonic acid, and uronic acid.

Illustrative substituted monosaccharides useful in this disclosure include, for example, sugar esters including phosphate sugar esters, amino sugar esters, acylate sugar esters, and any derivatives or combinations thereof.

Illustrative phosphate sugar esters include, for example, glucose-1-phosphate, fructose-1,6-diphosphate, and any derivatives or combinations thereof.

Illustrative amino sugar esters include, for example, 2-glucosamine, 2-galactosamine, N-acetylglucosamine, N-acetylmannosamine, neuraminic acid, N-acetyltalosaminuronic acid, and any derivatives or combinations thereof.

Illustrative acylate sugar esters include, for example, methyl-glucoside, muramic acid, N-acetyl-neuraminic acid, N-glycosyl-neuraminic acid, pangamic acid, and any derivatives or combinations thereof.

Illustrative disaccharides useful in this disclosure include, for example, sucrose (fructose-glucose), lactose (galactose-glucose), maltose (glucose-glucose), isomaltose, maltobiose, trehalose, cellobiose, and any derivatives or combinations thereof.

Illustrative triglycerides useful in this disclosure include, for example, raffinose (glucose-fructose-galactose), melizitose, and any derivatives or combinations thereof.

Illustrative polysaccharides (glycans) useful in this disclosure include, for example, starch, glycogen, amylopectin, amylose, cellulose, dextran, chitan, alginic acid, agarose, glycosylaminoglycans including chondroitin sulfate, heparin, hyaluronic acid, dermatan sulfate, keratan sulfate, ascorbic acid (vitamin C), the 3-D form of glucuronic acid, and any derivatives or combinations thereof.

Illustrative amino acids, peptides, and proteins useful in this disclosure include, for example: alpha-amino acids including alanine, arginine, asparagine, aspartate, cysteine, glutamate, glutamine, glycine, histidine, isoleucine, leucine, lysine, methionine, phenylalanine, proline, serine, threonine, tryptophan, valine, selenocysteine, pipecolic acid, pyrrolysine, and any derivatives or combinations thereof; beta-amino acids including beta-alanine, beta-aminoisobutyric acid, and any derivatives or combinations thereof; gamma-amino acids including gamma-amino butyric acid, carnitine, and any derivatives or combinations thereof; dipeptides including cysteinyl-thionine, glycyl-glycine, alanyl-histidine, cysteinyl-glycine, and any derivatives or combinations thereof; tripeptides including glutathione, glycyl-glycyl-glycine, lysyl-lysyl-lysine, glutamyl-histeinyl-glycine, and any derivatives or combinations thereof; substituted amino acids and peptides including acetyl carnitine, acetyl cysteine, methylglycinate, glutathione methyl ester, and any derivatives or combinations thereof; proteins including enzymes, cytokines, growth factors, structural proteins such as collagen, elastin, keratin, and any derivatives or combinations thereof.

Illustrative vitamins useful in this disclosure include, for example: vitamin C (ascorbic acid or water soluble derivatives of ascorbic acid), vitamin B1 (thiamin), vitamin B2 (riboflavin), vitamin B3 (niacin), vitamin B5 (pantothenic acid), vitamin B6 (pyridoxin), vitamin B7 (biotin), vitamin B9 (folate), vitamin B12 (cobalamin), and any derivatives or combinations thereof.

Illustrative minerals useful in this disclosure include, for example: aluminum bromide, aluminum chlorate, aluminum chloride, aluminum nitrate, aluminum sulfate, ammonium acetate, ammonium bromide, ammonium carbonate, ammonium chlorate, ammonium chloride, ammonium fluoride, ammonium hydrogen carbonate, ammonium iodide, ammonium nitrate, ammonium phosphate, ammonium sulfate, ammonium sulfide, ammonium sulfite, barium acetate, barium bromide, barium chlorate, barium chloride, barium hydroxide, barium iodide, barium nitrate, barium nitrite, calcium acetate, calcium bromide, calcium chlorate, calcium chloride, calcium iodide, calcium nitrate, calcium nitrite, cobalt (III) acetate, cobalt (III) bromide, cobalt (III) chlorate, cobalt (III) chloride, cobalt (III) iodide, cobalt (III) nitrate, cobalt (III) sulfate, copper (II) acetate, copper (II) bromide, copper (II) chlorate, copper (II) chloride, copper (II) fluoride, copper (II) nitrate, copper (II) sulfate, iron (II) acetate, iron (II) bromide, iron (II) chloride, iron (II) iodide, iron (II) nitrate, iron (II) sulfate, iron (III) bromide, iron (III) chloride, iron (III) iodide, iron (III) nitrate, iron (III) sulfate, lead (II) acetate, lead (II) chlorate, lead (II) nitrate, lead (II) nitrite, lithium acetate, lithium bromide, lithium carbonate, lithium chlorate, lithium chloride, lithium fluoride, lithium hydrogen carbonate, lithium hydroxide, lithium iodide, lithium nitrate, lithium nitrite, lithium sulfate, lithium sulfide, lithium sulfite, magnesium acetate, magnesium bromide, magnesium chlorate, magnesium chloride, magnesium iodide, magnesium nitrate, magnesium nitrite, magnesium sulfate, magnesium sulfite, nickel acetate, nickel bromide, nickel chlorate, nickel chloride, nickel fluoride, nickel iodide, nickel nitrate, nickel sulfate, potassium acetate, potassium bromide, potassium carbonate, potassium chlorate, potassium chloride, potassium fluoride, potassium hydrogen carbonate, potassium hydroxide, potassium iodide, potassium nitrate, potassium nitrite, potassium phosphate, potassium sulfate, potassium sulfide, potassium sulfite, silver chlorate, silver fluoride, silver nitrate, sodium acetate, sodium bromide, sodium carbonate, sodium chlorate, sodium chloride, sodium fluoride, sodium hydrogen carbonate, sodium hydroxide, sodium iodide, sodium nitrate, sodium nitrite, sodium phosphate, sodium sulfate, sodium sulfide, sodium sulfite, zinc acetate, zinc bromide, zinc chlorate, zinc chloride, zinc fluoride, zinc iodide, zinc nitrate, zinc sulfate, and any derivatives or combinations thereof.

Illustrative water miscible liquids or solutes useful in this disclosure include, for example, acetaldehyde, acetic acid, acetone, 1,2-butylene glycol, 1,3-butylene glycol, 1,4-butylene glycol, 2-butoxyethanol, dimethyl sulfoxide, ethanol, ethoxydiglycol, triethylene glycol, ethylene glycol, methanol, isopropanol, 1,2-propylene glycol, 1,3-propylene glycol, 1-propanol, propanoic acid, diglycerin, polyglycerol, glycerin, 1,5-pentylene glycol, hexylene glycol, and any derivatives or combinations thereof.

Other illustrative water miscible liquids or solutes include, for example, one or more of liquids or solutes according to formula E:

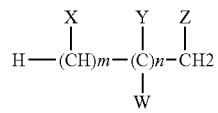

(E)

where X, Y and Z are independently —H or —OH; W is independently —H or —$CH_3$; m is 0 or 1; and n is an integer from 0 to 6. For example, the liquids or solutes can be mono, di, tri, tetra or penta alcohols, such as, but not limited to, methanol, ethanol, isopropyl alcohol, propanol, butanol, ethylene glycol, propylene glycol, butylene glycol, pentylene glycol, glycerol, tetritol, pentitol, 1,3 propane diol, and the like, or mixtures thereof. In embodiments, the liquids or solutes are, but are not limited to, one or more ethanol, propanol, butylene glycol, pentylene glycol, hexylene glycol, glycerol, 1,3-propane diol, or mixtures thereof. In embodiments, the liquid or solute is ethanol.

Illustrative alcohols include organic compounds that carry at least one hydroxyl functional group (—OH) bound to a saturated carbon atom. Examples include mono, di, tri, tetra or penta alcohols. Examples further include ethanol or isopropanol. Examples still further include methanol, ethanol, isopropanol, propanol, butanol, 1-octanol (capryl alcohol), caprylyl alcohol, ethylene glycol, propylene glycol, butylene glycol, pentylene glycol, hexylene glycol, glycerol or glycerin, tetritol, pentitol, 1,3 propane diol, and the like, or mixtures thereof.

The water-miscible liquid or solute of the aqueous-solute fluid can have, without limitation, concentrations greater than 10%, or 20%, or 30% wt. in the aqueous-solute fluid, or less than 95%, 90%, or 80%, or 70% wt, or a range therebetween. The water of the aqueous-solute fluid can have, without limitation, concentration greater than 4.99%, or 10%, or 20%, or 30% wt. in the aqueous-solute fluid, or less than 89.99%, or 80%, or 70% wt, or a range therebetween.

In an embodiment, in the aqueous-solute fluids of this disclosure, at least 10%, or at least 15%, or at least 20%, or at least 25%, of the water soluble liquids comprise water miscible liquids.

In reciting that a sprayable composition of the disclosure has a given percentage of water-miscible liquid or solute, it will be recognized that during formulation that total amount of the water miscible liquid or solute can be contributed from (i) a concentrated emulsion of submicron particles of hydrophobic agent(s), (ii) a separate aqueous-solute fluid that may be mixed with the concentrated emulsion, or (iii) both. Similarly, the water can come from either or both sources.

The aqueous-solute fluid is present in an amount from about 20% wt. to about 99% wt., or amount from about 25% wt. to about 95% wt., or amount from about 30% wt. to about 90% wt., or amount from about 35% wt. to about 85% wt., based on the total weight of the sprayable composition.

Rheological Modifying Agents

The emulsions can optionally include a rheological modifying agent. Such agents are known in the art and include, but are not limited to, those set forth at www.foodadditives.org/food_gums/common.html.

Suitable rheological modifying agents include, but are not limited to, phosphorylated starch derivative, carbohydrate based rheological modifying agents, polymeric and copolymeric rheological modifying agents, inorganic rheological modifying agents, protein rheological modifying agents, polypeptide rheological modifying agents, and any derivatives or combinations of the foregoing.

Examples of a phosphorylated starch derivative include, but are not limited to, starches containing a phosphate group. Suitable phosphorylated starch derivatives include, but are not limited to, hydroxyalkyl starch phosphates, hydroxyalkyl distarch phosphates, and any combination of any of the foregoing. Non-limiting examples of hydroxyalkyl starch phosphates and hydroxyalkyl distarch phosphates include: hydroxyethyl starch phosphate, hydroxypropyl starch phosphate, hydroxypropyl distarch phosphate (including sodium hydroxypropyl starch phosphate), and any derivatives or combinations of the foregoing.

Non-limiting examples of suitable carbohydrate based rheological modifying agents include algin and derivatives and salts thereof (such as algin, calcium alginate, propylene glycol alginate, and ammonium alginate); carrageenan (*Chondrus crispus*) and derivatives and salts thereof (such as calcium carrageenan and sodium carrageenan); agar; cellulose and derivatives thereof (such as carboxymethyl hydroxyethylcellulose, cellulose gum, hydroxyethylcellulose, hydroxypropylcellulose, hydroxypropyl methylcellulose, and ethylcellulose); chitosan and derivatives and salts thereof (such as hydroxypropyl chitosan, carboxymethyl chitosan, and chitin); gellan gum; guar (*Cyamopsis tetragonoloba*) and derivatives thereof (such as guar hydroxypropyltrimonium chloride and hydroxypropyl guar); hyaluronic acid and derivatives thereof (such as sodium hyaluronate); dextran and derivatives thereof; dextrin; locust bean (*Ceratonia siliqua*) gum; starches (such as starch polyacrylonitrile copolymer-potassium salt and starch polyacrylonitrile copolymer-sodium salt); pectin; *sclerotium* gum; tragacanth (*Astragalus gummifer*) gum; xanthan gum and derivatives thereof; and any derivatives or combinations of the foregoing.

Non-limiting examples of suitable polymeric and copolymeric rheological modifying agents include acrylates, methacrylates, polyethylene and derivatives thereof, and any combination of any of the foregoing. Suitable acrylates and methacrylates include, but are not limited to, carbomer and derivatives and salts thereof, acrylates/C10-C30 alkyl acrylate crosspolymer, acrylates/ceteth-itaconate copolymer, acrylates/ceteth-methacrylate copolymers, acrylates/steareth-methacrylate copolymers, acrylates/steareth-20 itaconate copolymers, acrylates/steareth-50 acrylate copolymers, acrylates/VA crosspolymers, acrylates/vinyl isodecanoate crosspolymers, acrylic acid/acrylonitrogen copolymers, ammonium acrylates/acrylonitrogen copolymers, glyceryl polymethacrylate, polyacrylic acid, PVM/MA decadiene crosspolymer, sodium acrylate/vinyl isodecanoate crosspolymers, sodium carbomer, ethylene/acrylic acid copolymer, ethylene/VA copolymer, acrylates/acrylamide copolymer, acrylate copolymers, acrylates/hydroxyester acrylate copolymers, acrylate/octylarylamide copolymers, acrylates/PVP copolymers, AMP/acrylate copolymers, butylester of PVM-MA copolymer, carboxylate vinyl acetate terpolymers, diglycol/CHDM/isophthalates/SIP copolymer, ethyl ester of PVM-MA copolymer, isopropyl ester of PVM-MA copolymer, octylacrylamide/acrylate/butylaminoethyl methacrylate copolymers, polymethacrylamidopropyltrimonium chloride, propylene glycol oligosuccinate, polyvinylcaprolactam, PVP, PVP/dimethylaminoethylmethacrylate copolymer, PVP/DMAPA acrylate copolymers, PVP/carbamyl polyglycol ester, PVP/VA copolymer, PVP/VA vinyl propionate copolymer, PVP/vinylcaprolactam/DMAPA acrylate copolymers, sodium polyacrylate, VA/butyl maleate/isobornyl acrylate copolymers, VA/crotonates copolymer, VA/crotonates vinyl neodecanoate copolymer, VA/crotonates/vinyl propionate copolymer, vinyl caprolactam/PVP/dimethylaminoethylmethacrylate copolymer, hydroxyethyl Acrylate/Sodium Acryloyldimethy Taurate Copolymer, and any derivatives or combinations of the foregoing.

Non-limiting examples of suitable inorganic rheological modifying agents include clays and derivatives thereof, silicates, silicas and derivatives thereof, and any combination of any of the foregoing. Suitable clays and derivatives thereof include, but are not limited to, bentonite and derivatives thereof, such as quaternium-18 bentonite; hectorite and derivatives thereof, such as quaterniums; montmorillonite; and any derivatives or combinations of the foregoing. Suitable silicates include, but are not limited to, magnesium aluminum silicate, sodium magnesium silicate, lithium magnesium silicate, tromethamine magnesium aluminum silicate, and any derivatives or combinations of the foregoing. Suitable silicas and derivatives thereof include, but are not limited to, hydrated silica, hydrophobic silica, spherical silica, and any derivatives or combinations of the foregoing.

Suitable protein and polypeptide rheological modifying agents include, but are not limited to, proteins and derivatives and salts thereof, polypeptides and derivatives and salts thereof, and any combination of any of the foregoing. Non-limiting examples of protein and polypeptide rheological modifying agents include albumin, gelatin, keratin and derivatives thereof, fish protein and derivatives thereof, milk protein and derivatives thereof, wheat protein and derivatives thereof, soy protein and derivatives thereof, elastin and derivatives thereof, silk protein and derivatives thereof, and any derivatives, casein and any derivatives or combinations of the foregoing.

Particularly suitable rheological modifying agents include, but are not limited to, carbomer, acrylate/alkyl acrylate crosspolymers, acrylate/vinyl isododecanoate crosspolymer, xanthan gum, hydroxyethyl cellulose, locust bean gum, guar gum, and any combination of any of the foregoing. A suitable combination of rheological modifying agents comprises carbomer and an acrylate/alkyl acrylate copolymer, such as an acrylates/C10-C30 alkyl acrylate crosspolymer. According to the International Cosmetic Ingredient Dictionary and Handbook (7th ed., The Cosmetic, Toiletry, and Fragrance Association), carbomer is a homopolymer of acrylic acid crosslinked with an allyl ether of pentaerythritol, an allyl ether of sucrose, or an allyl ether of propylene. The term "acrylate/alkyl acrylate crosspolymer" includes, but is not limited to, copolymers of alkyl acrylates with one or more monomers of acrylic acid, methacrylic acid, or one of their short chain (i.e. C1-4 alcohol) esters, wherein the crosslinking agent is, for example, an allyl ether of sucrose or pentaerytritol. Preferably, the alkyl acrylates are C10-C30 alkyl acrylates. Examples of such copolymers include, but are not limited to, those commercially available as Ultrez-21, Ultrez-20, Carbopol™ 1342, Carbopol™ 1382, Pemulen™ TR-1, and Pemulen™ TR-2, from Novion, Cleveland, Ohio. Particularly suitable rheological modifying agents include, but are not limited to, hydrophilic gelling agents, such as carboxyvinyl polymers (carbomer), acrylic copolymers (e.g., acrylate/alkyl acrylate copolymers), polyacrylamides, Hydroxyethyl Acrylate/Sodium Acryloyldimethyl Taurate Copolymers, polysaccharides (e.g. hydroxypropylcellulose), natural gums (e.g., xanthan gum), clays, and any derivatives or combinations of the foregoing.

Examples of fatty acids providing fatty acyl components, or which provide hydrophobic agents include, without limitation, for example: Butyric acid, Caproic Acid, Caprylic Acid, Capric Acid, Lauric Acid, Myristic Acid, Palmitic Acid, Palmitoleic Acid, Stearic Acid, Oleic Acid, Ricinoleic acid, Vaccenic Acid, Linoleic Acid, Alpha-Linolenic Acid (ALA), Gamma-Linolenic Acid (GLA), Arachidic Acid, Gadoleic Acid, Arachidonic Acid (AA), EPA, Behenic acid, Erucic acid, DHA, and Lignoceric acid.

Fatty acyl sprayable compositions of some oils useful in the invention, include without limitation: Almond Oil, Beef Tallow, Butterfat (cow), Butterfat (goat), Butterfat (human), Canola Oil, Cocoa Butter, Cod Liver Oil, Coconut Oil, Corn Oil (Maize Oil), Cottonseed Oil, Flaxseed Oil, Grape seed Oil, Illipe, Lard (Pork fat), Olive Oil, Palm oil, Palm Olein, Palm Kernel Oil, Peanut Oil, Safflower Oil, Sesame Oil, Shea nut, soybean Oil, Sunflower Oil, Walnut Oil.

The rheological modifying agent can be present in the sprayable composition or in the emulsion of hydrophobic agents in an amount from 0.01 to 10% wt, or 0.1 to 5%, or 0.2 to 2%.

Rheological modifying agents are added in particular to help immobilize the particles of hydrophobic agents for still longer term stability of the submicron emulsions.

Humectants

The emulsions can optionally include a humectant. Humectants are materials that bind water through hydrogen bonding. Humectants generally have multiple hydroxyl groups or amino groups. Mono, di, and poly carbohydrate or reduced carbohydrate molecules are particularly good humectants. Three-carbon trihydroxy compounds like glycerin are also particularly good.

Most 5 carbon and 6 carbon mono-, di-, and poly saccharide will bind water. Glucose, ribose, fructose, xylose, xylitol, mannitol, and sucrose will bind water which is released into dry skin to improve its functionality. Polysaccharides composed of a long-chain of either a mono-carbohydrate, di-carbohydrates, or poly-carbohydrates are also suitable humectants. Glycogen, hyaluronic acid, honey, and chondroitin sulfate are examples of Poly carbohydrates that can complex copious amount of water. They release moisture into the skin to keep it hydrated and supple for extended periods. Other examples of humectants are proteins, amino acids, and ammonium lactate. The aforementioned humectants are exemplary and not intended to be limiting.

The humectant can be present in the sprayable composition or in the emulsion of hydrophobic agents in conventional amounts, for example, an amount from 0.01 to 10% wt, or 0.1 to 5%, or 0.2 to 2%.

Edible Hydrophobic Agents

Examples of edible hydrophobic agents include but are not limited to mono, di, tri, or poly alkyl (or alkenyl) esters or ethers of a di, tri, or polyhydroxy compound, such as glycerin, sorbitol or other polyol compound. Examples of such esters or ethers include but are not limited to, saturated and unsaturated, linear and branched vegetable oils, such a soybean oil, almond oil, castor oil, canola oil, cottonseed oil, grapeseed oil, rice bran oil, palm oil, coconut oil, palm kernel oil, olive oil, linseed oil, sunflower oil, safflower oil, peanut oil and corn oil. Useful saturated and unsaturated oils include those having 90% or more (molar) fatty acyl components with 6 to 30 carbon atoms, such as 6 to 24 carbons, or 12 to 24 carbons.

Examples of fatty acids providing fatty acyl components, or which provide hydrophobic agents include, without limitation, for example those listed in Table A above.

Fatty acyl sprayable compositions of some oils useful in the invention, reciting the rounded wt percentage of some leading natural fatty acids, include without limitation those listed in Table B above.

In embodiments, without limitation, about 51% wt or more of the edible hydrophobic agent(s) are one or more of the oils identified above. In embodiments, without limitation, about 51% wt or more of the edible hydrophobic agent(s) are avocado oil, canola oil, corn oil, cottonseed oil, flaxseed oil, grape seed oil, peanut oil, safflower oil, sesame oil, soybean oil, sunflower oil, walnut oil, olive oil, peppermint oil, orange oil, or a mixture thereof.

The edible hydrophobic agents can be present in the submicron hydrophobic agent emulsion sprayable composition in an amount of 0.01% wt. to 70%, or 5% to 65%, or 10% to 60%, by weight.

Edible Nonionic Surfactants or Emulsifiers

Edible nonionic surfactants or emulsifiers are useful in a variety of applications, for example, food, biomedicine and cosmetics. Edible nonionic surfactants or emulsifiers refer to those nonionic surfactants which can be consumed by human beings, animals or microorganisms without any noxious effects towards health.

The one or more edible nonionic surfactants or emulsifiers useful in this disclosure comprise ester(s) of one or more fatty acid moieties with one or more hydroxyl groups of glycerol or polyglycerol (e.g., glyceryl acyloates and polyglyceryl acyloates), and optionally ester(s) of one or more fatty acid moieties with one or more hydroxyl groups of sucrose (e.g., sucrose acyloates).

Illustrative edible glyceryl acyloate and polyglyceryl acyloate surfactants or emulsifiers useful in this disclosure include, for example, polyglyceryl oleate, polyglyceryl-3 oleate, polyglyceryl-4 oleate, polyglyceryl-6 oleate, polyglyceryl caprate, polyglyceryl-2 caprate, polyglyceryl-3 caprate, polyglyceryl-4 caprate, polyglyceryl-6 caprate, polyglyceryl diisostearate, polyglyceryl-2 diisostearate, polyglyceryl-3 diisostearate, polyglyceryl-10 diisostearate, polyglyceryl polyricinoleate, polyglyceryl-3 polyricinoleate, polyglyceryl-6 polyricinoleate, polyglyceryl laurate, polyglyceryl-4 laurate, polyglyceryl-6 laurate, polyglyceryl-10 laurate, polyglyceryl caprylate, polyglyceryl-3 caprylate, polyglyceryl-6 caprylate, polyglyceryl cocoate, polyglyceryl-3 cocoate, polyglyceryl dicaprate, polyglyceryl-6 dicaprate, polyglyceryl polyhydroxystearate, polyglyceryl-6 polyhydroxystearate, polyglyceryl rice branate, polyglyceryl-3 rice branate, polyglyceryl stearate, polyglyceryl-2 stearate, polyglyceryl-3 stearate, polyglyceryl-4 stearate, polyglyceryl-6 stearate, polyglyceryl behenate, polyglyceryl-3 behenate, polyglyceryl-6 behenate, polyglyceryl dioleate, polyglyceryl-10 dioleate, polyglyceryl-10 mono/dioleate, polyglyceryl beeswax, polyglyceryl-3 beeswax, polyglyceryl myristate, polyglyceryl-10 myristate, polyglyceryl octastearate, polyglyceryl-6 octastearate, polyglyceryl decaoleate, polyglyceryl-10 decaoleate, polyglyceryl triisostearate, polyglyceryl-2 triisostearate, polyglyceryl pentaoleate, polyglyceryl-6 pentaoleate, polyglyceryl-10 pentaoleate, polyglyceryl distearate, polyglyceryl-2 distearate, polyglyceryl-3 distearate, polyglyceryl-6 distearate, polyglyceryl diisostearate, polyglyceryl-3 diisostearate, polyglyceryl sesqiisostearate, polyglyceryl-2 sesqiisostearate, polyglyceryl isostearate, polyglyceryl-4 isostearate, polyglyceryl dipolyhydroxystearate, polyglyceryl-2 dipolyhydroxystearate, polyglyceryl sesqioleate, polyglyceryl-2 sesqiolate, polyglyceryl triolivate, polyglyceryl-3 triolivate, polyglyceryl pentaisostearate, polyglyceryl-10 pentaisostearate, polyglyceryl sorbityl linseedate, polyglyceryl-3 sorbityl linseedate, polyglyceryl octadecabehenate/hydroxystearate, polyglyceryl-20 octadecabehenate/hydroxystearate, polyglyceryl methylglucose distearate, polyglyceryl-3 methylglucose distearate, polyglyceryl olivate/polyricinoleate, polyglyceryl-4 olivate/polyricinoleate, polyglyceryl laurate/succinate, polyglyceryl-4 laurate/succinate, polyglyceryl caprate/caprylate/succinate, polyglyceryl-3 caprate/caprylate/succinate, polyglyceryl cetearyl ether olivate, polyglyceryl-3 cetearyl ether olivate, polyglyceryl dimer dilinoleate, polyglyceryl-3 dimer dilinoleate, polyglyceryl diisostearate/polyhydroxystearate/sebacate, polyglyceryl-4 diisostearate/polyhydroxystearate/sebacate, polyglyceryl oleyl ether olivate, polyglyceryl-4 oleyl ether olivate, polyglyceryl cetyl ether olivate/succinate, polyglyceryl-3 cetyl ether olivate/succinate, and any derivatives or combinations thereof.

Illustrative edible sucrose acyloate surfactants or emulsifiers useful in this disclosure include, for example, sucrose palmitate, sucrose cocoate, sucrose stearate, sucrose polystearate, sucrose distearate, sucrose laurate, sucrose dilaurate, sucrose trilaurate, and any derivatives or combinations thereof.

The edible glyceryl acyloate and polyglyceryl acyloate surfactants or emulsifiers useful in this disclosure have an HLB from about 3 to about 20, or from about 7 to about 19, or from about 9 to about 18, or from about 11 to about 17.5, based on the degree of glyceryl units or ethoxyl units, or combinations thereof.

The edible sucrose acyloate surfactants or emulsifiers useful in this disclosure have an HLB from about from about 2 to about 18, from about 10 to about 17.5, or from about 12 to about 17, or from about 12.5 to about 16, or from about 13 to about 16, based on the degree of glyceryl units or ethoxyl units, or combinations thereof.

The edible glyceryl acyloate and polyglyceryl acyloate surfactants or emulsifiers are sufficient to stabilize the submicron particles of one or more hydrophobic agent(s), in the emulsions, at a level from about 0.05% w/w to about 70% w/w of said one or more hydrophobic agent(s), in the emulsions. The one or more edible glyceryl acyloate and polyglyceryl acyloate surfactants or emulsifiers are present in an amount from about 0.01% wt. to about 10% wt., or amount from about 0.01% wt. to about 5% wt., or amount from about 0.05% wt. to about 4.5% wt., or amount from about 0.1% wt. to about 4% wt., or amount from about 0.15% wt. to about 3.5% wt., based on the total weight of the sprayable composition.

The edible sucrose acyloate surfactants or emulsifiers are sufficient to stabilize the submicron particles of one or more hydrophobic agent(s), in the emulsions, at a level from about 0.05% w/w to about 70% w/w of said one or more hydrophobic agent(s), in the emulsions. The one or more edible sucrose acyloate surfactants or emulsifiers are present in an amount from about 0.01% wt. to about 10% wt., or amount from about 0.1% wt. to about 8% wt., or amount from about 0.2% wt. to about 7.5% wt., or amount from about 0.25% wt. to about 5% wt., or amount from about 0.3% wt. to about 4.5% wt., based on the total weight of the sprayable composition.

Edible Rheological Modifying Agents

The emulsion can optionally include edible rheological modifying agents. Such agents are known in the art and include, without limitation, those set forth in the following Table C adapted from www.foodadditives.org/food_gums/common.html.

TABLE C

| Rheological Agents |
| --- |
| Agar-agar - a gum consisting of two repeating units of polysaccharides: alpha-D-galactopyranosyl and 3,6-anhydro-alpha-L-glactopyranosyl derived from red seaweed. Traditional agar-agar can bind approximately 100 times its weight in water when boiled, forming a strong gel that is often used as a stabilizer or thickener. A recent application of agar-agar is replacing gelatin as the gelling agent in dairy products, such as yogurt. Agar-agar is a non-animal gel source which is suitable for vegetarians and people with religious dietary restrictions (Kosher/Halal). |
| Alginate - is a polysaccharide, like starch and cellulose, and is derived from brown seaweed. Alginate provides properties in processed foods and beverages such as gelling, viscosifying, suspending and stabilizing. Alginate gelling may be achieved using calcium under controlled conditions. It employs the combination of alginate, a slowly soluble calcium salt and a suitable calcium sequestrant, such as a phosphate or citrate. The process may be performed at neutral or acid pH. |
| Carrageenan - a water soluble gum derived from red seaweeds, such as Eucheuma, Gigartina, and Chondrus. Carrageenan is a sulfated linear polysaccharide of D-galactose and it has a strong negative charge, thereby allowing it to stabilize gels or act as a thickener. Carrageenan is found in numerous products, ranging from toothpaste to soy milk. It is used to suspend cocca solids in beverages, for example, and can be used in meats to reduce cooking losses. |

TABLE C-continued

Rheological Agents

Cassia Gum - is a naturally occurring galactomannan found in the endosperm of cassia tora and obtusifolia seeds. It is an effective thickener and stabilizer for a broad range of food applications. Cassia gum has excellent retort stability and forms strong synergistic gels with other hydrocolloids including carrageenan and xanthan gum. Human food grade cassia gum is specially processed to meet rigorous purity standards.
Cellulose Gum - Carboxymethyl Cellulose (CMC), or cellulose gum is an abundant and natural polysaccharide found in all plants. Cellulose gum is a water-soluble gum that is based on cellulose. Cellulose gum has been used in food products for over 50 years as a thickener and stabilizer. Typical uses are in instant beverages, where it provides texture, baked goods, where it prevents staling, and ice-cream, where it prevents the formation of ice-crystals that can be formed from frequent freezing and rethawing.
Gellan Gum - a food gum that is primarily used as a gelling or thickening agent. It can be used in fortified beverages to suspend protein, minerals, vitamins, fiber and pulp. Gellan gum also suspends milk solids in diluted milk drinks. Gellan gum can act as a fluid gel, having a wide range of textures, and can exist as a light pourable gel or a thick, spreadable paste. Gellan gum is a non-animal gel source which is suitable for vegetarians and people with religious dietary restrictions (Kosher/Halal).
Guar Gum - a carbohydrate consisting of mannose and galactose at a 2:1 ratio that can swell in cold water. Guar gum is one of the most highly efficient water-thickening agents available to the food industry and is widely used as a binder and volume enhancer. Its high percentage of soluble dietary fiber (80 to 85%), means that it is often added to bread to increase its soluble dietary fiber content. Guar gum is also commonly used to thicken and stabilize salad dressings and sauces and help improve moisture retention in finished baked goods.
Hydroxypropyl cellulose - cellulose is an abundant and natural polysaccharide found in all plants. Hydroxypropyl cellulose is based on cellulose and is used in many food products to provide good foam stability. Hydroxypropyl cellulose is commonly found in whipped toppings where it stabilizes the foam and provides a long lasting whipped topping with dairy-like eating quality.
Konjac Gum- a polysaccharide from a plant known as elephant yam, which is commonly found in Asia. This gum can be used as a vegan substitute for gelatin and other thickeners. Its texture makes it ideal for jellies because of its high viscosity.
Locust Bean Gum - also called Carob bean gum, locust bean gum is derived from the seeds of the carob bean. Locust bean gum is used for thickening, water-binding, and gel strengthening in a variety of foods. It has synergistic interactions with other gums, such as xanthan or carrageenan, and can be used in applications such as dairy, processed cream cheese, and dessert gels.
Methylcellulose and Hydroxypropyl Methylcellulose - cellulose is an abundant and natural polysaccharide found in all plants. Methylcellulose and hydroxypropyl methylcellulose are based on cellulose and are used in many food products to provide texture, certain mouth feels and other desirable qualities. These gums are commonly found in soy burgers where they add meat-like texture to the vegetable proteins, in fried appetizers like mozzarella cheese sticks and onion rings where they create firm texture by reducing the uptake of frying oils, and in whipped toppings where they stabilize the foam structure to give long lasting creams.
Microcrystalline cellulose (MCC) - is a polysaccharide derived from naturally occurring cellulose similar to that found in fruits and vegetables. MCC can be used as a bulking agent, source of fiber and moisture regulator in processed foods. MCC may also be co-processed with carboxymethyl cellulose (CMC) to impart shear-thinning and heat stable properties. Additional properties in food and beverages from MCC/CMC co-processed products include gelling, viscosifying, suspending and stabilizing.
Pectin - a polysaccharide derived from plant material, mainly citrus fruit peels, apple peels, or sugar beets. Pectin is widely used to impart gel formation, thickening, and physical stability to a wide range of foods. It is mostly used in fruit-based products, including jams, jellies, confectioneries, and fruit drinks, but is also used in dairy applications such as drinking and spoonable yogurt.
Xanthan Gum - a highly branched polysaccharide of D-glucose, D-mannose, and D-glucuronic acid produced via bacterial fermentation using nutrient sources. Xanthan gum, which is considered natural, is an excellent emulsion stabilizer in salad dressings and sauces and also is used in bakery fillings to prevent water migration from the filling to the pastry (which has strong water-binding properties). Xanthan gum can often be used to improve the shelf life of a product.

The edible rheological modifying agent can be present in the sprayable composition or in the emulsion of edible hydrophobic agents in an amount from 0.01 to 10% wt, or 0.1 to 5%, or 0.2 to 2%. Edible rheological modifying agents are added in particular to help immobilize the particles of edible hydrophobic agents for still longer term stability of the submicron emulsions.

Adjuvants and Additives

The submicron hydrophobic agent emulsion sprayable composition can contain suitable functional adjuvants which may include, but are not limited to, pH adjusters, emollients, conditioning agents, chelating agents, colorants, fragrances, flavors, odor masking agents, non-dispersed actives, UV stabilizers, preservatives, neutralizing agents, and any combination of any of the foregoing. Suitable pH adjusters include, but are not limited to, aminomethyl propanol, aminomethylpropane diol, triethanolamine, citric acid, sodium hydroxide, acetic acid, potassium hydroxide, lactic acid, and any combination of any of the foregoing. Suitable conditioning agents include, but are not limited to, cyclomethicone, petrolatum, dimethicone, dimethiconol, silicone, quaternary amines, and any combination of any of the foregoing. The formulation can for example contain less than about 4.0% by weight of preservatives, based upon weight of total formulation, or from about 0.25% to about 3% by weight of preservatives, based upon weight of total formulation.

The rheological modifying adjuvants can be present in the sprayable composition or in the emulsion of hydrophobic agents in conventional amounts, for example, an amount from 0.01 to 10% wt, or 0.1 to 5%, or 0.2 to 2%.

In an embodiment, adding a conditioning agent can help provide the sprayable compositions of this disclosure with desirable feel properties (e.g., a silky, lubricious feel upon application). Some non-limiting examples of conditioning agents include, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and any derivatives or combinations thereof. Particularly suitable examples of conditioning agents include volatile or non-volatile silicone fluids such as dimethicone copolyol, dimethylpolysiloxane, diethylpolysiloxane, mixed C1-30 alkyl polysiloxanes, phenyl dimethicone, dimethiconol, dimethicone, dimethiconol, silicone crosspolymers, and any derivatives or combinations thereof. Dimethicone may be especially suitable, since some consumers associate the feel properties provided by certain dimethicone fluids with good moisturization. The sprayable compositions herein may include 0.1% to 50% by weight of a conditioning agent (e.g., 0.5% to 30%, 1% to 20%, or even 2% to 15%).

Delivery Vehicle for Active or Therapeutic Ingredients

In accordance with this disclosure, each emulsion can provide a multifunctional delivery vehicle for active or therapeutic, hydrophobic and hydrophilic, ingredients, including one or more: anti-acne agents, antimicrobial agents, anti-inflammatory agents, analgesics, anti-erythemal agents, antipruritic agents, antiedemal agents, anti-psoriatic agents, antifungal agents, skin protectants, sunscreen agents, vitamins, antioxidants, anti-irritants, anti-bacterial agents, antiviral agents, antiaging agents, photoprotection agents, exfoliating agents, wound healing agents, sebum modulators, immunomodulators, hormones, botanicals, moisturizing agents, hand sanitizing agents, astringents, sensates, antibiotics, anesthetics, steroids, tissue healing substances, tissue regenerating substances, amino acids, peptides, minerals, ceramides, hyaluronic acids, skin bleaching ingredients, pre-biotics, probiotics, hemp oils, cannabinoids, and any derivatives or combinations of the foregoing. Advantageously, the emulsions provide such a multifunctional delivery vehicle without the need for heating which can alter or damage actives. Further the hydrophobic active or therapeutic agents will be mixed with the hydrophobic materials and the hydrophilic active or therapeutic agents will be mixed into the aqueous solute fluid.

Anti-acne agents include, but are not limited to, salicylic acid, retinoic acid, alpha hydroxy acid, benzoyl peroxide, sodium sulfacetamide, clindamycin, hydrocortisone, tetrahydrozoline, and any derivatives or mixtures thereof.

Antimicrobial agents include, but are not limited to, benzalkonium chloride, benzethonium chloride, chlorhexidine gluconate, chloroxylenol, clindamycin, cloflucarban, erythromycin, fluorosalan, hexachlorophene, hexylresorcinol, iodine complex, iodine tincture, para-chloromercuriphenol, phenylmercuric nitrate, thimerosal, vitromersol, zyloxin, triclocarban, triclosan, methyl-benzethonium chloride, nonyl phenoxypoly (ethyleneoxy) ethanol-iodine, para-chloro-meta-xylenol, providone-iodine complex, poloxamer-iodine complex, undecoylium chloride-iodine complex, and any derivatives or combinations of the foregoing.

Anti-inflammatory agents include, but are not limited to, alidoxa, allantoin, aloe vera, aluminum acetate, aluminum hydroxide, bismuth subnitrate, boric acid, calamine, casein, microporous cellulose, cholecalciferol, cocoa butter, cod liver oil, colloidal oatmeal, cysteine hydrochloride, dexpanthenol, dimethicone, glycerin, alpha-bisabolol, sea whip extract, glycyrrhetinic acid and its salts and derivatives, kaolin, lanolin, live yeast cell derivative, mineral oil, peruvian balsam, petrolatum, protein hydrolysate, racemethionine, shark liver oil, sodium bicarbonate, sulfur, talc, tannic acid, topical starch, vitamin a, vitamin e, white petrolatum, zinc acetate, zinc carbonate, zinc oxide, hydrocortisone, betamethasone, ibuprofen, indomethacin, acetylsalicylic acid, tacrolimus, fluocinolone acetonide, sodium sulfacetamide, and any derivatives or combinations of the foregoing.

Analgesics include, but are not limited to, diphenhydramine, tripelennamine, benzocaine, dibucaine, lidocaine, tetracaine, camphor, menthol, phenol, resorcinol, matacresol, juniper tar, methylsalicylate, *eucalyptus* oil, turpentine oil, *capsicum*, methyl nicotinate, beta-glucan, and any derivatives or combinations of the foregoing.

Anti-erythemal agents include, but are not limited to, tetrahydrozoline and hydrocortisone, and any derivatives or combinations of the foregoing.

Antipruritic agents include, but are not limited to, diphenhydramine, pramoxine, antihistamines, and any derivatives or combinations of the foregoing.

Anti-edema agents include, but are not limited to, pregnenolone acetate, tannin glycosides, and any derivatives or combinations of the foregoing.

Anti-psoriatic agents include, but are not limited to, calcipotriene, coal tar, anthralin, vitamin A, hydrocortisone, retinoic acid, alpha hydroxy acid, dovonex, salicylic acid, sunscreen agents, indomethacin, urea; anthralin, and any derivatives or combinations of the foregoing.

Antifungal agents include, but are not limited to, clioquinol, haloprogin, miconazole nitrate, clotrimazole, metronidazole, tolnaftate, undecylenic acid, iodoquinol, and any derivatives or combinations of the foregoing.

Skin protectants include, but are not limited to, cocoa butter, dimethicone, petrolatum, white petrolatum, glycerin, shark liver oil, allantoin, and any derivatives or combinations of the foregoing.

Sunscreen agents include, but are not limited to, ethylhexyl methoxycinnamate, avobenzone, benzophenones, octocrylene, ethylhexyl salicylate, homomethyl salicylate, triethanolamine salicylate, menthyl anthranilate, PABA, octyl dimethyl PABA, 2-ethoxyethyl p-methoxycinnamate, phenylbenzimidazole sulfonic acid, titanium dioxide, zinc oxide, and any derivatives or combinations of the foregoing.

Antioxidants include, but are not limited to, scavengers for lipid free radicals and peroxyl radicals, quenching agents, astaxanthin, tocopherol, butylated hydroxytoluene (BHT), beta carotene, vitamin A, ascorbic acid and aliphatic derivatives, ubiquinol, ferulic acid, azelaic acid, thymol, catechin and derivatives thereof, epicatechins, polyphenol, bioflavonoids and derivatives thereof, sinapic acid, ethylenediaminetetraacetic acid (EDTA), lactoferrin, rosmariquinone, hydroxytyrosol, sesamol, 2-thioxanthine, nausin, malvin, carvacone, chalcones, glutathione, glutathione isopropyl ester and other aliphatic derivatives, xanthine, melanin, guanisone, loporphyrins, 8-hydroxyxanthine, 2-thioxanthione, vitamin B12, plant alkaloids, catalase, quercetin, superoxide dismutase (SOD), cysteine, methionine, genistein, nordihydroguaiaretic acid (NDGA), procyanidin, hamamelitannin, ubiquinone, trolox, licorice extract, propyl gallate, and any derivatives or combinations of the foregoing.

Vitamins include, but are not limited to, vitamin E, vitamin A palmitate, vitamin D, vitamin F, vitamin B1 (thiamine), vitamin B2 (riboflavin), vitamin B6 (pyridoxine), vitamin B3 (niacin), vitamin B5 (pantothenic acid, panthenol)), vitamin B6 (pyridoxine), vitamin B7 (biotin), vitamin B9 (folic acid), vitamin B12 (cobalamin), vitamin C (ascorbic acid or water soluble derivatives of ascorbic acid), ascorbyl palmitate, vitamin E acetate, and any derivatives or combinations of the foregoing.

Sensates include, but are not limited to, menthol, isopulegole, 3-(I-menthoxy)propan-1 2-diol, p-menthan-3,8-diol 6-isopropyl-9-methyl-1,4-dioxaspiro-(4,5)-decane-2-methanol, menthyl succinate, alkaline earth salts of menthyl succinate, trimethyl cyclohexanol, N-ethyl-2-isopropyl-5-methylcyclohexane carboxamide, 3-(1-menthoxy)-2-methyl-propan-1,2-diol, mint oil, peppermint oil, wintergreen, menthone, menthone glycerin ketal, menthyl lactate, [1'R,2'S,5'R]-2-(5'-methyl-2'-(methylethyl)cyclohexyloxy) ethan-1-ol, [1'R,2S,5'R]-3-5'-methyl-2' (methylethyl)cyclohexyloxy)propan-1-ol, [1'R,2'S,5R]-4-(5'-methyl-2' (methylethyl)cyclohexyloxy)butan-1-ol, spearmint, and any derivatives or mixtures thereof. Other sensates include, for example, vanillyl ethyl ether, vanillyl propyl ether, vanillin propylene glycol acetal, ethyl vanillin propylene glycol acetal, capsaicin, gingerol, vanillyl butyl ether, 4-(I-menthoxy-methyl)-2-phenyl-1,3-dioxolane, 4-(I-menthoxy-methyl)-2-(3',4'-dihydroxy-phenyl)-1,3-dioxolane, 4-(I-menthoxy-methyl)-2-(2'hydroxy-3'-methoxy-phenyl)-1,3-dioxolane, 4-(I-menthoxy-methyl)-2-(4n ethoxyphenyl)-1, 3-dioxolane, 4-(I-menthoxy-methyl)-2-(3'4'-methylenedioxy-phenyl)-1,3-dioxolane, hot pepper oil, capsicum oleoresin, ginger oleoresin, nonyl acid vanillylamide, 4-I-menthoxy-methyl)-2-(3'-methoxy-hydroxyphenyl)-1,3-dioxolane, and any derivatives or mixtures thereof. Still other sensates include, for example, Jambu Oleoresin, Zanthoxylum peperitum saanshool-I, saanshool II, sanshoamide, Spilanthol, and any derivatives or mixtures thereof.

Pre-biotics include, but are not limited to, inulin, chicory, resistant starches, pectin, and any derivatives or mixtures thereof. Pre-biotics are typically polymers of three carbon, four carbon, five carbon, and six carbon carbohydrates. When pre-biotics are broken down by microorganisms, different short-chain fatty acids are created depending on the kind of pre-biotic. As a result, these short-chain fatty acids do a number of thing like provide energy, and aid in controlling inflammation and enhancing immunity.

Hemp oils and cannabinoids include, but are not limited to, cannabidiol (CBD), delta-9-tetrahydrocannabinol (THC), cannabinol (CBN), cannabigerol (CBG), cannabichromene oil (CBC), any hemp oil or cannabinoid species (e.g., *sativa*, *indica*, *ruderalis*, and the like), and any variants, hybrids, derivatives or combinations thereof. Hemp oils and cannabinoids can do a number of things like reduce risks of illnesses like Alzheimer's disease, cardiovascular disease, skin issues, stress, inflammation in the body, and the like. Other benefits of hemp oils and cannabinoids include, but are not limited to, lowering blood pressure, preventing relapse in drug and alcohol addiction, treating anxiety disorders, treating gastrointestinal disorders, preventing seizures, fighting cancer, and the like.

Material and thus particle size variations can yield different textures by simply adding to the base emulsion, for example, texturizing modifiers, like wax, stearic acid, and stearyl alcohols. However, care should be maintained that saturated fatty acid acyloates can impart a particle size and viscosity that will make them difficult to spray at any appreciable level.

Stability

It is the ultra-high energy mixing that generates the small size of the emulsion particles (i.e., submicron particles of one or more hydrophobic agents), creates a uniform particle size, and imparts a negative charge. This together with the HLB of the nonionic surfactants, the nature of the hydrophobe, the nature of the aqueous-solute fluid, and viscosity/rheology of the rheological modifying agent (if present), that are important for imparting stability. These properties minimize the tendency of hydrophobic particles to coalesce. The commercially viable stability described above (30 days or more under standard conditions) allows a useful amount of time in which to store emulsion and final sprayable compositions (e.g., topical sprayable compositions) to maintain product integrity.

In an embodiment, the sprayable compositions of this disclosure can contain a subphase of a 35% concentrated hydrophobic (or blend of hydrophobic agent(s) emulsion that is then diluted in water, or water plus a water soluble solute, to generate the finished good bulk. That emulsion may be used in the final finished goods bulk at a 1% level. Therefore, the hydrophobe is at 0.35%.

The submicron particles of one or more hydrophobic agent(s) of this disclosure have an average particle size from about 100 nm to less than about 1000 nm, and are 85% or more of a size within ±2.0 standard deviations, of the average particle size.

The one or more nonionic surfactant(s) or emulsifier(s) are sufficient to stabilize the submicron particles of one or more hydrophobic agent(s), in the emulsions, at a level from about 0.05% w/w to about 70% w/w, or from about 0.1% w/w to about 65% w/w, or from about 0.15% w/w to about 60% w/w, or from about 0.2% w/w to about 55% w/w, or from about 0.25% w/w to about 50% w/w, or from about 0.3% w/w to about 45% w/w, or from about 0.3% w/w to about 40% w/w, or from about 0.3% w/w to about 35% w/w, of said one or more hydrophobic agent(s), in the emulsions. Weight/weight equivalents can be calculated as known in the art.

The stability is further manifested in that two or more distinct emulsions can be mixed without decreasing the stability of the various component hydrophobic agent particles, or an emulsion can be diluted into aqueous fluid or aqueous-solute fluid without decreasing the stability of the component hydrophobic agent particles.

Further, if hydrophobic agent A were not compatible with hydrophobic agent B when mixed, nonetheless an emulsion of the disclosure of hydrophobic agent A can be mixed with an emulsion of hydrophobic B, since the individual particles maintain their integrity. Silicone Oil and olive oil exemplify such incompatible hydrophobic agents.

In an embodiment, emulsion stability can be measured in accordance with a centrifuge test described in U.S. Application Publication No. 2022/0183936, the disclosure of which is incorporated herein by reference.

Emulsion stability is dependent on a variety of parameters such as the zeta potential, particle size, crystal formation, and water binding activity of the ingredients employed to achieve the preset or desired rheological properties of the product. These parameters are dependent on the temperature to which the oil and water phases are heated, the rate of heating, the method and rate of mixing of the phases when combined at elevated temperatures, and the rate of cooling.

Most emulsions require heating to ensure that all higher melting point materials, such as waxes and butters, are completely melted, dissolved, or dispersed in the appropriate phase.

If any one of the processing variables is modified unexpectedly, particle size variations may occur or the crystalline properties of the emulsion can be compromised.

Utility

The emulsions of this disclosure are useful in nutritional, pharmaceutical, biomedical, over-the-counter (OTC) drug, cosmetic, personal care, food, animal care, household, pet care, veterinary health, and other applications.

In the methods of the disclosure, animals treated can include, without limitation, humans, domesticated animals (such as dogs, cats, hamsters, gerbils, guinea pigs, cattle, pigs, sheep, goats, horses, zebus, donkeys, mules, buffalos, camels, yaks, mice, rats, other rodents, gayals, rabbits, alpacas, vicunas, llamas, poultry, other domesticated birds, and the like), wild animals, and the like.

A "cosmetic" material according to the disclosure is one that is generally recognized as safe for application to improve the appearance or odor of human or animal skin or mucosa. A "dermatologically appropriate material" is one that is generally recognized as safe for application to human or animal skin or mucosa. In embodiments, all the materials of a sprayable composition containing an emulsion of submicron hydrophobic agents are dermatologically appropriate materials.

In an embodiment, the present method includes identifying a target portion of keratinous tissue (e.g., skin or hair) on a person where treatment is desired and applying an effective amount of the sprayable composition thereto over the course of a treatment period. The target portion of keratinous tissue may be a facial skin surface, such as the forehead, perioral, chin, periorbital, nose, and/or cheek) or another part of the body (e.g., hands, arms, legs, back, chest) or other surfaces or substrates such as wood or food.

Applying the sprayable compositions of this disclosure may be accomplished by localized application. In reference to application of the sprayable composition, the terms "localized", "local", or "locally" mean that the sprayable composition is delivered to the targeted area while minimizing delivery to skin surfaces, or other surfaces and substrates, where treatment is not desired. The sprayable composition may be applied and lightly massaged into an area of skin. The form of the sprayable composition or the dermatologically acceptable carrier should be selected to facilitate localized application. While certain embodiments herein contemplate applying a sprayable composition locally to an area, it will be appreciated that sprayable compositions herein can be applied broadly to one or more skin surfaces, or other surfaces and substrates. In certain embodiments, the sprayable compositions herein may be used as part of a multi-step regimen, wherein the present sprayable composition may be applied before and/or after one or more other sprayable compositions.

In an embodiment, the sprayable composition containing the emulsion of this disclosure can be formulated as a spray sunscreens. The emulsion used in the sprayable compositions can contain active sunscreen agents, for example, ethylhexyl methoxycinnamate, avobenzone, benzophenones, octocrylene, homosalate, ethylhexyl salicylate, homomenthyl salicylate, triethanolamine salicylate, menthyl anthranilate, PABA, octyl dimethyl PABA, 2-ethoxyethyl p-methoxycinnamate, phenylbenzimidazole sulfonic acid, titanium dioxide, zinc oxide, and any derivatives or combinations thereof. The active sunscreen agents and other additives are present in the emulsion used in the sprayable composition in an amount from about 1 wt % to about 70 wt %, or from about 2 wt % to about 65 wt %, or from about 3 wt % to about 60 wt %, or from about 4 wt % to about 55 wt %, based on the total weight of the sprayable composition. The sunscreen formulation has a viscosity from about 1 cps to about 5,000 cps, or from about 2 cps to about 4500 cps, or from about 3 cps to about 4000 cps, or from about 4 cps to about 3500 cps.

In an embodiment, the sprayable composition of this disclosure can be formulated as a sprayable toner/sunscreen. The emulsion used in the sprayable compositions can contain toner ingredients, for example, witch hazel, alpha-hydroxy acids such as glycolic acid, lactic acid, and mandelic acid; beta-hydroxy acids such as salicylic acid; glycerin, hyaluronic acid, panthenol, niacinamide, allantoin, citric acid, hydrogenated starch hydrolysate, rosewater, orange flower water, tocopherol (vitamin E), vitamin C, vitamin CG, and the like. The toner formulation can also include active sunscreen agents as described above. The toner hydrophobic ingredients and other additives are present in the emulsion used in the sprayable compositions in an amount from about 0.01 wt % to about 90 wt %, or from about 0.05 wt % to about 80 wt %, or from about 0.1 wt % to about 70 wt %, or from about 0.15 wt % to about 65 wt %. The toner formulation has a viscosity from about 1 cps to about 2,500 cps, or from about 2 cps to about 2,250 cps, or from about 3 cps to about 2,000 cps, or from about 4 cps to about 1,500 cps.

Other additives include, for example, antioxidants, buffering agents (to control pH); active or therapeutic agents including, for example, humectants, exfoliating agents, skin lightening agents, anti-wrinkle actives, anti-atrophy actives, moisturizing agents, anti-cellulite agents, skin soothing agents; chelating agents, neutralizing agents, freezing point lowering agents, odor control/fragrance, preservatives, rheological modifier, antifoams, and the like.

All ranges recited herein include ranges therebetween and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more.

The following are preferred embodiments of the sprayable compositions of this disclosure.

Embodiment 1. A sprayable composition comprising:
an emulsion comprising (i) submicron particles of one or more hydrophobic agent(s), (ii) an emulsifier system comprising one or more nonionic surfactant(s) or emulsifier(s), and (iii) an aqueous-solute fluid;
wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and wherein the one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion.

Embodiment 2. The sprayable composition of embodiment 1 wherein the submicron particles of one or more hydrophobic agent(s) are present in an amount from about 0.01% wt. to about 70% wt., based on the total weight of the sprayable composition.

Embodiment 3. The sprayable composition of embodiment 1 wherein the aqueous-solute fluid is present in an amount from about 1.0% wt. to about 98.5% wt., based on the total weight of the sprayable composition.

Embodiment 4. The sprayable composition of embodiment 1 wherein the one or more nonionic surfactant(s) or emulsifier(s) are present in an amount from about 0.01% wt. to about 10% wt., based on the total weight of the sprayable composition.

Embodiment 5. The sprayable composition of embodiment 1 wherein the submicron particles of one or more hydrophobic agent(s) (i) have an average particle size from 100 nm to less than about 1000 nm, (ii) have a solubility of less than about 0.1% by weight in water under standard conditions, and (iii) are 85% or more of a size within ±2.0 standard deviations, of the average particle size.

Embodiment 6. The sprayable composition of claim 5 wherein the submicron particles of one or more hydrophobic agent(s) are 85% or more of a size within ±1.9 standard deviations, or within ±1.8 standard deviations, or within ±1.7 standard deviations, or within ±1.6 standard deviations, or within ±1.5 standard deviations, of the average particle size.

Embodiment 7. The sprayable composition of embodiment 1 wherein the one or more nonionic surfactant(s) or emulsifier(s) are sufficient to stabilize the submicron particles of one or more hydrophobic agent(s) in said emulsion, at a level from about 0.1% w/w to about 65% w/w of said one or more hydrophobic agent(s), in said emulsion.

Embodiment 8. The sprayable composition of embodiment 1, wherein the emulsion is prepared by a process comprising:
preparing a premix comprising (i) one or more hydrophobic agent(s), (ii) an emulsifier system comprising one or more nonionic surfactant(s) or emulsifier(s), (iii) an aqueous-solute fluid, and optionally (iv) one or more additive(s);
subjecting the premix to low energy mixing to form a first emulsion; and
subjecting the first emulsion to ultra-high energy mixing to form a second emulsion.

Embodiment 9. The sprayable composition of embodiment 8, wherein the low energy mixing is mechanical and performed at ambient temperature and pressure.

Embodiment 10. The sprayable composition of embodiment 8, wherein the low energy mixing is performed using a homogenizer, rotor stator, vacuum homogenizer, media mill, colloid mill, or combinations thereof.

Embodiment 11. The sprayable composition of embodiment 8, wherein the first emulsion has an average particle size of one or more hydrophobic agent(s) of less than 200 microns, or less than 150 microns, or less than 100 microns.

Embodiment 12. The sprayable composition of embodiment 8, wherein the ultra-high energy mixing is performed using a high-pressure high-shear device, sonicator, or combinations thereof.

Embodiment 13. The sprayable composition of embodiment 8 wherein the ultra-high energy mixing is non-mechanical and performed at a temperature from about 15° C. to about 30° C. and until about 85 wt. % of the total hydrophobic particles of one or more hydrophobic agent(s) in the second emulsion are within ±2.0 standard deviations, of an average particle size of the second emulsion, the average particle size of the one or more hydrophobic agent (s) in the second emulsion being from about 100 nm to less than about 1000 nm.

Embodiment 14. The sprayable composition of embodiment 8, wherein the ultra-high energy mixing is performed at a temperature from about 20° C. to about 25° C.

Embodiment 15. The sprayable composition of embodiment 8, wherein the ultra-high energy mixing is performed until 85 wt. % of the total hydrophobic particles in the emulsion are within ±2.0 standard deviations of the average particle size of the second emulsion.

Embodiment 16. The sprayable composition of embodiment 8, wherein 85 wt. % of the total hydrophobic particles in the second emulsion are within ±1.5 standard deviations, of the average particle size of the second emulsion.

Embodiment 17. The sprayable composition of embodiment 8, wherein the average particle size of the second emulsion is from about 160 nm to about 480 nm.

Embodiment 18. The sprayable composition of embodiment 8, wherein the average particle size of the second emulsion is from about 170 nm to about 400 nm.

Embodiment 19. The sprayable composition of embodiment 8, wherein the ultra-high energy mixing is performed until 90 wt. % of the total hydrophobic particles in the second emulsion are within ±1.75 standard deviations of the average particle size of the second emulsion.

Embodiment 20. The sprayable composition of embodiment 8, wherein the ultra-high energy mixing is performed until 90 wt. % of the total hydrophobic particles in the second emulsion are within ±1.5 standard deviations of the average particle size of the second emulsion.

Embodiment 21. The sprayable composition of embodiment 8, wherein the ultra-high energy mixing is performed until 95 wt. % of the total hydrophobic particles in the second emulsion are within ±1.75 standard deviations, of the average particle size of the second emulsion.

Embodiment 22. The sprayable composition of embodiment 8, wherein the ultra-high energy mixing is performed until 95 wt. % of the total hydrophobic particles in the second emulsion are within ±1.5 standard deviations, of the average particle size of the second emulsion.

Embodiment 23. The sprayable composition of embodiment 8, wherein after ultra-high energy mixing, the average particle size of the one or more hydrophobic agent(s) in the emulsion ranges from about 100 nm to about 999 nm, or from about 125 nm to about 900 nm, or from about 150 nm to about 800 nm, or from about 175 nm to about 750 nm, or from about 200 nm to about 700 nm, or from about 250 nm to about 600 nm.

Embodiment 24. The sprayable composition of embodiment 8, wherein the ester(s) of one or more fatty acid moieties with one or more hydroxyl groups of glycerol or polyglycerol surfactants or emulsifiers comprise glyceryl acyloates or polyglyceryl acyloates including, but not limited to polyglyceryl oleate, polyglyceryl-3 oleate, polyglyceryl-4 oleate, polyglyceryl-6 oleate, polyglyceryl caprate, polyglyceryl-2 caprate, polyglyceryl-3 caprate, polyglyceryl-4 caprate, polyglyceryl-6 caprate, polyglyceryl diisostearate, polyglyceryl-2 diisostearate, polyglyceryl-3 diisostearate, polyglyceryl-10 diisostearate, polyglyceryl polyricinoleate, polyglyceryl-3 polyricinoleate, polyglyceryl-6 polyricinoleate, polyglyceryl laurate, polyglyceryl-4 laurate, polyglyceryl-6 laurate, polyglyceryl-10 laurate, polyglyceryl caprylate, polyglyceryl-3 caprylate, polyglyceryl-6 caprylate, polyglyceryl cocoate, polyglyceryl-3 cocoate, polyglyceryl dicaprate, polyglyceryl-6 dicaprate, polyglyceryl polyhydroxystearate, polyglyceryl-6 polyhydroxystearate, polyglyceryl rice branate, polyglyceryl-3 rice branate, polyglyceryl stearate, polyglyceryl-2 stearate, polyglyceryl-3 stearate, polyglyceryl-4 stearate, polyglyceryl-6 stearate, polyglyceryl behenate, polyglyceryl-3 behenate, polyglyceryl-6 behenate, polyglyceryl dioleate, polyglyceryl-10 dioleate, polyglyceryl-10 mono/dioleate, polyglyceryl beeswax, polyglyceryl-3 beeswax, polyglyceryl myristate, polyglyceryl-10 myristate, polyglyceryl octastearate, polyglyceryl-6 octastearate, polyglyceryl decaoleate, polyglyceryl-10 decaoleate, polyglyceryl triisostearate, polyglyceryl-2 triisostearate, polyglyceryl pentaoleate, polyglyceryl-6 pentaoleate, polyglyceryl-10 pentaoleate, polyglyceryl distearate, polyglyceryl-2 distearate, polyglyceryl-3 distearate, polyglyceryl-6 distearate, polyglyceryl diisostearate, polyglyceryl-3 diisostearate, polyglyceryl sesqiisostearate, polyglyceryl-2 sesqiisostearate, polyglyceryl isostearate, polyglyceryl-4 isostearate, polyglyceryl dipolyhydroxystearate, polyglyceryl-2 dipolyhydroxystearate, polyglyceryl sesqioleate, polyglyceryl-2 sesqiolate, polyglyceryl triolivate, polyglyceryl-3 triolivate, polyglyceryl pentaisostearate, polyglyceryl-10 pentaisostearate, polyglyceryl sorbityl linseedate, polyglyceryl-3 sorbityl linseedate, polyglyceryl octadecabehenate/hydroxystearate, polyglyceryl-20 octadecabehenate/hydroxystearate, polyglyceryl methylglucose distearate, polyglyceryl-3 methylglucose distearate, polyglyceryl olivate/polyricinoleate, polyglyceryl-4 olivate/polyricinoleate, polyglyceryl laurate/succinate, polyglyceryl-4 laurate/succinate, polyglyceryl caprate/caprylate/succinate, polyglyceryl-3 caprate/caprylate/succinate, polyglyceryl cetearyl ether olivate, polyglyceryl-3 cetearyl ether olivate, polyglyceryl dimer dilinoleate, polyglyceryl-3 dimer dilinoleate, polyglyceryl diisostearate/polyhydroxystearate/sebacate, polyglyceryl-4 diisostearate/polyhydroxystearate/sebacate, polyglyceryl-10-stearate, polyglyceryl oleyl ether olivate, polyglyceryl-4 oleyl ether olivate, polyglyceryl cetyl ether olivate/succinate, polyglyceryl-3 cetyl ether olivate/succinate, and any derivatives or combinations thereof.

Embodiment 25. The sprayable composition of embodiment 1, wherein the ester(s) of one or more fatty acid moieties with one or more hydroxyl groups of sucrose surfactants or emulsifiers comprise sucrose acyloates including, but not limited to sucrose palmitate, sucrose cocoate, sucrose stearate, sucrose polystearate, sucrose distearate, sucrose laurate, sucrose dilaurate, sucrose trilaurate, and any derivatives or combinations thereof.

Embodiment 26. The sprayable composition of embodiment 24, wherein the glyceryl acyloate or polyglyceryl acyloate surfactants or emulsifiers have an HLB from about 3 to about 20, or from about 7 to about 19, or from about 9 to about 18, or from about 11 to about 17.5, based on the degree of glyceryl units or ethoxyl units, or combinations thereof.

Embodiment 27. The sprayable composition of embodiment 25, wherein the sucrose acyloate surfactants or emulsifiers have an HLB from about 2 to about 18, from about 10 to about 17.5, or from about 12 to about 17, or from about 12.5 to about 16, or from about 13 to about 16, based on the degree of glyceryl units or ethoxyl units, or combinations thereof.

Embodiment 28. The sprayable composition of embodiments 24 and 25 wherein the glyceryl acyloate or polyglyceryl acyloate surfactants or emulsifiers are present in an amount from about 0.01% wt. to about 10% wt., or from about 0.01% wt. to about 5% wt., or from about 0.05% wt. to about 4.5% wt., or from about 0.1% wt. to about 4% wt., based on the total weight of the sprayable composition; and wherein the sucrose acyloate surfactants or emulsifiers are present in an amount from about 0.01% wt. to about 10% wt., or from about 0.1% wt. to about 8% wt., or from about 0.2% wt. to about 7.5% wt., or from about 0.25% wt. to about 5% wt., based on the total weight of the sprayable composition.

Embodiment 29. The sprayable composition of embodiment 1, wherein the one or more hydrophobic agent(s) include, but are not limited to: mono, di, tri, or poly alkyl (or alkenyl) esters, ethers, acetals and hemiacetals of a di-, tri-, or polyhydroxy compound, and any derivatives or combinations thereof; saturated and unsaturated, linear and branched natural or vegetable oils including, but not limited to soybean oil, almond oil, castor oil, canola oil, cottonseed oil, grapeseed oil, rice bran oil, palm oil, coconut oil, palm kernel oil, olive oil, linseed oil, sunflower oil, safflower oil, peanut oil, corn oil, and any derivatives or combinations thereof; water insoluble silicone materials including, but not limited to polyalkylsiloxanes, polyarylsiloxanes, polyalkylarylsiloxanes, polysiloxane gums, polyethersiloxane copolymers, silicone crosspolymers, and any derivatives or combinations thereof; and water insoluble materials including, but not limited to diglycerides, triglycerides, lauramine oleate, isopropyl palmitate, mineral oil, petrolatum, and any derivatives or combinations thereof.

Embodiment 30. The sprayable composition of embodiment 1, wherein the one or more hydrophobic agent(s) comprise one or more active or therapeutic agent(s).

Embodiment 31. The sprayable composition of embodiment 8, further comprising: adding at least one functional agent to the premix, or post-treating the first emulsion with at least one functional agent, or post-treating the second emulsion with one or more functional agent(s).

Embodiment 32. The sprayable composition of embodiment 30, wherein the one or more active or therapeutic agent(s) comprise one or more hydrophobic agent(s) or one or more hydrophilic agent(s), and include, but are not limited to: anti-acne agents, antimicrobial agents, anti-inflammatory agents, analgesics, anti-erythemal agents, anti-pruritic agents, anti-edemal agents, anti-psoriatic agents, anti-fungal agents, skin protectants, sunscreen agents, vitamins, antioxidants, scavengers, anti-irritants, anti-bacterial agents, antiviral agents, antiaging agents, photoprotection agents, hair growth enhancers, hair growth inhibitors, hair removal agents, antidandruff agents, anti-seborrheic agents, exfoliating agents, wound healing agents, anti-ectoparasitic agents, sebum modulators, immunomodulators, hormones, botanicals, moisturizing agents, hand sanitizing agents, astringents, sensates, antibiotics, anesthetics, steroids, tissue healing substances, tissue regenerating substances, amino acids, peptides, minerals, ceramides, biohyaluronic acids, bleaching ingredients, pre-biotics, probiotics, hemp oils, cannabinoids, and any derivatives or combinations thereof.

Embodiment 33. The sprayable composition of embodiment 30, wherein the one or more active or therapeutic agent(s) comprise at least one sunscreen agent including, but not limited to ethylhexyl methoxycinnamate, avobenzone, benzophenones, octocrylene, homosalate, ethylhexyl salicylate, homomenthyl salicylate, triethanolamine salicylate, menthyl anthranilate, PABA, octyl dimethyl PABA, 2-ethoxyethyl p-methoxycinnamate, phenylbenzimidazole sulfonic acid, titanium dioxide, zinc oxide, and any derivatives or combinations thereof.

Embodiment 34. The sprayable composition of embodiment 1, wherein the one or more hydrophobic agent(s) comprise at least one aesthetic modifying agent.

Embodiment 35. The sprayable composition of embodiment 8, further comprising: treating or post-treating the premix, or post-treating the first emulsion, or post-treating the second emulsion, such that pH is raised or lowered by the addition of an alkali or acid, respectively; viscosity is increased or decreased by the addition of a thickening agent or salt, respectively; specific gravity is adjusted by the addition of one or more of an antifoam, centrifugation, vacuum, and reduction in viscosity with sweeping mixing; refractive index is adjusted up or down by the addition of a high refractive index solvent/solute or water; or active levels are adjusted by the addition of a hydrophobic active emulsion.

Embodiment 36. The sprayable composition of embodiment 1, wherein the one or more hydrophobic agent(s) comprise at least one compound including, but not limited to:

(a) a compound having the formula A

wherein p is a positive integer greater than or equal to 6 and q is 0 or a positive, even integer no greater than p;

(b) a compound having the formula B or C

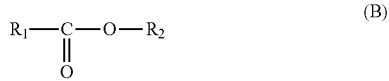

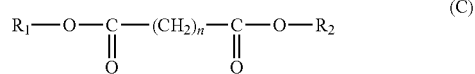

wherein R1 is a saturated or unsaturated, linear, branched or cyclic $C_1$-$C_{23}$ acyl moiety having 0, 1, or more substituent groups; and R2 is hydrogen or a saturated or unsaturated, linear, branched or cyclic $C_1$-$C_{24}$ acyl moiety having 0, 1, or more substituent groups, and n is an integer from 0 to 20;

(c) a compound having the formula D

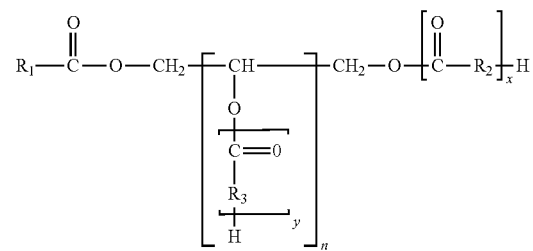

wherein R1 is a $C_6$ to $C_{24}$ acyloate group comprising saturated, unsaturated, cyclic, branched, substituted, oxidized, reduced, polymeric, or copolymeric hydrocarbon(s); R2 and R3 are independently a $C_3$ to $C_{24}$ acyloate group comprising saturated, unsaturated, cyclic, branched, substituted, oxidized, reduced, polymeric, or copolymeric hydrocarbon(s), less 1 hydrogen at the omega carbon; x is a value of 0 or 1; y is a value of 0 to n; and n is a value of 1 to 6; and (d) a silicone or modified polysiloxane.

Embodiment 37. The sprayable composition of embodiment 34, wherein the one or more aesthetic modifying agent(s) comprise at least one compound including, but not limited to: polysiloxanes, cyclic siloxanes, polyalkylsiloxanes, polyarylsiloxanes, polyalkylarylsiloxanes, polysiloxane gums, polyethersiloxane copolymers, and silicone crosspolymers.

Embodiment 38. The sprayable composition of embodiment 34, wherein the one or more aesthetic modifying agent(s) comprise one or more of $C_2$-$C_{26}$ alkanes substituted with 2-24 hydroxyls, wherein the hydroxyls of the foregoing compounds are independently acylated with a saturated, unsaturated, linear, branched or cyclic $C_1$-$C_{24}$ alkane, rendering the substituted alkyls hydrophobic agents.

Embodiment 39. The sprayable composition of embodiment 1, wherein the one or more hydrophobic agent(s) comprise colorants including, but not limited to: annatto oil, paprika oil, chlorophyll, lycopene, carotenoids, xanthophylls, and any derivatives or combinations thereof.

Embodiment 40. The sprayable composition of embodiment 1, wherein the one or more hydrophobic agent(s) comprise essential nutrients including, but not limited to: vitamins such as vitamin D and its derivatives, vitamin A and its derivatives, vitamin E and its derivatives, vitamin K, vitamin F, vitamin P, lipoic acid, lycopene, phospholipids, ceramides, ubiquinone, sterols, flavonoids, cholesterol, sphingolipids, prostaglandins, docosahexaenoic acid, and any derivatives or combinations thereof.

Embodiment 41. The sprayable composition of embodiment 1, wherein the one or more hydrophobic agent(s) comprise fragrances or flavors including, but not limited to: terpenes, isoterpenenes, alkyl lactones, essential oils, natural oils, vanilla, and any derivatives or combinations thereof.

Embodiment 42. The sprayable composition of embodiment 1, wherein the one or more hydrophobic agent(s) comprise one or more active or therapeutic agent(s) and at least one aesthetic modifying agent.

Embodiment 43. The sprayable composition of embodiment 31, wherein the one or more functional agent(s) include, but are not limited to chelating agents, neutralizing agents, foaming agents, rheological modifying agents, sensates, and any derivatives or combinations thereof.

Embodiment 44. The sprayable composition of embodiment 1, wherein the one or more hydrophobic agent(s) are present in an amount of 0.05% wt. to 70% wt, or 0.1% wt, to 60% wt, or 0.5% wt. to 55% wt., or 1% wt. to 50% wt %, based on the total weight of the sprayable composition.

Embodiment 45. The sprayable composition of embodiment 8, wherein the particles of hydrophobic agent(s), after low energy mixing, have an average particle size in the range between about 5 microns to about 100 microns, or between about 5 microns to about 50 microns.

Embodiment 46. The sprayable composition of embodiment 8, wherein the particles of hydrophobic agent(s), after ultra-high energy mixing, have an average particle size in the range between about 125 nm to about 750 nm, or between about 150 nm to about 500 nm.

Embodiment 47. The sprayable composition of embodiment 1, wherein the aqueous-solute fluid comprises water or a combination of water and one or more polar solute(s).

Embodiment 48. The sprayable composition of embodiment 47, wherein the one or more polar solutes have a water solubility of 0.1% or greater at a temperature of 23° C. and a pressure of 100 kPa (1 bar).

Embodiment 49. The sprayable composition of embodiment 47, wherein the one or more polar solutes have a dielectric constant of greater than 10 at a temperature of 23° C. and a pressure of 100 kPa (1 bar).

Embodiment 50. The sprayable composition of embodiment 47, wherein the one or more polar solutes include, but are not limited to: water soluble solids at a temperature of 23° C. and a pressure of 100 kPa (1 bar), water soluble liquids at a temperature of 23° C. and a pressure of 100 kPa (1 bar), and any derivatives or combinations thereof.

Embodiment 51. The sprayable composition of embodiment 50, wherein the water soluble solids include, but are not limited to: carbohydrates; amino acids, peptides, and proteins; vitamins; minerals; and any derivatives or combinations thereof.

Embodiment 52. The sprayable composition of embodiment 51, wherein the carbohydrates include, but are not limited to: monosaccharides, reduced sugar alcohols, sugar acids, substituted monosaccharides, disaccharides, triglycerides, polysaccharides (glycans), and any derivatives or combinations thereof.

Embodiment 53. The sprayable composition of embodiment 52, wherein the monosaccharides include, but are not limited to: 1, 3-dihydroxy-2-propanone, arabinose, ribose, xylose, lyxose, ribulose, xylulose, psicose, sorbose, tagatose, threose, glucose, fructose, mannose, galactose, allose, altrose, gulose, indose, talose, dihydroxacetone, and any derivatives or combinations thereof.

Embodiment 54. The sprayable composition of embodiment 52, wherein the reduced sugar alcohols include, but are not limited to: threitol, arabitol, xylitol, ribitol, mannitol, sorbitol, galactitol, fucitol, iditol, inositol, volemitol, isomalt, maltitol, lactitol, and any derivatives or combinations thereof.

Embodiment 55. The sprayable composition of embodiment 52, wherein the sugar acids include, but are not limited to: aldonic acids including glyceric acid, xylonic acid, gluconic acid, threonic acid, and ascorbic acid; ulosonic acids including neuraminic acid (5-amino-3,5-dideoxy-D-glycero-D-galacto-non-2-ulosonic acid), and ketodeoxyoctulosonic acid (KDO or 3-deoxy-D-manno-oct-2-ulosonic acid); uronic acids including glucuronic acid, galacturonic acid, lactobionic acid, and iduronic acid; and aldaric acids including tartaric acid, meso-galactaric acid (mucic acid), and D-glucaric acid (saccharic acid); and any derivatives or combinations thereof.

Embodiment 56. The sprayable composition of embodiment 52, wherein the substituted monosaccharides include, but are not limited to sugar esters including phosphate sugar esters, amino sugar esters, acylateD sugar esters, and any derivatives or combinations thereof.

Embodiment 57. The sprayable composition of embodiment 56, wherein the phosphate sugar esters include, but are not limited to glucose-I-phosphate, fructose-1,6-diphosphate, and any derivatives or combinations thereof.

Embodiment 58. The sprayable composition of embodiment 56, wherein the amino sugar esters include, but are not limited to 2-glucosamine, 2-galactosamine, N-acetylglucosamine, N-acetylmannosamine, neuraminic acid, N-acetyltalosaminuronic acid, and any derivatives or combinations thereof.

Embodiment 59. The sprayable composition of embodiment 56, wherein the acylated sugar esters include, but are not limited to methyl-glucoside, muramic acid, N-acetyl-neuraminic acid, N-glycosyl-neuraminic acid, pangamic acid, and any derivatives or combinations thereof.

Embodiment 60. The sprayable composition of embodiment 52, wherein the disaccharides include, but are not limited to sucrose (fructose-glucose), lactose (galactose-glucose), maltose (glucose-glucose), isomaltose, maltobiose, trehalose, cellobiose, and any derivatives or combinations thereof.

Embodiment 61. The sprayable composition of embodiment 52, wherein the triglycerides include, but are not limited to raffinose (glucose-fructose-galactose), melizitose, and any derivatives or combinations thereof.

Embodiment 62. The sprayable composition of embodiment 52, wherein the polysaccharides (glycans) include, but are not limited to starch, glycogen, amylopectin, amylose, cellulose, dextran, chitan, alginic acid, agarose, glycosylaminoglycans including chondroitin sulfate, heparin, hyaluronic acid, dermatan sulfate, keratan sulfate, ascorbic acid (vitamin C), the j-D form of glucuronic acid, and any derivatives or combinations thereof.

Embodiment 63. The sprayable composition of embodiment 51, wherein the amino acids, peptides, and proteins include, but are not limited to: alpha-amino acids including alanine, arginine, asparagine, aspartate, cysteine, glutamate, glutamine, glycine, histidine, isoleucine, leucine, lysine, methionine, phenylalanine, proline, serine, threonine, tryptophan, valine, selenocysteine, pipecolic acid, pyrrolysine, and any derivatives or combinations thereof; beta-amino acids including beta-alanine, beta-aminoisobutyric acid, and any derivatives or combinations thereof; gamma-amino acids including gamma-amino butyric acid, carnitine, and any derivatives or combinations thereof; dipeptides including cysteinyl-thionine, glycyl-glycine, alanyl-histidine, cysteinyl-glycine, and any derivatives or combinations thereof; tripeptides including glutathione, glycyl-glycyl-glycine, lysyl-lysyl-lysine, glutamyl-histeinyl-glycine, and any derivatives or combinations thereof; substituted amino acids and peptides including acetyl carnitine, acetyl cysteine, methylglycinate, glutathione methyl ester, and any derivatives or combinations thereof; proteins including enzymes, cytokines, growth factors, structural proteins such as collagen, elastin, keratin, and any derivatives or combinations thereof.

Embodiment 64. The sprayable composition of embodiment 51, wherein the vitamins include, but are not limited to: vitamin C (ascorbic acid or water soluble derivatives of ascorbic acid), vitamin B1 (thiamin), vitamin B2 (riboflavin), vitamin B3 (niacin), vitamin B5 (pantothenic acid), vitamin B6 (pyridoxin), vitamin B7 (biotin), vitamin B9 (folate), vitamin B12 (cobalamin), and any derivatives or combinations thereof.

Embodiment 65. The sprayable composition of embodiment 51, wherein the minerals include, but are not limited to: aluminum bromide, aluminum chlorate, aluminum chloride, aluminum nitrate, aluminum sulfate, ammonium acetate, ammonium bromide, ammonium carbonate, ammonium chlorate, ammonium chloride, ammonium fluoride, ammonium hydrogen carbonate, ammonium iodide, ammonium nitrate, ammonium phosphate, ammonium sulfate, ammonium sulfide, ammonium sulfite, barium acetate, barium bromide, barium chlorate, barium chloride, barium hydroxide, barium iodide, barium nitrate, barium nitrite, calcium acetate, calcium bromide, calcium chlorate, calcium chloride, calcium iodide, calcium nitrate, calcium nitrite, cobalt (III) acetate, cobalt (III) bromide, cobalt (III) chlorate, cobalt (III) chloride, cobalt (III) iodide, cobalt (III) nitrate, cobalt (III) sulfate, copper (II) acetate, copper (II) bromide, copper (II) chlorate, copper (II) chloride, copper (II) fluoride, copper (II) nitrate, copper (II) sulfate, iron (II) acetate, iron (II) bromide, iron (II) chloride, iron (II) iodide, iron (II) nitrate, iron (II) sulfate, iron (III) bromide, iron (III) chloride, iron (III) iodide, iron (III) nitrate, iron (III) sulfate, lead (II) acetate, lead (II) chlorate, lead (II) nitrate, lead (II) nitrite, lithium acetate, lithium bromide, lithium carbonate, lithium chlorate, lithium chloride, lithium fluoride, lithium hydrogen carbonate, lithium hydroxide, lithium iodide, lithium nitrate, lithium nitrite, lithium sulfate, lithium sulfide, lithium sulfite, magnesium acetate, magnesium bromide, magnesium chlorate, magnesium chloride, magnesium iodide, magnesium nitrate, magnesium nitrite, magnesium sulfate, magnesium sulfite, nickel acetate, nickel bromide, nickel chlorate, nickel chloride, nickel fluoride, nickel iodide, nickel nitrate, nickel sulfate, potassium acetate, potassium bromide, potassium carbonate, potassium chlorate, potassium chloride, potassium fluoride, potassium hydrogen carbonate, potassium hydroxide, potassium iodide, potassium nitrate, potassium nitrite, potassium phosphate, potassium sulfate, potassium sulfide, potassium sulfite, silver chlorate, silver fluoride, silver nitrate, sodium acetate, sodium bromide, sodium carbonate, sodium chlorate, sodium chloride, sodium fluoride, sodium hydrogen carbonate, sodium hydroxide, sodium iodide, sodium nitrate, sodium nitrite, sodium phosphate, sodium sulfate, sodium sulfide, sodium sulfite, zinc acetate, zinc bromide, zinc chlorate, zinc chloride, zinc fluoride, zinc iodide, zinc nitrate, zinc sulfate, and any derivatives or combinations thereof.

Embodiment 66. The sprayable composition of embodiment 50, wherein the water soluble liquids comprise flowable, non-viscous, semi-viscous, or viscous liquids.

Embodiment 67. The sprayable composition of embodiment 50, wherein the water soluble liquids include, but are not limited to: glyceraldehyde, erythrose, erythrulose, sedoheptulose, and any derivatives or combinations thereof.

Embodiment 68. The sprayable composition of embodiment 50, wherein the water soluble liquids comprise water miscible liquids.

Embodiment 69. The sprayable composition of embodiment 68, wherein the water miscible liquids include, but are not limited to: acetaldehyde, acetic acid, acetone, 1,2-butylene glycol, 1,3-butylene glycol, 1,4-butylene glycol, 2-butoxyethanol, dimethyl sulfoxide, ethanol, ethoxydiglycol, triethylene glycol, ethylene glycol, methanol, isopropanol, 1,2-propylene glycol, 1,3-propylene glycol, 1-propanol, propanoic acid, diglycerin, polyglycerol, glycerin, 1,5-pentylene glycol, hexylene glycol, and any derivatives or combinations thereof.

Embodiment 70. The sprayable composition of embodiment 50, wherein at least 10%, or at least 15%, or at least 20%, or at least 25%, of the water soluble liquids comprise water miscible liquids.

Embodiment 71. The sprayable composition of embodiment 1, wherein the water, or combination of water and one or more polar solute(s), is present in an amount from about 5% wt. to about 98% wt., or from about 10% wt. to about 95% wt., or from about 20% wt. to about 95% wt., based on the total weight of the sprayable composition.

Embodiment 72. The sprayable composition of embodiment 8, wherein the one or more additive(s) comprise one or more active or therapeutic ingredient(s); wherein the one or more active or therapeutic ingredient(s) include, but are not limited to: anti-acne agents, antimicrobial agents, anti-inflammatory agents, analgesics, anti-erythemal agents, anti-pruritic agents, antiedemal agents, anti-psoriatic agents, antifungal agents, skin protectants, sunscreen agents, vitamins, antioxidants, anti-irritants, anti-bacterial agents, anti-viral agents, antiaging agents, photoprotection agents, exfoliating agents, wound healing agents, sebum modulators, immunomodulators, hormones, botanicals, moisturizing agents, hand sanitizing agents, astringents, sensates, antibiotics, anesthetics, steroids, tissue healing substances, tissue regenerating substances, amino acids, peptides, minerals, ceramides, hyaluronic acids, skin bleaching ingredients, pre-biotics, probiotics, hemp oils, cannabinoids, and humectants.

Embodiment 73. The sprayable composition of embodiment 72, wherein the one or more additive(s) are present in an amount from about 0.005% wt. to about 90% wt., or from about 0.01% wt. to about 75% wt., based on the total weight of the sprayable composition.

Embodiment 74. The sprayable composition of embodiment 1, which has a viscosity from about 1 cps to about 5000 cps, or from about 5 cps to about 4500 cps, or from about 10 cps to about 4,000 cps, or from about 25 cps to about 3000 cps.

Embodiment 75. The sprayable composition of embodiment 1, which has a viscosity from about 1 cps to about 5000 cps, or from about 2 cps to about 4500 cps, or from about 3 cps to about 4000 cps, or from about 4 cps to about 3500 cps.

Embodiment 76. The sprayable composition of embodiment 1, which has a pH from about 3 to about 9, or from about 3.5 to about 8.5, or from about 4 to about 8.

Embodiment 77. The sprayable composition of embodiment 1, which has a viscosity from about 1 cps to about 2,500 cps, or from about 2 cps to about 2,250 cps, or from about 3 cps to about 2,000 cps, or from about 4 cps to about 1,500 cps.

Embodiment 78. The sprayable composition of embodiment 8, which is post-treated to modify physical, visual, tactile, oral, or olfactory properties.

Embodiment 79. The sprayable composition of embodiment 78, wherein the post-treatment comprises: pH is raised or lowered by the addition of an alkali or acid, respectively; viscosity is increased or decreased by the addition of a thickening agent or salt, respectively; specific gravity is adjusted by the addition of one or more of an antifoam, centrifugation, vacuum, and reduction in viscosity with sweeping mixing; refractive index is adjusted up or down by the addition of a high refractive index solvent/solute or water; or active levels are adjusted by the addition of a hydrophobic active emulsion.

Embodiment 80. The sprayable composition of embodiment 1 for use in one or more of nutritional, pharmaceutical, biomedical, over-the-counter (OTC) drug, cosmetic, food, personal care, animal care, veterinary health, household, and pet care applications.

Embodiment 81. The sprayable composition of embodiment 1 for application to skin, hair or external mucosa, or other surfaces and substrates.

Embodiment 82. The sprayable composition of embodiment 1, which is in the form of a light liquid, a gel, a light lotion, a mist, a light fluid, or a sprayable emollient.

Embodiment 83. The sprayable composition of embodiment 1, which is formulated as a sunscreen spray.

Embodiment 84. A sprayable composition comprising the first emulsion of embodiment 8.

Embodiment 85. A sprayable composition comprising the second emulsion of embodiment 8.

Embodiment 86. The sprayable composition of embodiment 8 wherein the second emulsion is further diluted with additional aqueous-solute fluid to achieve preset or desired aesthetic and performance properties.

Embodiment 87. The sprayable composition of embodiment 8 which is a mixture of two or more second emulsions to achieve preset or desired aesthetic and performance properties.

Embodiment 88. The sprayable composition of embodiment 8 in which one or more of viscosity, pH, specific gravity, refractive index, and active levels in the second emulsion are adjusted to achieve preset or desired aesthetic and performance properties.

Embodiment 89. The sprayable composition of embodiment 8, further comprising adding to the second emulsion one or more rheological modifying agent(s) to adjust viscosity of the second emulsion.

Embodiment 90. The sprayable composition of embodiment 1, wherein the emulsion provides a multifunctional delivery vehicle for active or therapeutic ingredients to a human or animal, said active or therapeutic ingredients including, but not limited to: anti-acne agents, antimicrobial agents, anti-inflammatory agents, analgesics, anti-erythemal agents, antipruritic agents, antiedemal agents, anti-psoriatic agents, antifungal agents, skin protectants, sunscreen agents, vitamins, antioxidants, anti-irritants, anti-bacterial agents, antiviral agents, antiaging agents, photoprotection agents, exfoliating agents, wound healing agents, sebum modulators, immunomodulators, hormones, botanicals, moisturizing agents, hand sanitizing agents, astringents, sensates, antibiotics, anesthetics, steroids, tissue healing substances, tissue regenerating substances, amino acids, peptides, minerals, ceramides, hyaluronic acids, skin bleaching ingredients, pre-biotics, probiotics, hemp oils, cannabinoids, and any derivatives or combinations thereof.

Embodiment 91. The sprayable composition of embodiment 1, wherein the one or more hydrophobic agent(s) comprise edible hydrophobic agent(s).

Embodiment 92. The sprayable composition of embodiment 91, wherein the edible hydrophobic agent(s) include, but are not limited to canola oil, corn oil, cottonseed oil, flaxseed oil, grape seed oil, peanut oil, safflower oil, sesame oil, soybean oil, sunflower oil, walnut oil, olive oil, peppermint oil, orange oil, and any derivatives or mixtures thereof.

Embodiment 93. The sprayable composition of embodiment 1, wherein the one or more nonionic surfactant(s) or emulsifier(s) comprise one or more edible nonionic surfactant(s) or emulsifier(s).

Embodiment 94. The sprayable composition of embodiment 93, wherein the one or more edible surfactants or emulsifiers comprise glyceryl acyloates or polyglyceryl acyloates including, but not limited to polyglyceryl oleate, polyglyceryl-3 oleate, polyglyceryl-4 oleate, polyglyceryl-6 oleate, polyglyceryl caprate, polyglyceryl-2 caprate, polyglyceryl-3 caprate, polyglyceryl-4 caprate, polyglyceryl-6 caprate, polyglyceryl diisostearate, polyglyceryl-2 diisostearate, polyglyceryl-3 diisostearate, polyglyceryl-10 diisostearate, polyglyceryl polyricinoleate, polyglyceryl-3 polyricinoleate, polyglyceryl-6 polyricinoleate, polyglyceryl laurate, polyglyceryl-4 laurate, polyglyceryl-6 laurate, polyglyceryl-10 laurate, polyglyceryl caprylate, polyglyceryl-3 caprylate, polyglyceryl-6 caprylate, polyglyceryl cocoate, polyglyceryl-3 cocoate, polyglyceryl dicaprate, polyglyceryl-6 dicaprate, polyglyceryl polyhydroxystearate, polyglyceryl-6 polyhydroxystearate, polyglyceryl rice branate, polyglyceryl-3 rice branate, polyglyceryl stearate, polyglyceryl-2 stearate, polyglyceryl-3 stearate, polyglyceryl-4 stearate, polyglyceryl-6 stearate, polyglyceryl behenate, polyglyceryl-3 behenate, polyglyceryl-6 behenate, polyglyceryl dioleate, polyglyceryl-10 dioleate, polyglyceryl-10 mono/dioleate, polyglyceryl beeswax, polyglyceryl-3 beeswax, polyglyceryl myristate, polyglyceryl-10 myristate, polyglyceryl octastearate, polyglyceryl-6 octastearate, polyglyceryl decaoleate, polyglyceryl-10 decaoleate, polyglyceryl triisostearate, polyglyceryl-2 triisostearate, polyglyceryl pentaoleate, polyglyceryl-6 pentaoleate, polyglyceryl-10 pentaoleate, polyglyceryl distearate, polyglyceryl-2 distearate, polyglyceryl-3 distearate, polyglyceryl-6 distearate, polyglyceryl diisostearate, polyglyceryl-3 diisostearate, polyglyceryl sesqiisostearate, polyglyceryl-2 sesqiisostearate, polyglyceryl isostearate, polyglyceryl-4 isostearate, polyglyceryl dipolyhydroxystearate, polyglyceryl-2 dipolyhydroxystearate, polyglyceryl sesqioleate, polyglyceryl-2 sesqiolate, polyglyceryl triolivate, polyglyceryl-3 triolivate, polyglyceryl pentaisostearate, polyglyceryl-10 pentaisostearate, polyglyceryl sorbityl linseedate, polyglyceryl-3 sorbityl linseedate, polyglyceryl octadecabehenate/hydroxystearate, polyglyceryl-20 octadecabehenate/hydroxystearate, polyglyceryl methylglucose distearate, polyglyceryl-3 methylglucose distearate, polyglyceryl olivate/polyricinoleate, polyglyceryl-4 olivate/polyricinoleate, polyglyceryl laurate/succinate, polyglyceryl-4 laurate/succinate, polyglyceryl caprate/caprylate/succinate, polyglyceryl-3 caprate/caprylate/succinate, polyglyceryl cetearyl ether olivate, polyglyceryl-3 cetearyl ether olivate, polyglyceryl dimer dilinoleate, polyglyceryl-3 dimer dilinoleate, polyglyceryl diisostearate/polyhydroxystearate/sebacate, polyglyceryl-4 diisostearate/polyhydroxystearate/sebacate, polyglyceryl-10-stearate, polyglyceryl oleyl ether olivate, polyglyceryl-4 oleyl ether olivate, polyglyceryl cetyl ether olivate/succinate, polyglyceryl-3 cetyl ether olivate/succinate, and any derivatives or combinations thereof.

Embodiment 95. The sprayable composition of embodiment 93, wherein the one or more edible surfactants or emulsifiers comprise sucrose acyloates including, but not limited to sucrose palmitate, sucrose cocoate, sucrose stearate, sucrose polystearate, sucrose distearate, sucrose laurate, sucrose dilaurate, sucrose trilaurate, and any derivatives or combinations thereof.

Embodiment 96. The sprayable composition of embodiment 94, wherein the one or more edible glyceryl acyloate or polyglyceryl acyloate surfactants or emulsifiers have an HLB from about 3 to about 20, or from about 7 to about 19, or from about 9 to about 18, or from about 11 to about 17.5, based on the degree of glyceryl units or ethoxyl units, or combinations thereof.

Embodiment 97. The sprayable composition of embodiment 95, wherein the one or more edible sucrose acyloate surfactants or emulsifiers have an HLB from about 2 to about 18, from about 10 to about 17.5, or from about 12 to about 17, or from about 12.5 to about 16, or from about 13 to about 16, based on the degree of glyceryl units or ethoxyl units, or combinations thereof.

Embodiment 98. The sprayable composition of embodiments 94 and 95 wherein the glyceryl acyloate or polyglyceryl acyloate edible surfactants or emulsifiers are present in an amount from about 0.01% wt. to about 10% wt., or from about 0.01% wt. to about 5% wt., or from about 0.05% wt. to about 4.5% wt., or from about 0.1% wt. to about 4% wt., based on the total weight of the sprayable composition; and wherein the sucrose acyloate edible surfactants or emulsifiers are present in an amount from about 0.01% wt. to about 10% wt., or from about 0.1% wt. to about 8% wt., or from about 0.2% wt. to about 7.5% wt., or from about 0.25% wt. to about 5% wt., based on the total weight of the sprayable composition.

Embodiment 99. The sprayable composition of embodiment 8 where a hydrophobic active or therapeutic agent, or combination of hydrophobic active or therapeutic agents, are first dissolved into a second hydrophobic agent, or combination of hydrophobic agents, prior to the premix phase.

Embodiment 100. A sprayable composition comprising:
an emulsion comprising (i) submicron particles of one or more hydrophobic agent(s), (ii) an emulsifier system comprising one or more nonionic surfactant(s) or emulsifier(s), and (iii) an aqueous-solute fluid;
wherein the submicron particles of one or more hydrophobic agent(s) are present in an amount from about 0.01% wt. to about 70% wt., the aqueous-solute fluid is present in an amount from about 1.0% wt. to about 98.5% wt., and the one or more nonionic surfactant(s) or emulsifier(s) are present in an amount from about 0.01% wt. to about 10% wt., all based on the total weight of the sprayable composition;
wherein the submicron particles of one or more hydrophobic agent(s) (i) have an average particle size from about 100 nm to less than about 1000 nm, (ii) have a solubility of less than about 0.1% by weight in water under standard conditions, and (iii) are 85% or more of a size within ±2.0 standard deviations, of the average particle size;
wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and
wherein the one or more nonionic surfactant(s) or emulsifier(s) are sufficient to stabilize the submicron particles of one or more hydrophobic agent(s) in said emulsion, at a level from about 0.05% w/w to about 70% w/w of said one or more hydrophobic agent(s), in said emulsion.

Embodiment 101. A process comprising:
preparing a premix comprising an emulsion comprising (i) one or more hydrophobic agent(s), (ii) an emulsifier system comprising one or more nonionic surfactant(s) or emulsifier(s), (iii) an aqueous-solute fluid, and optionally (iv) one or more additive(s);
subjecting the premix to low energy mixing to form a first emulsion; and
subjecting the first emulsion to ultra-high energy mixing to form a second emulsion;
wherein said second emulsion comprises (i) submicron particles of one or more hydrophobic agent(s), (ii) an emulsifier system comprising one or more nonionic surfactant(s) or emulsifier(s), (iii) an aqueous-solute fluid, and optionally (iv) one or more additive(s); and
wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and
wherein the one or more nonionic surfactant(s) or emulsifier(s) are sufficient to stabilize the submicron particles of one or more hydrophobic agent(s) in the second emulsion, at a level from about 0.05% w/w to about 70% w/w of said one or more hydrophobic agent(s), in the second emulsion.

Embodiment 102. A sprayable composition comprising:
an emulsion comprising (i) submicron particles of one or more hydrophobic agent(s), (ii) an emulsifier system comprising one or more nonionic surfactant(s) or emulsifier(s), (iii) an aqueous-solute fluid, and optionally (iv) one or more additive(s);
wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and
wherein the one or more nonionic surfactant(s) or emulsifier(s) are sufficient to stabilize the submicron particles of one or more hydrophobic agent(s) in the emulsion, at a level from about 0.05% w/w to about 70% w/w of said one or more hydrophobic agent(s), in the emulsion;
said sprayable composition produced by a process comprising:
preparing a premix comprising (i) one or more hydrophobic agent(s), (ii) an emulsifier system comprising one or more nonionic surfactant(s) or emulsifier(s), (iii) an aqueous-solute fluid, and optionally (iv) one or more additive(s);
subjecting the premix to low energy mixing to form a first emulsion; and
subjecting the first emulsion to ultra-high energy mixing to form a second emulsion;
wherein said sprayable composition comprises said second emulsion.

Embodiment 103. A sprayable composition comprising:
an emulsion comprising (i) submicron particles of one or more hydrophobic agent(s), (ii) an emulsifier system comprising one or more nonionic surfactant(s) or emulsifier(s), and (iii) an aqueous-solute fluid;
wherein the submicron particles of one or more hydrophobic agent(s) are present in an amount from about 0.01% wt. to about 70% wt., the aqueous-solute fluid is present in an amount from about 1.0% wt. to about 98.5% wt., and the one or more nonionic surfactant(s) or emulsifier(s) are present in an amount from about 0.01% wt. to about 10% wt., all based on the total weight of the sprayable composition;
wherein the submicron particles of one or more hydrophobic agent(s) (i) have an average particle size from about 100 nm to less than about 1000 nm, (ii) have a solubility of less than about 0.1% by weight in water under standard conditions, and (iii) are 85% or more of a size within ±2.0 standard deviations, of the average particle size; and
wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and wherein the one or more nonionic surfactant(s) or emulsifier(s) are sufficient to stabilize the submicron particles of one or more hydrophobic agent(s) in said emulsion, at a level from about 0.05% w/w to about 70% w/w of said one or more hydrophobic agent(s), in said emulsion;

said sprayable composition produced by a process comprising:

preparing a premix comprising (i) one or more hydrophobic agent(s), (ii) an emulsifier system comprising one or more nonionic surfactant(s) or emulsifier(s), (iii) an aqueous-solute fluid, and optionally (iv) one or more additive(s);

subjecting the premix to low energy mixing to form a first emulsion; and subjecting the first emulsion to ultra-high energy mixing to form a second emulsion;

wherein said sprayable composition comprises said second emulsion.

Embodiment 104. A method of treating disorders of human or animal skin, hair or mucosal tissue, said method comprising:

applying to the skin, hair or external mucosa of a human or animal a sprayable composition comprising:

an emulsion comprising (i) submicron particles of one or more hydrophobic agent(s), (ii) one or more nonionic surfactant(s) or emulsifier(s), and (iii) an aqueous-solute fluid;

wherein the one or more hydrophobic agent(s) comprise one or more active or therapeutic agent(s); and wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and wherein the one or more nonionic surfactant(s) or emulsifier(s) are sufficient to stabilize the submicron particles of one or more hydrophobic agent(s) in said emulsion, at a level from about 0.05% w/w to about 70% w/w of said one or more hydrophobic agent(s), in said emulsion.

Embodiment 105. A method of imparting a desirable tactile, olfactory, or visual property to a skin, hair, or mucosal surface of a human or animal, or other surface or substrate, said method comprising:

applying to the skin, hair or external mucosa of a human or animal, or other surface or substrates, a sprayable composition comprising:

an emulsion comprising (i) submicron particles of one or more hydrophobic agent(s), (ii) an emulsifier system comprising one or more nonionic surfactant(s) or emulsifier(s), and (iii) an aqueous-solute fluid;

wherein the one or more hydrophobic agent(s) comprise one or more aesthetic modifying agent(s); and wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and wherein the one or more nonionic surfactant(s) or emulsifier(s) are sufficient to stabilize the submicron particles of one or more hydrophobic agent(s) in said emulsion, at a level from about 0.05% w/w to about 70% w/w of said one or more hydrophobic agent(s), in said emulsion.

Embodiment 106. A method of delivering one or more active or therapeutic ingredients to a human or animal, said method comprising:

providing an emulsion comprising (i) submicron particles of one or more hydrophobic agent(s), (ii) an emulsifier system comprising one or more nonionic surfactant(s) or emulsifier(s), and (iii) an aqueous-solute fluid;

wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and wherein the one or more nonionic surfactant(s) or emulsifier(s) are sufficient to stabilize the submicron particles of one or more hydrophobic agent(s) in said emulsion, at a level from about 0.05% w/w to about 70% w/w of said one or more hydrophobic agent(s), in said emulsion;

wherein the emulsion acts as a multifunctional delivery vehicle for active or therapeutic ingredients or pre-biotics, and using the multifunctional delivery vehicle to deliver the one or more active or therapeutic ingredients or pre-biotics to a human or animal.

Embodiment 107. The method of embodiment 106, wherein the one or more active or therapeutic ingredients include, but are not limited to: anti-acne agents, antimicrobial agents, anti-inflammatory agents, analgesics, anti-erythemal agents, antipruritic agents, antiedemal agents, anti-psoriatic agents, antifungal agents, skin protectants, sunscreen agents, vitamins, antioxidants, anti-irritants, anti-bacterial agents, antiviral agents, antiaging agents, photo-protection agents, exfoliating agents, wound healing agents, sebum modulators, immunomodulators, hormones, botanicals, moisturizing agents, hand sanitizing agents, astringents, sensates, antibiotics, anesthetics, steroids, tissue healing substances, tissue regenerating substances, amino acids, peptides, minerals, ceramides, hyaluronic acids, skin bleaching ingredients, pre-biotics, probiotics, hemp oils, cannabinoids, and any derivatives or combinations thereof.

Embodiment 108. A method of using a sprayable composition to enhance a physical, chemical, nutritional and/or sensory property of a food, said method comprising:

applying an edible sprayable composition into or onto the food, said edible sprayable composition comprising:

an emulsion comprising (i) submicron particles of one or more edible hydrophobic agent(s), (ii) an emulsifier system comprising one or more edible nonionic surfactants, and (iii) an aqueous-solute fluid;

wherein the one or more edible hydrophobic agent(s) comprise one or more edible active or therapeutic agent(s) and/or one or more edible aesthetic modifying agent(s); and wherein the one or more edible nonionic surfactants comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and wherein the one or more nonionic surfactant(s) or emulsifier(s) are sufficient to stabilize the submicron particles of one or more edible hydrophobic agent(s) in said emulsion, at a level from about 0.05% w/w to about 70% w/w of said one or more hydrophobic agent(s), in said emulsion;

wherein the submicron particles of the one or more edible hydrophobic agent(s) in the emulsion increase an extent of dispersement of the emulsion throughout a water phase of a substrate of the food; and thereby producing a bloom effect distributing the submicron particles of the one or more edible hydrophobic agent(s) uniformly throughout the water phase of the substrate that enhances a physical, chemical, nutritional and/or sensory property of the food.

Embodiment 109. A method of using a sprayable composition to enhance a physical, chemical, nutritional and/or sensory property of a beverage, said method comprising:

applying an edible sprayable composition into the beverage, the edible sprayable composition comprising:

an emulsion comprising (i) submicron particles of one or more edible hydrophobic agent(s), (ii) an emulsifier system comprising one or more edible nonionic surfactants, and (iii) an aqueous-solute fluid;

wherein the one or more edible hydrophobic agent(s) comprise one or more edible active or therapeutic agent(s) and/or one or more edible aesthetic modifying agent(s); and wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and wherein the one or more nonionic surfactant(s) or emulsifier(s) are sufficient to stabilize the submicron particles of one or more edible hydrophobic agent(s) in said emulsion, at a level from about 0.05% w/w to about 70% w/w of said one or more hydrophobic agent(s), in said emulsion;

wherein the submicron particles of the one or more edible hydrophobic agent(s) in the emulsion increase an extent of dispersement of the emulsion throughout a water phase of the beverage; and thereby producing a bloom effect distributing the submicron particles of the one or more edible hydrophobic agent(s) uniformly throughout the water phase of the beverage that enhances a physical, chemical, nutritional and/or sensory property of the beverage.

Embodiment 110. A method of enhancing food, said method comprising:

contacting the food with a sprayable composition comprising:

an emulsion comprising (i) submicron particles of one or more edible hydrophobic agent(s), (ii) an emulsifier system comprising one or more edible nonionic surfactants, and (iii) an aqueous-solute fluid;

wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof; and wherein the one or more nonionic surfactant(s) or emulsifier(s) are sufficient to stabilize the submicron particles of one or more edible hydrophobic agent(s) in said emulsion, at a level from about 0.05% w/w to about 70% w/w of said one or more hydrophobic agent(s), in said emulsion.

Other illustrative embodiments useful in this disclosure are described, for example, in U.S. Pat. Nos. 9,357,770, 9,980,886, and 10,531,674, and also U.S. patent application Ser. Nos. 13/835,642, 16/701,477, and 17/512,251, all of which are incorporated herein by reference in their entirety.

The following embodiments are intended to demonstrate the versatility of submicron hydrophobic agent emulsions of this disclosure. These examples can be utilized as presented or can be diluted in water or water miscible solvent to a concentration that is optimized for a given application. They can also be combined in various ratios to provide multiple benefits to the consumer.

EXAMPLES

General Sprayable Compositions

A sprayable composition formulated as a liquid/toner was prepared and summarized below.

| Phase | Ingredient | Liquid/Toner 10 cts Dimethicone E1 Percentage |
|---|---|---|
| A | Water | 56.12 |
| B | Glycerin | 10.00 |
| A | Phenoxyethanol, Ethylhexylglycerin | 1.00 |
| A | Potassium Sorbate | 0.25 |
| A | Sodium Benzoate | 0.25 |
| C | 10 cst Dimethicone | 30.00 |
| B | Polyglyceryl-10-Diisostearate | 1.71 |
| E | Sucrose Palmitate | 0.57 |
| D | Sodium Hydroxide, Water | 0.10 |
| | Total | 100.00 |

The sprayable composition E1 was prepared in accordance with the processes of this disclosure, in particular, in a main vessel added the ingredients of Phases A and started propeller mixing; added Phase B into Phase A and started heating from 65-70° C.; once batch reached about 70° C., started cooling to about 30° C.; once batch reached about 30° C., moved main vessel to homogenizer and started homogenizing; slowly added premixed Phase C into main vessel and homogenized at high shear; passed 2× through a microfluidizer; adjusted pH between 4.50-6.00 using Phase D; added Phase E into main vessel and mixed until uniform; added Phase F into main vessel and mixed until hydrated; switched to homogenizer and homogenized at high shear until smooth and uniform.

A sprayable composition formulated as a fluid/serum was prepared and summarized below.

| Phase | Ingredient | Fluid/Serum 10 cts Dimethicone E2 Percentage |
|---|---|---|
| A | Water | 58.90 |
| A | Propanediol | 6.00 |
| A | Phenoxyethanol | 1.00 |
| A | Sodium Benzoate | 0.40 |
| C | 10 cst Dimethicone | 30.00 |
| B | Polyglyceryl-10-Diisostearate | 2.00 |
| D | Citric Acid, Water | 0.90 |
| D | Sodium Hydroxide, Water | 0.40 |
| D | Succinoglycan | 0.20 |
| D | Sodium Acrylate/Sodium Acryloyldimethyl Taurate Copolymer (and) C15-19 Alkane (and) Polyglyceryl-6 Laurate (and) Polyglycerin-6 | 0.20 |
| | Total | 100.00 |

The sprayable composition E2 was prepared in accordance with the processes of this disclosure, in particular, in a main vessel added the ingredients of Phase A and started propeller mixing; added Phase B into Phase A slowly and began heating to about 65° C.; premixed Phase C and homogenized; moved main vessel to homogenizer and started homogenizing; slowly added premixed Phase C into main vessel and homogenized at high shear; passed 2× through a microfluidizer; adjusted pH between 5.00-6.00 using Phase D.

A sprayable composition formulated as a spray was prepared and summarized below.

| Phase | Ingredient | Spray 10 cts Dimethicone E3 Percentage |
|---|---|---|
| A | Water | 57.30 |
| A | Propanediol | 6.00 |
| A | Phenoxyethanol | 1.00 |
| A | Sodium Benzoate | 0.40 |
| C | 10 cst Dimethicone | 30.00 |
| B | Polyglyceryl-10-Diisostearate | 3.00 |
| D | Sucrose Palmitate | 1.00 |
| D | Citric Acid, Water | 0.90 |
| D | Sodium Hydroxide, Water | 0.40 |
| | Total | 100.00 |

The sprayable composition E3 was prepared in accordance with the processes of this disclosure, in particular, in a main vessel added the ingredients of Phase A and started propeller mixing; added Phase B into Phase A slowly and began heating to about 65° C.; premixed Phase C and homogenized; moved main vessel to homogenizer and started homogenizing; slowly added premixed Phase C into main vessel and homogenized at high shear; passed 2× through a microfluidizer; adjusted pH between 5.00-6.00 using Phase D.

A sprayable composition formulated as a liquid/toner was prepared and summarized below.

| Phase | Ingredient | Liquid/Toner Caprylic/capric triglyceride E4 Percentage |
|---|---|---|
| A | Water | 57.30 |
| A | Propanediol | 6.00 |
| A | Phenoxyethanol | 1.00 |
| A | Sodium Benzoate | 0.40 |
| B | Polyglyceryl-10-Diisostearate | 3.00 |
| E | Sucrose Palmitate | 1.00 |
| C | Caprylic/capric triglyceride | 30.00 |
| D | Citric Acid, Water | 0.90 |
| D | Sodium Hydroxide, Water | 0.40 |
| | Total | 100.00 |

The sprayable composition E4 was prepared in accordance with the processes of this disclosure, in particular, in a main vessel added the ingredients of Phase A and started propeller mixing; added Phase B into Phase A and started heating from 65-70° C.; once batch reached about 70° C., started cooling to about 30° C.; once batch reached about 30° C., moved main vessel to homogenizer and started homogenizing; slowly added premixed Phase C into main vessel and homogenized at high shear; passed 2× through a microfluidizer; adjusted pH between 4.50-6.00 using Phase D; added Phase E into main vessel and mixed until uniform; added Phase F into main vessel and mixed until hydrated; switched to homogenizer and homogenized at high shear until smooth and uniform.

A sprayable composition formulated as a fluid/serum was prepared and summarized below.

| Phase | Ingredient | Fluid/Serum Caprylic/capric E5 Percentage |
|---|---|---|
| A | Water | 58.90 |
| A | Propanediol | 6.00 |
| A | Phenoxyethanol | 1.00 |
| A | Sodium Benzoate | 0.40 |
| B | Polyglyceryl-10-Diisostearate | 2.00 |
| C | Caprylic/capric triglyceride | 30.00 |
| D | Citric Acid, Water | 0.90 |
| D | Sodium Hydroxide, Water | 0.40 |
| E | Succinoglycan | 0.20 |
| E | Sodium Acrylate/Sodium Acryloyldimethyl Taurate Copolymer (and) C15-19 Alkane (and) Polyglyceryl-6 Laurate (and) Polyglycerin-6 | 0.20 |
| | Total | 100.00 |

The sprayable composition E5 was prepared in accordance with the processes of this disclosure, in particular, in a main vessel added the ingredients of Phases A and started propeller mixing; added Phase B into Phase A and started heating from 65-70° C.; once batch reached about 70° C., started cooling to about 30° C.; once batch reached about 30° C., moved main vessel to homogenizer and started homogenizing; slowly added premixed Phase C into main vessel and homogenized at high shear; passed 2× through a microfluidizer; adjusted pH between 4.50-6.00 using Phase D; added Phase E into main vessel and mixed until uniform; added Phase F into main vessel and mixed until hydrated; switched to homogenizer and homogenized at high shear until smooth and uniform.

A sprayable composition formulated as a spray was prepared and summarized below.

| Phase | Ingredient | Spray Caprylic/capric triglyceride E6 Percentage |
|---|---|---|
| A | Water | 57.30 |
| A | Propanediol | 6.00 |
| A | Phenoxyethanol | 1.00 |
| A | Sodium Benzoate | 0.40 |
| B | Polyglyceryl-10-Diisostearate | 3.00 |
| E | Sucrose Palmitate | 1.00 |
| C | Caprylic/capric triglyceride | 30.00 |
| D | Citric Acid, Water | 0.90 |
| D | Sodium Hydroxide, Water | 0.40 |
| | Total | 100.00 |

The sprayable composition E6 was prepared in accordance with the processes of this disclosure, in particular, in a main vessel added the ingredients of Phases A and started propeller mixing; added Phase B into Phase A and started heating from 65-70° C.; once batch reached about 70° C., started cooling to about 30° C.; once batch reached about 30° C., moved main vessel to homogenizer and started homogenizing; slowly added premixed Phase C into main vessel and homogenized at high shear; passed 2× through a microfluidizer; adjusted pH between 4.50-6.00 using Phase D; added Phase E into main vessel and mixed until uniform; added Phase F into main vessel and mixed until hydrated; switched to homogenizer and homogenized at high shear until smooth and uniform.

A sprayable composition formulated as a liquid/toner was prepared and summarized below.

| Phase | Ingredient | Liquid/Toner Olive Oil E7 Percentage |
|---|---|---|
| A | Water | 57.30 |
| A | Propanediol | 6.00 |
| A | Phenoxyethanol | 1.00 |
| A | Sodium Benzoate | 0.40 |
| B | Polyglyceryl-10-Diisostearate | 3.00 |
| D | Sucrose Palmitate | 1.00 |
| C | Olive Oil | 30.00 |
| D | Citric Acid, Water | 0.90 |
| D | Sodium Hydroxide, Water | 0.40 |
| | Total | 100.00 |

The sprayable composition E7 was prepared in accordance with the processes of this disclosure, in particular, in a main vessel added the ingredients of Phase A and started propeller mixing; added Phase B into Phase A; premixed Phase C and homogenized; moved main vessel to homogenizer and started homogenizing; passed 2× through a microfluidizer; adjusted pH between 6.85-7.5 using Phase D.

A sprayable composition formulated as a fluid/serum was prepared and summarized below.

| Phase | Ingredient | Fluid/Serum Olive Oil E8 Percentage |
|---|---|---|
| A | Water | 58.80 |
| A | Propanediol | 6.00 |
| A | Phenoxyethanol | 1.00 |
| A | Sodium Benzoate | 0.40 |
| B | Polyglyceryl-10-Diisostearate | 2.00 |
| C | Olive Oil | 30.00 |
| D | Citric Acid, Water | 0.90 |
| D | Sodium Hydroxide, Water | 0.40 |
| E | Succinoglycan | 0.30 |
| E | Sodium Acrylate/Sodium Acryloyldimethyl Taurate Copolymer (and) C15-19 Alkane (and) Polyglyceryl-6 Laurate (and) Polyglycerin-6 | 0.20 |
| | Total | 100.00 |

The sprayable composition E8 was prepared in accordance with the processes of this disclosure, in particular, in a main vessel added the ingredients of Phase A and started propeller mixing; added Phase B into Phase A and started heating from 65-70° C.; once batch reached about 70° C., started cooling to about 30° C.; once batch reached about 30° C., moved main vessel to homogenizer and started homogenizing; slowly added premixed Phase C into main vessel and homogenized at high shear; passed 2× through a microfluidizer; adjusted pH between 4.50-6.00 using Phase D; added Phase E into main vessel and mixed until uniform; added Phase F into main vessel and mixed until hydrated; switched to homogenizer and homogenized at high shear until smooth and uniform.

A sprayable composition formulated as a spray was prepared and summarized below.

| Phase | Ingredient | Spray Olive Oil E9 Percentage |
|---|---|---|
| A | Water | 57.30 |
| A | Propanediol | 6.00 |
| A | Phenoxyethanol | 1.00 |
| A | Sodium Benzoate | 0.40 |
| B | Polyglyceryl-10-Diisostearate | 3.00 |
| D | Sucrose Palmitate | 1.00 |
| C | Olive Oil | 30.00 |
| D | Citric Acid, Water | 0.90 |
| D | Sodium Hydroxide, Water | 0.40 |
| | Total | 100.00 |

The sprayable composition E9 was prepared in accordance with the processes of this disclosure, in particular, in a main vessel added the ingredients of Phase A and started propeller mixing; added Phase B into Phase A; premixed Phase C and homogenized; moved main vessel to homogenizer and started homogenizing; slowly added premixed Phase C into main vessel and homogenized at high shear; passed 2× through a microfluidizer; adjusted pH between 6.85-7.5 using Phase D.

A sprayable composition formulated as a liquid/toner was prepared and summarized below.

| Phase | Ingredient | Liquid/Toner C12-15 Alkyl Benzoate E10 Percentage |
|---|---|---|
| A | Water | 58.82 |
| D | Xanthan Gum | 0.40 |
| C | Benzyl Alcohol | 1.00 |
| A | Glycerin | 7.50 |
| A | Polyglyceryl-10-Diisostearate | 1.71 |
| B | Sucrose Palmitate | 0.57 |
| C | C12-15 Alkyl Benzoate | 30.00 |
| | Total | 100.00 |

The sprayable composition E10 was prepared in accordance with the processes of this disclosure, in particular, combined Phase A into a main vessel and started heating to 65-70° C.; polyglyceryl-10-diisostearate dissolved after temperature reached and sits at 65-70° C. for some time; once fully dissolved, switched to homogenizer and slowly added Phase B; let batch cool to 30-35° C.; once at 30° C., added Phase C slowly under homogenization and homogenized at high shear 5,000-6,000 rpm; ran 2 passes in a microfluidizer; added Phase D with propeller mixing, and mixed until completely uniform and wet out.

A sprayable composition formulated as a fluid/serum was prepared and summarized below.

| Phase | Ingredient | Fluid/Serum C12-15 Alkyl Benzoate E11 Percentage |
|---|---|---|
| B | Water | 58.30 |
| C | Xanthan Gum | 0.70 |
| B | Benzyl Alcohol | 1.00 |
| A | Sodium Methyl Cocoyl Taurate | 10.00 |
| B | Glycerin | 5.00 |
| A | C12-15 Alkyl Benzoate | 25.00 |
| | Total | 100.00 |

The sprayable composition E11 was prepared in accordance with the processes of this disclosure, in particular, warmed/heated Phase A together to 60° C.-65° C. while mixing; added glycerin; mixed well; added water, benzyl alcohol, and mixed; processed Phase AB through microfluidizer 2 passes; sifted xanthan gum; hydrated by mixing 30-45 min; homogenized at slow speed for 10 min.

A sprayable composition formulated as a spray was prepared and summarized below.

| Phase | Ingredient | Spray C12-15 Alkyl Benzoate E12 Percentage |
|---|---|---|
| A | Water | 58.82 |
| D | Xanthan Gum | 0.40 |
| C | Benzyl Alcohol | 1.00 |
| A | Glycerin | 7.50 |
| A | Polyglyceryl-10-Diisostearate | 1.71 |
| B | Sucrose Palmitate | 0.57 |
| C | C12-15 Alkyl Benzoate | 30.00 |
| | Total | 100.00 |

The sprayable composition E12 was prepared in accordance with the processes of this disclosure, in particular, combined Phase A into a main vessel and started heating to 65-70° C.; polyglyceryl-10-diisostearate dissolved after temperature reached and sits at 65-70° C. for some time; once fully dissolved, switched to homogenizer and slowly added Phase B; let batch cool to 30-35° C.; once at 30° C., added Phase C slowly under homogenization and homogenized at high shear 5,000-6,000 rpm; ran 2 passes in a microfluidizer; added Phase D with propeller mixing, and mixed until completely uniform and wet out.

A sprayable composition formulated as a liquid/toner was prepared and summarized below.

| Phase | Ingredient | Liquid/Toner Chemical UV filters E13 Percentage |
|---|---|---|
| B | Water | 9.50 |
| B | Propanediol | 5.00 |
| B | Phenoxyethanol | 0.45 |
| C | Sucrose Palmitate | 0.05 |
| A | Isosorbide Dicaprylate & Butyl Methoxydibenzoylmethane & Homosalate & Octocrylene & Ethylhexyl Salicylate & Butyloctyl Salicylate & Polyglyceryl-10 Diisostearate & Water & Phenoxyethanol & Sucrose Palmitate (B6) | 85.00 |
| | Total | 100.00 |

The sprayable composition E13 was prepared in accordance with the processes of this disclosure, in particular, added Phase A to a main vessel; propeller mixed in Phase B one at a time; started homogenizer small hole high shear and sifted in Phase C; homogenized until uniform.

A sprayable composition formulated as a fluid/serum was prepared and summarized below.

| Phase | Ingredient | Fluid/Serum Chemical UV filters E14 Percentage |
|---|---|---|
| B | Water | 33.75 |
| B | Propanediol | 6.00 |
| B | Sodium Benzoate | 0.30 |
| B | 10 cst Dimethicone | 0.50 |
| C | Cetearyl alcohol | 0.50 |
| E | Hydroxyethyl Acrylate/Sodium Acryloyldimethyl Taurate Copolymer | 0.10 |
| E | Ammonium Acryloyldimethyltaurate/VP Copolymer | 0.25 |
| D | Water (and) Camellia Sinensis Leaf Extract (and) Ipomoea Batatas Root Extract (and) Oryza Sativa (Rice) Hull Extract (and) Lactobacillus Ferment Lysate (and) Saccharomyces Lysate (and) Hydroxyacetophenone (and) Sodium Benzoate (and) Caprylyl Glycol | 1.00 |
| A | Water & Phenoxyethanol & Acrylates/C10-30 Alkyl Acrylate Crosspolymer & Polyglyceryl-10-Diisostearate & Sucrose Palmitate & Coconut alkanes & Coco-Caprylate/Caprate & Polyhydroxystearic Acid & Butyloctyl Salicylate & Zinc Oxide & Triethoxycaprylylsilane (B4) | 57.60 |
| | Total | 100.00 |

The sprayable composition E14 was prepared in accordance with the processes of this disclosure, in particular, added Phase A to a main vessel and started propeller mixing; started heating batch 60-65° C.; added Phase B one by one to main vessel; added Phase C; maintained batch at 60-65° C.; once Phase C was fully dissolved, started cooling batch to 30° C.; once batch reached 30° C., added Phase D; slowly sifted in Phase E one by one; mixed and hydrated; switched main vessel to small-holed stator high shear homogenizer and homogenized for about 5 min at 4,000-5,000 rpm.

A sprayable composition formulated as a spray was prepared and summarized below.

| Phase | Ingredient | Spray Chemical UV filters E15 Percentage |
|---|---|---|
| B | Water | 6.20 |
| B | Propanediol | 5.50 |
| B | Phenoxyethanol | 0.50 |
| C | Sucrose Palmitate | 0.05 |
| A | Water & Phenoxyethanol & Polyglyceryl-10-Diisostearate & Sucrose Palmitate & Coconut alkanes & Coco-Caprylate/Caprate & Polyhydroxystearic Acid & Butyloctyl Salicylate & Zinc Oxide & Triethoxycaprylylsilane (B5) | 87.75 |
| | Total | 100.00 |

The sprayable composition E15 was prepared in accordance with the processes of this disclosure, in particular, combined Phase A into a main vessel and started propeller mixing; added Phase B one by one to main vessel; switched to homogenizer and using small hole stator, homogenized at high shear; slowly added Phase C to main vessel and continued homogenizing.

A sprayable composition formulated as a spray was prepared and summarized below.

| Phase | Ingredient | Spray Chemical UV filters E16 Percentage |
|---|---|---|
| B | Water | 9.50 |
| B | Propanediol | 5.00 |
| B | Phenoxyethanol | 0.45 |
| C | Sucrose Palmitate | 0.05 |
| A | Isosorbide Dicaprylate & Butyl Methoxydibenzoylmethane & Homosalate & Octocrylene & Ethylhexyl Salicylate & Butyloctyl Salicylate & Polyglyceryl-10 Diisostearate & Water & Phenoxyethanol & Sucrose Palmitate (B6) | 85.00 |
| Total | | 100.00 |

The sprayable composition E16 was prepared in accordance with the processes of this disclosure, in particular, added Phase A to a main vessel; propeller mixed in Phase B one at a time; started homogenizer small hole high shear and sifted in Phase C; homogenized until uniform.

A sprayable composition formulated as a spray was prepared and summarized below.

| Phase | Ingredient | Spray Furniture Polish E17 Percentage |
|---|---|---|
| A | Water | 57.30 |
| A | Propanediol | 6.00 |
| A | Phenoxyethanol | 1.00 |
| A | Sodium Benzoate | 0.40 |
| C | Dimethicone- High Viscosity Silicone (Gransil 530) | 10.00 |
| C | 10 cst Dimethicone | 20.00 |
| B | Polyglyceryl-10-Diisostearate | 3.00 |
| E | Sucrose Palmitate | 1.00 |
| D | Citric Acid, Water | 0.90 |
| D | Sodium Hydroxide, Water | 0.40 |
| | Total | 100.00 |

The sprayable composition E17 was prepared in accordance with the processes of this disclosure, in particular, in a main vessel added the ingredients of Phase A and started propeller mixing; added Phase B into Phase A slowly and began heating to about 65 C; premixed Phase C and homogenized; moved main vessel to homogenizer and started homogenizing; slowly added premixed Phase C into main vessel and homogenized at high shear; passed 2× through a microfluidizer; adjusted pH between 5.00-6.00 using Phase D; added Phase E and homogenized at high shear for about 5 mW.

A sprayable composition formulated as a spray was prepared and summarized below.

| Phase | Ingredient | Spray Furniture Polish E18 Percentage |
|---|---|---|
| A | Water | 54.65 |
| B | Denatured Alcohol SDA 40-B 190 Proof | 20.00 |
| E | Dimethyl Isosorbide | 5.00 |
| E | Lidocaine | 2.00 |
| E | Menthol | 0.50 |
| B | Acrylates/C10-30 Alkyl Acrylate Crosspolymer | 0.25 |
| B | Pentylene Glycol | 5.00 |
| B | Glycerin | 2.00 |
| A | Potassium Sorbate | 0.25 |
| A | Sodium Benzoate | 0.25 |
| D | Aminomethyl Propanol | 0.10 |
| C | Water (and) Glycerin (and) Sucrose Palmitate (and) C12-15 Alkyl Benzoate (and) Benzyl Alcohol (and) Xanthan Gum (B1) | 10.00 |
| | Total | 100.00 |

The sprayable composition E18 was prepared in accordance with the processes of this disclosure, in particular, in a main vessel added the ingredients of Phase A and started propeller mixing; added Phase B into Phase A slowly and began heating to about 65° C.; premixed Phase C and homogenized; moved main vessel to homogenizer and started homogenizing; slowly added premixed Phase C into main vessel and homogenized at high shear; passed 2× through a microfluidizer; adjusted pH between 5.00-6.00 using Phase D; added Phase E and homogenized at high shear for about 5 min.

General Dispersions

A dispersion was prepared for use in the sprayable compositions of this disclosure and summarized below.

| | Dispersion Identification | |
|---|---|---|
| Phase | Formula Number<br>Ingredient | B1<br>Percentage |
| A | Water | 58.82 |
| A | Glycerin | 7.50 |
| D | Xanthan Gum | 0.40 |
| C | Benzyl Alcohol | 1.00 |
| B | Sucrose Palmitate | 2.28 |
| C | C12-15 Alkyl Benzoate | 30.00 |
| | Total | 100.00 |

The dispersion B1 was prepared in accordance with the processes of this disclosure, in particular, premixed Phase B and added to D.I. water; mixed 10 min; added Phase C to Phase AB; mixed 2-3 min; homogenized; ran 2 passes in a microfluidizer; added Phase D with propeller mixing, and mixed until completely uniform and wet out.

A dispersion was prepared for use in the sprayable compositions of this disclosure and summarized below.

| | Dispersion Identification | |
|---|---|---|
| Phase | Formula Number<br>Ingredient | B2<br>Percentage |
| A | Glycerin | 54.115 |
| B | Titanium Dioxide | 12.988 |
| C | Bentonite | 7.794 |
| D | Kaolin | 25.103 |
| | Total | 100.000 |

The dispersion B2 was prepared in accordance with the processes of this disclosure, in particular, heated glycerine to 70° C.-85° C.; added each ingredient in listed order while homogenizing; added ImerCare 08K by portions; milled well before adding next portion of powder; homogenized well; cooled under regular propeller mixing.

A dispersion was prepared for use in the sprayable compositions of this disclosure and summarized below.

| | Dispersion Identification | |
|---|---|---|
| Phase | Formula Number<br>Ingredient | B3<br>Percentage |
| A | Water | 58.82 |
| A | Glycerin | 7.50 |
| D | Xanthan Gum | 0.40 |
| C | Benzyl Alcohol | 1.00 |
| A | Polyglyceryl-10-Diisostearate | 1.71 |
| B | Sucrose Palmitate | 0.57 |
| C | C12-15 Alkyl Benzoate | 30.00 |
| | Total | 100.00 |

The dispersion B3 was prepared in accordance with the processes of this disclosure, in particular, combined Phase A into a main vessel and started heating to 65-70° C.; polyglyceryl-10-diisostearate dissolved after temperature reached and sits at 65-70° C. for some time; once fully dissolved, switched to homogenizer and slowly added Phase B; let batch cool to 30-35° C.; once at 30° C., added Phase C slowly under homogenization and homogenized at high shear 5,000-6,000 rpm; ran 2 passes in a microfluidizer; added Phase D with propeller mixing, and mixed until completely uniform and wet out.

A dispersion was prepared for use in the sprayable compositions of this disclosure and summarized below.

| | Dispersion Identification | |
|---|---|---|
| Phase | Formula Number<br>Ingredient | B4<br>Percentage |
| A | Water | 38.86 |
| A | Phenoxyethanol | 1.03 |
| A | Polyglyceryl-10-Diisostearate | 2.28 |
| B | Sucrose Palmitate | 0.74 |
| A | Acrylates/C10-30 Alkyl Acrylate Crosspolymer | 0.11 |
| C | Zinc Oxide, Coconut Alkanes, Coco-Caprylate/Caprate, Polyhydroxystearic Acid, Triethoxycaprylylsilane, Butyloctyl Salicylate | 56.98 |
| | Total | 100.00 |

The dispersion B4 was prepared in accordance with the processes of this disclosure, in particular, combined Phase A into a main vessel and started heating to 65-70° C.; polyglyceryl-diisostearate dissolved after temperature reached and sits at 65-70 C for some time; once fully dissolved, switched to homogenizer and slowly added Phase B; let batch cool to 40-45° C.; once at 30° C., added Phase C slowly under homogenization and homogenized at high shear 5,000-6,000 rpm; ran 2 passes in a microfluidizer.

A dispersion was prepared for use in the sprayable compositions of this disclosure and summarized below.

| | Dispersion Identification | |
|---|---|---|
| Phase | Formula Number<br>Ingredient | B5<br>Percentage |
| A | Water | 40.29 |
| A | Phenoxyethanol | 0.45 |
| A | Polyglyceryl-10-Diisostearate | 1.71 |
| B | Sucrose Palmitate | 0.57 |
| C | Zinc Oxide, Coconut Alkanes, Coco-Caprylate/Caprate, Polyhydroxystearic Acid, Triethoxycaprylylsilane, Butyloctyl Salicylate | 56.98 |
| | Total | 100.00 |

The dispersion B5 was prepared in accordance with the processes of this disclosure, in particular, combined Phase A into a main vessel and started heating to 65-70° C.; polyglyceryl-10-diisostearate dissolved after temperature reached and sits at 65-70° C. for some time; once fully dissolved, switched to homogenizer and slowly added Phase B; let batch cool to 40-45° C.; once at 30° C., added Phase C slowly under homogenization and homogenized at high shear 5,000-6,000 rpm; ran 2 passes in a microfluidizer.

A dispersion was prepared for use in the sprayable compositions of this disclosure and summarized below.

| | Dispersion Identification | |
|---|---|---|
| Phase | Formula Number<br>Ingredient | B6<br>Percentage |
| C | Water | 54.70 |
| C | Phenoxyethanol | 0.45 |
| B | Polyglyceryl-10-Diisostearate | 1.50 |
| D | Sucrose Palmitate | 0.40 |
| A | Butyloctyl Salicylate | 5.88 |
| A | Isosorbide Dicaprylate | 10.01 |
| A | Butyl Methoxydibenzoylmethane | 3.53 |

-continued

| Phase | Dispersion Identification Formula Number Ingredient | B6 Percentage |
|---|---|---|
| A | Homosalate | 11.76 |
| A | Octocrylene | 5.88 |
| A | Ethylhexyl Salicylate | 5.88 |
|   | Total | 100.00 |

The dispersion B6 was prepared in accordance with the processes of this disclosure, in particular, combined Phase D into side kettle and started heating to 65-70° C.; once the batch turned clear and uniform, added Phase B and continued propeller mixing until dissolved; started cooling side kettle to 30° C.; in a main vessel, combined Phase C; started homogenizing and slowly sifted in Phase D into side kettle; once side kettle reached 30° C., slowly added side kettle into main vessel and continued to homogenize; homogenized using small holed stator at high shear 4,000-5,000 rpm for about 5 min until uniform; ran 2× passes in a microfluidizer.

Sprayable compositions of this disclosure were prepared by a process that involved preparing a premix containing (i) one or more hydrophobic agent(s), (ii) an emulsifier system having one or more nonionic surfactant(s) or emulsifier(s), (iii) an aqueous-solute fluid, and optionally (iv) one or more additive(s); subjecting the premix to low energy mixing to form a first emulsion; and subjecting the first emulsion to ultra-high energy mixing to form a second emulsion. FIG. 1 depicts an illustrative process flow diagram for preparing the sprayable compositions of this disclosure.

FIG. 2 shows the product type and hydrophobe for emulsion sprayable compositions of this disclosure, in accordance with the Examples.

What is claimed is:
1. A sprayable composition comprising:
  (i) a concentrated emulsion comprising:
    (a) submicron particles of one or more hydrophobic agent(s);
    (b) an emulsifier system comprising one or more nonionic surfactant(s) or emulsifier(s);
    (c) an aqueous-solute fluid; and
    (d) optionally one or more additives or adjuvants,
  wherein the submicron particles of one or more hydrophobic agent(s) are present in the concentrated emulsion in an amount from about 0.01% wt. to about 70% wt., the aqueous-solute fluid is present in an amount from about 1.0% wt. to about 98.5% wt., and the one or more nonionic surfactant(s) or emulsifier(s) are present in an amount from about 0.01% wt. to about 10% wt., all based on the total weight of the concentrated emulsion;
  wherein the submicron particles of one or more hydrophobic agent(s) in the concentrated emulsion have an average particle size from about 100 nm to less than about 1000 nm, have a solubility of less than about 0.1% by weight in water under standard conditions, and are 85% or more of a size within ±2.0 standard deviations, of the average hydrophobic agent(s) particle size of the concentrated emulsion;
  wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof;
  wherein the one or more nonionic surfactant(s) or emulsifier(s) are sufficient to stabilize the submicron particles of one or more hydrophobic agent(s) in said concentrated emulsion, at a level from about 0.05% w/w to about 70% w/w of said one or more hydrophobic agent(s), in said concentrated emulsion;
  wherein the concentrated emulsion is prepared by a process comprising:
    preparing a first emulsion comprising one or more hydrophobic agent(s), an emulsifier system comprising one or more nonionic surfactant(s) or emulsifier(s), an aqueous-solute fluid, and optionally one or more additive(s);
    subjecting the first emulsion to low energy mixing, wherein the low energy mixing is mechanical; and
    subjecting the first emulsion to ultra-high energy mixing to form a second emulsion, wherein the ultra-high energy mixing is non-mechanical;
    wherein the second emulsion comprises said concentrated emulsion; and
    wherein the submicron particles of one or more hydrophobic agent(s) possess a net negative charge after the non-mechanical ultra-high energy mixing, wherein the absolute value of the negative charge is at least 30 mV;
  (ii) water;
  (iii) one or more rheological modifying agents; and
  (iv) optionally one or more other additives or adjuvants;
  wherein the sprayable composition has a viscosity sufficient to form of preset of desired droplet size upon dispensing from a spray dispenser, and
  wherein the sprayable composition is stable for a commercially viable period of time.

2. The sprayable composition of claim 1 wherein, in the concentrated emulsion, the submicron particles of one or more hydrophobic agent(s) are 85% or more of a size within ±1.9 standard deviations, or within ±1.8 standard deviations, or within ±1.7 standard deviations, or within ±1.6 standard deviations, or within ±1.5 standard deviations, of the average hydrophobic agent(s) particle size of the concentrated emulsion.

3. The sprayable composition of claim 1, wherein, in the concentrated emulsion, the ester(s) of one or more fatty acid moieties with one or more hydroxyl groups of glycerol or polyglycerol surfactants or emulsifiers comprise glyceryl acyloates or polyglyceryl acyloates selected from the group consisting of polyglyceryl oleate, polyglyceryl-3 oleate, polyglyceryl-4 oleate, polyglyceryl-6 oleate, polyglyceryl caprate, polyglyceryl-2 caprate, polyglyceryl-3 caprate, polyglyceryl-4 caprate, polyglyceryl-6 caprate, polyglyceryl diisostearate, polyglyceryl-2 diisostearate, polyglyceryl-3 diisostearate, polyglyceryl-10 diisostearate, polyglyceryl polyricinoleate, polyglyceryl-3 polyricinoleate, polyglyceryl-6 polyricinoleate, polyglyceryl laurate, polyglyceryl-4 laurate, polyglyceryl-6 laurate, polyglyceryl-10 laurate, polyglyceryl caprylate, polyglyceryl-3 caprylate, polyglyceryl-6 caprylate, polyglyceryl cocoate, polyglyceryl-3 cocoate, polyglyceryl dicaprate, polyglyceryl-6 dicaprate, polyglyceryl polyhydroxystearate, polyglyceryl-6 polyhydroxystearate, polyglyceryl rice branate, polyglyceryl-3 rice branate, polyglyceryl stearate, polyglyceryl-2 stearate, polyglyceryl-3 stearate, polyglyceryl-4 stearate, polyglyceryl-6 stearate, polyglyceryl behenate, polyglyceryl-3 behenate, polyglyceryl-6 behenate, polyglyceryl dioleate, polyglyceryl-10 dioleate, polyglyceryl-10 mono/dioleate, polyglyceryl beeswax, polyglyceryl-3 beeswax, polyglyceryl myristate, polyglyceryl-10 myristate, polyglyceryl octastearate, polyglyceryl-6 octastearate, polyglyceryl decaoleate, polyglyceryl-10 decaoleate, polyglyceryl triisostearate, polyglyceryl-2 triisostearate, polyglyceryl pentaoleate, polyglyceryl-6 pentaoleate, polyglyceryl-10 pentaoleate, polyglyceryl distearate, polyglyceryl-2 distearate, polyglyceryl-3 distearate, polyglyceryl-6 distearate, polyglyceryl diisostearate, polyglyceryl-3 diisostearate, polyglyceryl sesqiisostearate, polyglyceryl-2 sesqiisostearate, polyglyceryl isostearate, polyglyceryl-4 isostearate, polyglyceryl dipolyhydroxystearate, polyglyceryl-2 dipolyhydroxystearate, polyglyceryl sesqioleate, polyglyceryl-2 sesqiolate, polyglyceryl triolivate, polyglyceryl-3 triolivate, polyglyceryl pentaisostearate, polyglyceryl-10 pentaisostearate, polyglyceryl sorbityl linseedate, polyglyceryl-3 sorbityl linseedate, polyglyceryl octadecabehenate/hydroxystearate, polyglyceryl-20 octadecabehenate/hydroxystearate, polyglyceryl methylglucose distearate, polyglyceryl-3 methylglucose distearate, polyglyceryl olivate/polyricinoleate, polyglyceryl-4 olivate/polyricinoleate, polyglyceryl laurate/succinate, polyglyceryl-4 laurate/succinate, polyglyceryl caprate/caprylate/succinate, polyglyceryl-3 caprate/caprylate/succinate, polyglyceryl cetearyl ether olivate, polyglyceryl-3 cetearyl ether olivate, polyglyceryl dimer dilinoleate, polyglyceryl-3 dimer dilinoleate, polyglyceryl diisostearate/polyhydroxystearate/sebacate, polyglyceryl-4 diisostearate/polyhydroxystearate/sebacate, polyglyceryl-10-stearate, polyglyceryl oleyl ether olivate, polyglyceryl-4 oleyl ether olivate, polyglyceryl cetyl ether olivate/succinate, polyglyceryl-3 cetyl ether olivate/succinate, and any derivatives or combinations thereof, and wherein the ester(s) of one or more fatty acid moieties with one or more hydroxyl groups of sucrose surfactants or emulsifiers comprise sucrose acyloates selected from the group consisting of sucrose palmitate, sucrose cocoate, sucrose stearate, sucrose polystearate, sucrose distearate, sucrose laurate, sucrose dilaurate, sucrose trilaurate, and any derivatives or combinations thereof.

4. The sprayable composition of claim 1, wherein, in the concentrated emulsion, the one or more hydrophobic agent(s) are at least one selected from the group consisting of: mono, di, tri, or poly alkyl (or alkenyl) esters, ethers, acetals and hemiacetals of a di-, tri-, or polyhydroxy compound, and any derivatives or combinations thereof; saturated and unsaturated, linear and branched natural or vegetable oils selected from the group consisting of soybean oil, almond oil, castor oil, canola oil, cottonseed oil, grapeseed oil, rice bran oil, palm oil, coconut oil, palm kernel oil, olive oil, linseed oil, sunflower oil, safflower oil, peanut oil, corn oil, and any derivatives or combinations thereof; water insoluble silicone materials selected from the group consisting of polyalkylsiloxanes, polyarylsiloxanes, polyalkylarylsiloxanes, polysiloxane gums, polyethersiloxane copolymers, silicone crosspolymers, and any derivatives or combinations thereof; water insoluble materials selected from the group consisting of diglycerides, triglycerides, lauramine oleate, isopropyl palmitate, mineral oil, petrolatum, and any derivatives or combinations thereof; and hemp oil and cannabinoids selected from the group consisting of cannabidiol (CBD), delta-9-tetrahydrocannabinol (THC), cannabinol (CBN), cannabigerol (CBG), cannabichromene oil (CBC), any hemp oil or cannabinoid species, and any derivatives or combinations thereof.

5. The sprayable composition of claim 1, wherein, in the concentrated emulsion, the aqueous-solute fluid comprises water, or a combination of water and one or more polar solute(s).

6. The sprayable composition of claim 1 for use in one or more of nutritional, pharmaceutical, biomedical, over-the-counter (OTC) drug, cosmetic, food, personal care, animal care, veterinary health, household, and pet care applications.

7. The sprayable composition of claim 1, which is in the form of, a light liquid, a light fluid, or a form which has a viscosity of 5000 cps or less and a rheology sufficient to form a spray of preset or desired droplet size upon dispensing from a spray dispenser.

8. The sprayable composition of claim 1, further comprising one or more humectants, and/or one or more neutralizing agents.

9. The sprayable composition of claim 3, wherein, in the concentrated emulsion, the glyceryl acyloate and polyglyceryl acyloate surfactants or emulsifiers have an HLB from about 7 to about 19, or from about 9 to about 18, or from about 11 to about 17.5, and wherein the sucrose acyloate surfactants or emulsifiers have an HLB from about 10 to about 17.5, or from about 12 to about 17, or from about 12.5 to about 16, or from about 13 to about 16.

10. The sprayable composition of claim 1, wherein, in the concentrated emulsion, the one or more hydrophobic agent(s) comprise one or more active or therapeutic agent(s), or combinations thereof.

11. The sprayable composition of claim 1, wherein the process for preparing the concentrated emulsion further comprises: post-treating the first emulsion, or post-treating the second emulsion, such that: pH is raised or lowered by the addition of an alkali or acid, respectively; viscosity is increased or decreased by the addition of a thickening agent or salt, respectively; specific gravity is adjusted by the addition of one or more of an antifoam, centrifugation, vacuum, and reduction in viscosity with sweeping mixing; refractive index is adjusted up or down by the addition of a high refractive index solvent/solute or water; or active levels are adjusted by the addition of a hydrophobic active emulsion.

12. The sprayable composition of claim 10, wherein, in the concentrated emulsion of the sprayable composition, the one or more active or therapeutic agent(s) comprise one or more hydrophobic agent(s) or one or more hydrophilic agent(s), and are at least one selected from the group consisting of: anti-acne agents, antimicrobial agents, anti-inflammatory agents, analgesics, anti-erythemal agents, anti-pruritic agents, anti-edemal agents, anti-psoriatic agents, anti-fungal agents, skin protectants, sunscreen agents, vitamins, antioxidants, scavengers, anti-irritants, anti-bacterial agents, antiviral agents, antiaging agents, photoprotection agents, hair growth enhancers, hair growth inhibitors, hair removal agents, antidandruff agents, anti-seborrheic agents, exfoliating agents, wound healing agents, anti-ectoparasitic agents, sebum modulators, immunomodulators, hormones, botanicals, moisturizing agents, hand sanitizing agents, astringents, sensates, antibiotics, anesthetics, steroids, tissue healing substances, tissue regenerating substances, amino acids, peptides, minerals, ceramides, biohyaluronic acids, bleaching ingredients, pre-biotics, probiotics, hemp oils, cannabinoids, any derivatives or combinations thereof.

13. The sprayable composition of claim 1, wherein in the concentrated emulsion, the one or more hydrophobic agent(s) comprise at least one aesthetic modifying agent.

14. The sprayable composition of claim 1 wherein the process for preparing the concentrated emulsion further comprises: post-treating the first emulsion with at least one functional agent, or post-treating the second emulsion with at least one functional agent.

15. The sprayable composition of claim 13, wherein, in the concentrated emulsion, the one or more hydrophobic aesthetic modifying agent(s) comprise at least one compound selected from the group consisting of: polysiloxanes, cyclic siloxanes, dimethicones, polyalkylsiloxanes, polyarylsiloxanes, polyalkylarylsiloxanes, polysiloxane gums, polyethersiloxane copolymers, and silicone cross polymers.

16. The sprayable composition of claim 5, wherein, in the concentrated emulsion, the one or more polar solutes have a water solubility of 0.1% or greater at a temperature of 23° C. and a pressure of 100 kPa, and have a dielectric constant of greater than 10 at a temperature of 23° C. and a pressure of 100 kPa.

17. The sprayable composition of claim 5, wherein in the concentrate emulsion, the one or more polar solutes are at least one selected from the group consisting of: water soluble solids at a temperature of 23° C. and a pressure of 100 kPa, water soluble liquids at a temperature of 23° C. and a pressure of 100 kPa, and any derivatives or combinations thereof.

18. The sprayable composition of claim 17, wherein, in the concentrated emulsion, the water soluble solids are at least one selected from the group consisting of: carbohydrates; amino acids, peptides, and proteins; vitamins; minerals; and any derivatives or combinations thereof; and wherein the water soluble liquids comprise flowable, non-viscous, semi-viscous, or viscous liquids.

19. The sprayable composition of claim 17, wherein, in the concentrated emulsion, the water soluble liquids are at least one selected from the group consisting of: glyceraldehyde, erythrose, erythrulose, sedoheptulose, and any derivatives or combinations thereof.

20. The sprayable composition of claim 17, wherein, in the concentrated emulsion, the water soluble liquids comprise water miscible liquids; wherein the water miscible liquids are at least one selected from the group consisting of: acetaldehyde, acetic acid, acetone, 1,2-butylene glycol, 1,3-butylene glycol, 1,4-butylene glycol, 2-butoxyethanol, dimethyl sulfoxide, ethanol, ethoxydiglycol, triethylene glycol, ethylene glycol, methanol, isopropanol, 1,2-propylene glycol, 1,3-propylene glycol, 1-propanol, propanoic acid, diglycerin, polyglycerol, glycerin, 1.5-pentylene glycol, hexylene glycol, and any derivatives or combinations thereof.

21. The sprayable composition of claim 1, wherein the one or more additive(s) comprise one or more active or therapeutic ingredient(s); wherein the one or more active or therapeutic ingredient(s) are at least one selected from the group consisting of: anti-acne agents, antimicrobial agents, anti-inflammatory agents, analgesics, anti-erythemal agents, antipruritic agents, antiedemal agents, anti-psoriatic agents, antifungal agents, skin protectants, sunscreen agents, vitamins, antioxidants, anti-irritants, anti-bacterial agents, antiviral agents, antiaging agents, photoprotection agents, exfoliating agents, wound healing agents, sebum modulators, immunomodulators, hormones, botanicals moisturizing agents, hand sanitizing agents, astringents, sensates, antibiotics, anesthetics, steroids, tissue healing substances, tissue regenerating substances, amino acids, peptides, minerals, ceramides, hyaluronic acids, skin bleaching ingredients, pre-biotics, probiotics, hemp oils, cannabinoids, and humectants.

22. The sprayable composition of claim 14, wherein, in the concentrated emulsion, the one or more functional agent(s) are at least one selected from the group consisting of chelating agents, neutralizing agents, foaming agents, rheological modifying agents, sensates, fragrances, and any derivatives or combinations thereof.

23. A process for preparing a concentrated emulsion, said process comprising:
preparing a first emulsion comprising (a) one or more hydrophobic agent(s), (b) an emulsifier system comprising one or more nonionic surfactant(s) or emulsifier(s), (c) an aqueous-solute fluid, and optionally (d) one or more additive(s) or adjuvant(s);
subjecting the first emulsion to low energy mixing, wherein the low energy mixing is mechanical; and
subjecting the first emulsion to ultra-high energy mixing to form a second emulsion, wherein the ultra-high energy mixing is non-mechanical, and wherein the second emulsion comprises said concentrated emulsion;
wherein said concentrated emulsion comprises submicron particles of one or more hydrophobic agent(s), an emulsifier system comprising one or more nonionic surfactant(s) or emulsifier(s), an aqueous-solute fluid, and optionally one or more additive(s) or adjuvant(s);
wherein the submicron particles of one or more hydrophobic agent(s) are present in an amount from about 0.01% wt. to about 70% wt., the aqueous-solute fluid is present in an amount from about 1.0% wt. to about 98.5% wt., and the one or more nonionic surfactant(s) or emulsifier(s) are present in an amount from about 0.01% wt. to about 10% wt., all based on the total weight of the concentrated emulsion;
wherein the submicron particles of one or more hydrophobic agent(s) in the concentrated emulsion have an average particle size from about 100 nm to less than about 1000 nm, have a solubility of less than about 0.1% by weight in water under standard conditions, and are 85% or more of a size within ±2.0 standard deviations, of the average hydrophobic agent(s) particle size in the concentrated emulsion;
wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof;
wherein the one or more nonionic surfactant(s) or emulsifier(s) are sufficient to stabilize the submicron particles of one or more hydrophobic agent(s) in said concentrated emulsion, at a level from about 0.05% w/w to about 70% w/w of said one or more hydrophobic agent(s), in said concentrated emulsion; and
wherein the submicron particles of one or more hydrophobic agent(s) possess a net negative charge after the non-mechanical ultra-high energy mixing, wherein the absolute value of the negative charge is at least 30 mV.

24. The process of claim 23 wherein, after undergoing ultra-high energy mixing, the second emulsion exhibits enhanced stability, as compared to stability exhibited by the first emulsion, after undergoing only low energy mixing.

25. The sprayable composition of claim 1, wherein the concentrated emulsion of the sprayable composition, further comprises one or more humectants.

26. The sprayable composition of claim 1, wherein the concentrated emulsion or the sprayable composition, further comprises one or more neutralizing agents.

27. The sprayable composition of claim 1, further comprising one or more functional agent(s); wherein the one or more functional agent(s) are at least one selected from the group consisting of chelating agents, neutralizing agents, foaming agents, rheological modifying agents, sensates, and any derivatives or combinations thereof.

28. The sprayable composition of claim 1, further comprising one or more active or therapeutic agent(s); wherein the one or more active or therapeutic agent(s) comprise one or more hydrophilic agent(s), and are at least one selected from the group consisting of: anti-acne agents, antimicrobial agents, anti-inflammatory agents, analgesics, anti-erythemal agents, anti-pruritic agents, anti-edemal agents, anti-psoriatic agents, anti-fungal agents, skin protectants, sunscreen agents, vitamins, antioxidants, scavengers, anti-irritants, anti-bacterial agents, antiviral agents, antiaging agents, photoprotection agents, hair growth enhancers, hair growth inhibitors, hair removal agents, antidandruff agents, anti-seborrheic agents, exfoliating agents, wound healing agents, anti-ectoparasitic agents, sebum modulators, immunomodulators, hormones, botanicals, moisturizing agents, hand sanitizing agents, astringents, sensates, antibiotics, anesthetics, steroids, tissue healing substances, tissue regenerating substances, amino acids, peptides, minerals, ceramides, biohyaluronic acids, bleaching ingredients, hemp oils, cannabinoids, and any derivatives or combinations thereof.

29. The sprayable composition of claim 1, wherein, in the concentrated emulsion or the sprayable composition: pH is raised or lowered by the addition of an alkali or acid, respectively; viscosity is increased or decreased by the addition of a thickening agent or salt, respectively; specific gravity is adjusted by the addition of one or more of an antifoam, centrifugation, vacuum, and reduction in viscosity with sweeping mixing; refractive index is adjusted up or down by the addition of a high refractive index solvent/solute or water; or active levels are adjusted by the addition of a hydrophobic active emulsion.

30. The sprayable composition of claim 1, which has a viscosity from about 1 cps to about 5000 cps at 25° C., or from about 1 cps to about 4500 cps at 25° C., or from about 1 cps to about 4000 cps at 25° C., or from about 1 cps to about 3500 cps at 25° C., or from about 1 cps to about 3000 cps at 25° C., or from about 1 cps to about 2500 cps at 25° C., or from about 1 cps to about 2000 cps at 25° C., or from about 1 cps to about 1500 cps at 25° C., or from about 1 cps to about 1000 cps at 25° C., or from about 1 cps to about 500 cps at 25° C.

31. The sprayable composition of claim 1, which is dispensed using a spray dispenser, in a volume which allows for sufficient coverage of a surface; said spray dispenser selected from the group consisting of a bag-on-valve spray dispenser, an aerosol or pressurized spray dispenser, a pump spray dispenser, and a trigger spray dispenser.

32. The sprayable composition of claim 1, which provides a spray of airborne droplets having an aerodynamic equivalent diameter, dae, of greater than about 500 nm and less than about 175 μm.

33. The sprayable composition of claim 1, further comprising a propellent having a positive or pressure at 10° C.; wherein the propellant is present in an amount from about 1 wt % to about 60 wt %, based on the total weight of the sprayable composition; and wherein the propellant is selected from the group consisting of dimethyl ether, liquified petroleum gas (LPG), chlorofluorocarbon, oxygen nitrogen, carbon dioxide, and any derivatives or combinations thereof.

34. A concentrated emulsion comprising:

(a) submicron particles of one or more hydrophobic agent(s);

(b) an emulsifier system comprising one or more nonionic surfactant(s) or emulsifier(s);

(c) an aqueous-solute fluid; and (d) optionally one or more additives or adjuvants;

wherein the submicron particles of one or more hydrophobic agent(s) are present in the concentrated emulsion in an amount from about 0.01% wt. to about 70% wt., the aqueous-solute fluid is present in an amount from about 1.0% wt. to about 98.5% wt., and the one or more nonionic surfactant(s) or emulsifier(s) are present in an amount from about 0.01% wt. to about 10% wt., all based on the total weight of the concentrated emulsion;

wherein the submicron particles of one or more hydrophobic agent(s) in the concentrated emulsion have an average particle size from about 100 nm to less than about 1000 nm, have a solubility of less than about 0.1% by weight in water under standard conditions, and are 85% or more of a size within ±2.0 standard deviations, of the average hydrophobic agent(s) particle size of the concentrated emulsion;

wherein the one or more nonionic surfactant(s) or emulsifier(s) comprise ester(s) of one or more fatty acid moieties with one or more hydroxyl groups of glycerol or polyglycerol having a HLB from about 3 to about 20, based on the degree of glyceryl units or ethoxyl units, or combinations thereof; and optionally ester(s) of one or more fatty acid moieties with one or more hydroxyl groups of sucrose having a HLB from about 2 to about 18, based on the degree of glyceryl units or ethoxyl units, or combinations thereof;

wherein the one or more nonionic surfactant(s) or emulsifier(s) are sufficient to stabilize the submicron particles of one or more hydrophobic agent(s) in said concentrated emulsion, at a level from about 0.05% w/w to about 70% w/w of said one or more hydrophobic agent(s), in said concentrated emulsion;

wherein the concentrated emulsion is prepared by a process comprising:

preparing a first emulsion comprising one or more hydrophobic agent(s), an emulsifier system comprising one or more nonionic surfactant(s) or emulsifier(s), an aqueous-solute fluid, and optionally one or more additive(s) or adjuvant(s);

subjecting the first emulsion to low energy mixing, wherein the low energy mixing is mechanical; and subjecting the first emulsion to ultra-high energy mixing to form a second emulsion, wherein the ultra-high energy mixing is non-mechanical;

wherein the second emulsion comprises said concentrated emulsion; and wherein the submicron particles of one or more hydrophobic agent(s) possess a net negative charge after the non-mechanical ultra-high energy mixing, wherein the absolute value of the negative charge is at least 30 m V.

* * * * *